(12) United States Patent
Song et al.

(10) Patent No.: US 11,534,431 B2
(45) Date of Patent: *Dec. 27, 2022

(54) COMBINATION OF A PD-1 ANTAGONIST AND A RAF INHIBITOR FOR TREATING CANCER

(71) Applicant: BeiGene, Ltd., Grand Cayman (KY)

(72) Inventors: Jing Song, Beijing (CN); Lai Wang, Beijing (CN); Kang Li, Beijing (CN); Tong Zhang, Beijing (CN); Lusong Luo, Beijing (CN); Min Wei, Beijing (CN); Zhiyu Tang, Beijing (CN); Guoliang Zhang, Beijing (CN); Changyou Zhou, Princeton, NJ (US)

(73) Assignee: BEIGENE SWITZERLAND GMBH, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/099,115

(22) Filed: Nov. 16, 2020

(65) Prior Publication Data

US 2021/0228553 A1 Jul. 29, 2021

Related U.S. Application Data

(63) Continuation of application No. 16/315,539, filed as application No. PCT/IB2017/053521 on Jun. 14, 2017, now Pat. No. 10,864,203.

(30) Foreign Application Priority Data

Jul. 5, 2016 (CN) .................. PCT/CN2016/088591

(51) Int. Cl.
*A61K 31/4375* (2006.01)
*A61P 35/00* (2006.01)
*C07K 16/28* (2006.01)

(52) U.S. Cl.
CPC .......... *A61K 31/4375* (2013.01); *A61P 35/00* (2018.01); *C07K 16/2818* (2013.01)

(58) Field of Classification Search
CPC ...... A61K 31/4375; A61K 38/02; A61P 35/00
USPC .................................................. 514/300, 1.1
See application file for complete search history.

(56) References Cited

U.S. PATENT DOCUMENTS

| | | | |
|---|---|---|---|
| 5,624,821 A | 4/1997 | Winter et al. |
| 5,629,204 A | 5/1997 | Honjo et al. |
| 5,648,260 A | 7/1997 | Winter et al. |
| 5,698,520 A | 12/1997 | Honjo et al. |
| 5,994,514 A | 11/1999 | Jardieu et al. |
| 6,165,745 A | 12/2000 | Ward et al. |
| 6,194,551 B1 | 2/2001 | Idusogie et al. |
| 6,528,624 B1 | 3/2003 | Idusogie et al. |
| 6,632,927 B2 | 10/2003 | Adair et al. |
| 6,737,056 B1 | 5/2004 | Presta |
| 6,808,710 B1 | 10/2004 | Wood et al. |
| 6,936,704 B1 | 8/2005 | Freeman et al. |
| 7,029,674 B2 | 4/2006 | Carreno et al. |
| 7,038,013 B2 | 5/2006 | Freeman et al. |
| 7,101,550 B2 | 9/2006 | Wood et al. |
| 7,122,637 B2 | 10/2006 | Presta |
| 7,297,775 B2 | 11/2007 | Idusogie et al. |
| 7,317,091 B2 | 1/2008 | Lazar et al. |
| 7,332,581 B2 | 2/2008 | Presta |
| 7,335,742 B2 | 2/2008 | Presta |
| 7,355,008 B2 | 4/2008 | Stavenhagen et al. |
| 7,364,731 B2 | 4/2008 | Idusogie et al. |
| 7,371,826 B2 | 5/2008 | Presta |
| 7,393,848 B2 | 7/2008 | Currie et al. |
| 7,414,171 B2 | 8/2008 | Honjo et al. |
| 7,416,726 B2 | 8/2008 | Ravetch |
| 7,488,802 B2 | 2/2009 | Collins et al. |
| 7,514,444 B2 | 4/2009 | Honigberg et al. |
| 7,563,869 B2 | 7/2009 | Honjo et al. |
| 7,595,048 B2 | 9/2009 | Honjo et al. |
| 7,597,889 B1 | 10/2009 | Armour et al. |
| 7,608,429 B2 | 10/2009 | Reilly et al. |
| 7,635,757 B2 | 12/2009 | Freeman et al. |
| 7,638,492 B2 | 12/2009 | Wood et al. |
| 7,655,783 B2 | 2/2010 | Reilly et al. |
| 7,670,600 B2 | 3/2010 | Dall'Acqua et al. |
| 7,718,662 B1 | 5/2010 | Chen et al. |

(Continued)

FOREIGN PATENT DOCUMENTS

| CN | 1753912 A | 3/2006 |
|---|---|---|
| CN | 1771231 A | 5/2006 |
| CN | 101104640 A | 1/2008 |
| CN | 101213297 A | 7/2008 |

(Continued)

OTHER PUBLICATIONS

Abdiche et al., "Assessing kinetic and epitopic diversity across orthogonal monoclonal antibody generation platforms." mABs (Feb.-Mar. 2016); 8(2):264-277.

(Continued)

*Primary Examiner* — Charanjit Aulakh

(74) *Attorney, Agent, or Firm* — Cooley LLP

(57) ABSTRACT

Disclosed herein is a pharmaceutical combination for use in the prevention, delay of progression or treatment of cancer, wherein the pharmaceutical combination exhibits a synergistic efficacy. The pharmaceutical combination comprises a humanized antagonist monoclonal antibody against PD- and a RAF inhibitor. Also disclosed herein is a combination for use in the prevention, delay of progression or treatment of cancer in a subject, comprising administering to the subject a therapeutically effective amount of a humanized antagonist monoclonal antibody against PD-1 and a therapeutically effective amount of a RAF inhibitor.

21 Claims, 6 Drawing Sheets

Specification includes a Sequence Listing.

(56) References Cited

U.S. PATENT DOCUMENTS

| | | |
|---|---|---|
| 7,741,072 B2 | 6/2010 | Idusogie et al. |
| 7,790,858 B2 | 9/2010 | Presta |
| 7,851,598 B2 | 12/2010 | Davis |
| 7,863,419 B2 | 1/2011 | Taylor et al. |
| 7,943,743 B2 | 5/2011 | Korman et al. |
| 7,998,479 B2 | 8/2011 | Honjo et al. |
| 8,008,449 B2 | 8/2011 | Korman et al. |
| 8,084,620 B2 | 12/2011 | Liu et al. |
| 8,088,905 B2 | 1/2012 | Collins et al. |
| 8,110,687 B2 | 2/2012 | Calderwood et al. |
| 8,168,179 B2 | 5/2012 | Honjo et al. |
| 8,168,757 B2 | 5/2012 | Finnefrock et al. |
| 8,217,149 B2 | 7/2012 | Irving et al. |
| 8,246,955 B2 | 8/2012 | Honjo et al. |
| 8,354,509 B2 | 1/2013 | Carven et al. |
| 8,552,154 B2 | 10/2013 | Freeman et al. |
| 8,617,546 B2 | 12/2013 | Kang et al. |
| 8,728,474 B2 | 5/2014 | Honjo et al. |
| 8,735,553 B1 | 5/2014 | Li et al. |
| 8,779,105 B2 | 7/2014 | Korman et al. |
| 8,911,726 B2 | 12/2014 | Takahashi et al. |
| 8,945,561 B2 | 2/2015 | Davis |
| 9,067,999 B1 | 6/2015 | Honjo et al. |
| 9,073,994 B2 | 7/2015 | Honjo et al. |
| 9,084,776 B2 | 7/2015 | Korman et al. |
| 9,139,653 B1 | 9/2015 | Campbell et al. |
| 9,175,082 B2 | 11/2015 | Zhou et al. |
| 9,217,034 B2 | 12/2015 | Li et al. |
| 9,273,046 B2 | 3/2016 | Zhou et al. |
| 9,447,106 B2 | 9/2016 | Wang et al. |
| 9,492,540 B2 | 11/2016 | Korman et al. |
| 9,556,188 B2 | 1/2017 | Wang et al. |
| 9,624,298 B2 | 4/2017 | Nastri et al. |
| 9,834,606 B2 | 12/2017 | Li et al. |
| 9,895,376 B2 | 2/2018 | Zhou et al. |
| 9,920,123 B2 | 3/2018 | Irving et al. |
| 9,988,450 B2 | 6/2018 | Li et al. |
| 10,005,782 B2 | 6/2018 | Wang et al. |
| 10,058,609 B2 | 8/2018 | Zhou et al. |
| 10,351,559 B2 | 7/2019 | Zhang et al. |
| 10,487,147 B2 | 11/2019 | Nastri et al. |
| 10,519,235 B2 | 12/2019 | Li et al. |
| 10,544,225 B2 | 1/2020 | Li et al. |
| 10,550,185 B2 | 2/2020 | Bernett et al. |
| 10,570,139 B2 | 2/2020 | Wang et al. |
| 10,576,087 B2 | 3/2020 | Zhou et al. |
| 10,793,632 B2 | 10/2020 | Bernett et al. |
| 10,858,435 B2 | 12/2020 | Finlay |
| 10,864,203 B2 | 12/2020 | Song et al. |
| 10,927,117 B2 | 2/2021 | Wang et al. |
| 11,186,637 B2 | 11/2021 | Li et al. |
| 11,202,782 B2 | 12/2021 | Wang et al. |
| 11,203,637 B2 | 12/2021 | Zhang et al. |
| 2002/0094989 A1 | 7/2002 | Hale et al. |
| 2004/0038339 A1 | 2/2004 | Kufer et al. |
| 2005/0064514 A1 | 3/2005 | Stavenhagen et al. |
| 2005/0202028 A1 | 9/2005 | Ledbetter et al. |
| 2006/0121032 A1 | 6/2006 | Dahiyat et al. |
| 2006/0134105 A1 | 6/2006 | Lazar et al. |
| 2006/0178367 A1 | 8/2006 | Currie et al. |
| 2006/0183746 A1 | 8/2006 | Currie et al. |
| 2006/0263856 A1 | 11/2006 | Gillies et al. |
| 2007/0160597 A1 | 7/2007 | Lazar et al. |
| 2008/0076921 A1 | 3/2008 | Honigberg et al. |
| 2008/0139582 A1 | 6/2008 | Honigberg et al. |
| 2009/0068175 A1 | 3/2009 | Lazar et al. |
| 2009/0105209 A1 | 4/2009 | Dewdney et al. |
| 2009/0155256 A1 | 6/2009 | Black et al. |
| 2009/0217401 A1 | 8/2009 | Korman et al. |
| 2009/0318441 A1 | 12/2009 | Brain et al. |
| 2010/0004231 A1 | 1/2010 | Dewdney et al. |
| 2010/0016296 A1 | 1/2010 | Singh et al. |
| 2010/0016301 A1 | 1/2010 | Dewdney et al. |
| 2010/0029610 A1 | 2/2010 | Singh et al. |
| 2010/0035841 A1 | 2/2010 | Jankowski et al. |
| 2010/0087464 A1 | 4/2010 | Mi et al. |
| 2010/0105676 A1 | 4/2010 | Liu et al. |
| 2010/0144705 A1 | 6/2010 | Miller |
| 2010/0151492 A1 | 6/2010 | Ahmed et al. |
| 2010/0160292 A1 | 6/2010 | Whitney et al. |
| 2010/0160303 A1 | 6/2010 | Liu et al. |
| 2010/0184791 A1 | 7/2010 | Li et al. |
| 2010/0197924 A1 | 8/2010 | Gould et al. |
| 2010/0222325 A1 | 9/2010 | Berthel et al. |
| 2010/0249092 A1 | 9/2010 | Singh et al. |
| 2010/0254905 A1 | 10/2010 | Honigberg et al. |
| 2010/0292205 A1 | 11/2010 | Lefker et al. |
| 2010/0317834 A1 | 12/2010 | Lazar et al. |
| 2011/0008369 A1 | 1/2011 | Finnefrock et al. |
| 2011/0052584 A1 | 3/2011 | Ravetch |
| 2011/0054151 A1 | 3/2011 | Lazar et al. |
| 2011/0118233 A1 | 5/2011 | Blomgren et al. |
| 2011/0124640 A1 | 5/2011 | Liu et al. |
| 2011/0159023 A1 | 6/2011 | Langermann |
| 2011/0171215 A1 | 7/2011 | Davis et al. |
| 2011/0171220 A1 | 7/2011 | Davis |
| 2011/0177088 A1 | 7/2011 | Olive et al. |
| 2011/0195068 A1 | 8/2011 | Langermann et al. |
| 2011/0224235 A1 | 9/2011 | Honigberg et al. |
| 2011/0271358 A1 | 11/2011 | Freeman et al. |
| 2011/0287032 A1 | 11/2011 | Lazar et al. |
| 2011/0301145 A1 | 12/2011 | Barbosa, Jr. et al. |
| 2012/0028981 A1 | 2/2012 | Miller |
| 2012/0040961 A1 | 2/2012 | Gray et al. |
| 2012/0053189 A1 | 3/2012 | Loury |
| 2012/0058996 A1 | 3/2012 | Liu et al. |
| 2012/0076726 A1 | 3/2012 | Gellerfors et al. |
| 2012/0077832 A1 | 3/2012 | Witowski et al. |
| 2012/0082702 A1 | 4/2012 | DeLucca et al. |
| 2012/0129852 A1 | 5/2012 | Duan et al. |
| 2012/0157442 A1 | 6/2012 | Bui et al. |
| 2012/0157443 A1 | 6/2012 | Bui et al. |
| 2012/0232054 A1 | 9/2012 | Moriarty et al. |
| 2012/0237522 A1 | 9/2012 | Kang et al. |
| 2012/0251531 A1 | 10/2012 | Baehner et al. |
| 2013/0004514 A1 | 1/2013 | Zahn et al. |
| 2013/0079327 A1 | 3/2013 | Yamamoto et al. |
| 2013/0089541 A1 | 4/2013 | D'Angelo et al. |
| 2013/0096118 A1 | 4/2013 | Liu et al. |
| 2013/0116213 A1 | 5/2013 | Cha et al. |
| 2013/0259868 A1 | 10/2013 | Roschke et al. |
| 2013/0261103 A1 | 10/2013 | Currie et al. |
| 2013/0281432 A1 | 10/2013 | Currie et al. |
| 2013/0309250 A1 | 11/2013 | Cogswell et al. |
| 2014/0044738 A1 | 2/2014 | Langermann et al. |
| 2014/0045833 A1 | 2/2014 | Laurent et al. |
| 2014/0094459 A1 | 4/2014 | Goldstein et al. |
| 2014/0107151 A1 | 4/2014 | Goldstein et al. |
| 2014/0162316 A1 | 6/2014 | O'Neil et al. |
| 2014/0162983 A1 | 6/2014 | Hodous et al. |
| 2014/0221398 A1 | 8/2014 | Goldstein et al. |
| 2014/0243306 A1 | 8/2014 | Heng et al. |
| 2014/0243504 A1 | 8/2014 | Davis et al. |
| 2014/0245468 A1 | 8/2014 | McWhirter et al. |
| 2014/0271642 A1 | 9/2014 | Murphy et al. |
| 2014/0314714 A1 | 10/2014 | Honjo et al. |
| 2014/0341902 A1 | 11/2014 | Maecker et al. |
| 2014/0356363 A1 | 12/2014 | Zhou et al. |
| 2014/0377269 A1 | 12/2014 | Mabry et al. |
| 2015/0044231 A1 | 2/2015 | Kjaergaard et al. |
| 2015/0079109 A1 | 3/2015 | Li et al. |
| 2015/0125444 A1 | 5/2015 | Tsui et al. |
| 2015/0210763 A1 | 7/2015 | Kuramochi et al. |
| 2015/0259354 A1 | 9/2015 | Wang et al. |
| 2015/0315274 A1 | 11/2015 | Li et al. |
| 2015/0337053 A1 | 11/2015 | McCarthy et al. |
| 2015/0353631 A1 | 12/2015 | Buttini et al. |
| 2016/0083392 A1 | 3/2016 | Wang et al. |
| 2016/0206621 A1 | 7/2016 | Zhou et al. |
| 2017/0044260 A1 | 2/2017 | Baruah et al. |
| 2017/0073349 A1 | 3/2017 | Wang et al. |
| 2018/0037655 A1 | 2/2018 | Hegde et al. |
| 2018/0127412 A1 | 5/2018 | Zhang et al. |
| 2018/0215825 A1 | 8/2018 | Li et al. |

(56) References Cited

U.S. PATENT DOCUMENTS

| | | |
|---|---|---|
| 2018/0251466 A1 | 9/2018 | Wang et al. |
| 2018/0251551 A1 | 9/2018 | Li et al. |
| 2019/0000857 A1 | 1/2019 | Zhou et al. |
| 2019/0169201 A1 | 6/2019 | Wang et al. |
| 2020/0030339 A1 | 1/2020 | Wang et al. |
| 2020/0069666 A1 | 3/2020 | Song et al. |
| 2020/0148690 A1 | 5/2020 | Wang et al. |
| 2020/0181150 A1 | 6/2020 | Wang et al. |
| 2020/0216535 A1 | 7/2020 | Li et al. |
| 2020/0283527 A1 | 9/2020 | Li et al. |
| 2020/0368237 A1 | 11/2020 | Hilger et al. |
| 2021/0040213 A1 | 2/2021 | Song et al. |
| 2021/0130363 A1 | 5/2021 | Wang et al. |
| 2021/0147543 A1 | 5/2021 | Wang et al. |
| 2021/0230274 A1 | 7/2021 | Li et al. |
| 2021/0275530 A1 | 9/2021 | Hu et al. |

FOREIGN PATENT DOCUMENTS

| | | |
|---|---|---|
| CN | 101355965 A | 1/2009 |
| CN | 101899114 A | 12/2010 |
| CN | 102245640 A | 11/2011 |
| CN | 102264762 A | 11/2011 |
| CN | 102656173 A | 9/2012 |
| CN | 104884458 A | 9/2015 |
| CN | 105531288 A | 4/2016 |
| CN | 106103485 A | 11/2016 |
| CN | 107011441 A | 8/2017 |
| CN | 107090041 A | 8/2017 |
| GB | 1412017 A | 10/1975 |
| JP | H07278148 A | 10/1995 |
| JP | 2006510582 A | 3/2006 |
| JP | 2008523099 A | 7/2008 |
| JP | 2008544755 A | 12/2008 |
| JP | 2009519908 A | 5/2009 |
| JP | 2009155338 A | 7/2009 |
| JP | 2009537524 A | 10/2009 |
| JP | 2010502706 A | 1/2010 |
| JP | 2010504324 A | 2/2010 |
| JP | 2010528993 A | 8/2010 |
| JP | 2012511329 A | 5/2012 |
| JP | 2012254092 A | 12/2012 |
| JP | 5868521 B2 | 2/2016 |
| KR | 20080011428 A | 2/2008 |
| KR | 20100054780 A | 5/2010 |
| WO | WO-9429351 A2 | 12/1994 |
| WO | WO-0116138 A1 | 3/2001 |
| WO | WO-0119829 A2 | 3/2001 |
| WO | WO-0250071 A1 | 6/2002 |
| WO | WO-02072576 A1 | 9/2002 |
| WO | WO-03004497 A1 | 1/2003 |
| WO | WO-2004017908 A2 | 3/2004 |
| WO | WO-2005005429 A1 | 1/2005 |
| WO | WO-2005011597 A2 | 2/2005 |
| WO | WO-2005014599 A1 | 2/2005 |
| WO | WO-2005047290 A2 | 5/2005 |
| WO | WO-2005077981 A2 | 8/2005 |
| WO | WO-2006053121 A2 | 5/2006 |
| WO | WO-2006065703 A1 | 6/2006 |
| WO | WO-2006065946 A1 | 6/2006 |
| WO | WO-2006084015 A2 | 8/2006 |
| WO | WO-2006099075 A2 | 9/2006 |
| WO | WO-2006121168 A1 | 11/2006 |
| WO | WO-2006133396 A2 | 12/2006 |
| WO | WO-2007005874 A2 | 1/2007 |
| WO | WO-2007026720 A1 | 3/2007 |
| WO | WO-2007026950 A1 | 3/2007 |
| WO | WO-2007027594 A1 | 3/2007 |
| WO | WO-2007027729 A1 | 3/2007 |
| WO | WO-2007067444 A1 | 6/2007 |
| WO | WO-2007087068 A2 | 8/2007 |
| WO | WO-2007136572 A2 | 11/2007 |
| WO | WO-2007136573 A2 | 11/2007 |
| WO | WO-2007136790 A2 | 11/2007 |
| WO | WO-2008030448 A1 | 3/2008 |
| WO | WO-2008033834 A1 | 3/2008 |
| WO | WO-2008033854 A1 | 3/2008 |
| WO | WO-2008033857 A2 | 3/2008 |
| WO | WO-2008039218 A2 | 4/2008 |
| WO | WO-2008054827 A2 | 5/2008 |
| WO | WO-2008144253 A1 | 11/2008 |
| WO | WO-2008145142 A1 | 12/2008 |
| WO | WO-2008156712 A1 | 12/2008 |
| WO | WO-2009039397 A2 | 3/2009 |
| WO | WO-2009051822 A1 | 4/2009 |
| WO | WO-2009077334 A1 | 6/2009 |
| WO | WO-2009098144 A1 | 8/2009 |
| WO | WO-2009158571 A1 | 12/2009 |
| WO | WO-201 0000633 A1 | 1/2010 |
| WO | WO-2010006947 A1 | 1/2010 |
| WO | WO-2010006970 A1 | 1/2010 |
| WO | WO-2010028236 A1 | 3/2010 |
| WO | WO-2010051549 A1 | 5/2010 |
| WO | WO-2010065898 A2 | 6/2010 |
| WO | WO-2010068788 A1 | 6/2010 |
| WO | WO-2010068806 A1 | 6/2010 |
| WO | WO-2010068810 A2 | 6/2010 |
| WO | WO-2010077634 A1 | 7/2010 |
| WO | WO-2010089411 A2 | 8/2010 |
| WO | WO-2010122038 A1 | 10/2010 |
| WO | WO-2011006074 A1 | 1/2011 |
| WO | WO-2011140488 A1 | 11/2011 |
| WO | WO-2011153514 A2 | 12/2011 |
| WO | WO-2012020008 A1 | 2/2012 |
| WO | WO-2012083370 A1 | 6/2012 |
| WO | WO-2012130831 A1 | 10/2012 |
| WO | WO-2012135408 A1 | 10/2012 |
| WO | WO-2012135801 A1 | 10/2012 |
| WO | WO-2012143522 A1 | 10/2012 |
| WO | WO-2012145493 A1 | 10/2012 |
| WO | WO-2012156334 A1 | 11/2012 |
| WO | WO-2012158795 A1 | 11/2012 |
| WO | WO-2012175692 A1 | 12/2012 |
| WO | WO-2013079174 A1 | 6/2013 |
| WO | WO-2013097224 A1 | 7/2013 |
| WO | WO-2013173223 A1 | 11/2013 |
| WO | WO-2013181634 A2 | 12/2013 |
| WO | WO-2014055897 A2 | 4/2014 |
| WO | WO-2014100079 A1 | 6/2014 |
| WO | WO-2014173289 A1 | 10/2014 |
| WO | WO 2014/193898 A1 * | 12/2014 ........... A61K 31/506 |
| WO | WO-2015035606 A1 | 3/2015 |
| WO | WO-2015061752 A1 | 4/2015 |
| WO | WO-2015112900 A1 | 7/2015 |
| WO | WO-2016000619 A1 | 1/2016 |
| WO | WO-2016008411 A1 | 1/2016 |
| WO | WO-2016024228 A1 | 2/2016 |
| WO | WO-2016025720 A1 | 2/2016 |
| WO | WO-2016064649 A1 | 4/2016 |
| WO | WO-2016087994 A1 | 6/2016 |
| WO | WO-2016100914 A1 | 6/2016 |
| WO | WO-2016105582 A1 | 6/2016 |
| WO | WO-2016165626 A1 | 10/2016 |
| WO | WO-2017025016 A1 | 2/2017 |
| WO | WO-2017046746 A1 | 3/2017 |
| WO | WO-2017059224 A2 | 4/2017 |
| WO | WO 2017/165491 A1 * | 9/2017 ......... A61K 31/4745 |
| WO | WO-2018033135 A1 | 2/2018 |
| WO | WO-2018033853 A2 | 2/2018 |
| WO | WO-2018137681 A1 | 8/2018 |
| WO | WO-2018193105 A1 | 10/2018 |
| WO | WO-2019001417 A1 | 1/2019 |
| WO | WO-2019034009 A1 | 2/2019 |
| WO | WO-2019108795 A1 | 6/2019 |
| WO | WO-2019157353 A1 | 8/2019 |

OTHER PUBLICATIONS

Agata, Y. et al., "Expression of the PD-1 antigen on the surface of stimulated mouse T and B lymphocytes," Int. Immunol., 8(5):765-772 (May 1996).

Ahmadzadeh, M. et al., "Tumor antigen-specific CD8 T cells infiltrating the tumor express high levels of PD-1 and are function-

(56) References Cited

OTHER PUBLICATIONS ally impaired," Blood. Aug. 20, 2009;114(8):1537-1544. doi: 10.1182/blood-2008-12-195792. Epub May 7, 2009.
Araki, K. et al., "Programmed cell death 1-directed immunotherapy for enhancing T-cell function," Cold Spring Harbor Symposia on Quantitative Biology, vol. LXXVIII, 239-247 (2013).
Arlauckas, S.P. et al., "In vivo imaging reveals a tumor-associated macrophage-mediated resistance pathway in anti-PD-1 therapy," Sci. Transl. Med., 9, eaal3604 (May 2017).
Balar, A. et al., "Pembrolizumab (pembro) as first-line therapy for advanced/unresectable or metastatic urothelial cancer: Preliminary results from the phase 2 KEYNOTE-052 study," Annals of Oncology 27 (Supplement 6): vi552-vi587, 2016.
Balbach, S. et al., "Pharmaceutical evaluation of early development candidates the 100 mg-approach," International Journal of Pharmaceutics, 275 (2004), pp. 1-12.
Banales, "Cholangiocarcinoma: current knowledge and future perspectives consensus statement from the European Network for the Study of Cholangiocarcinoma (ENS-CCA)," Nature Reviews Gastroenterology and Hepatology, 2016, 13:261-280.
Bellmunt, J. et al., "Keynote-045: open-label, phase II study of pembrolizumab versus investigator's choice of paclitaxel, docetaxel, or vinflunine for previously treated advanced urothelial cancer," Journal for ImmunoTherapy of Cancer, 2016, 4(Suppl. 2):91, Presented at 31st Society for Immunotherapy of Cancer Annual Meeting, Nov. 9-13, 2016, National Harbor, MD, 1 page.
Bellmunt, J. et al., "Pembrolizumab as Second-Line Therapy for Advanced Urothelial Carcinoma," N. Engl. J. Med., vol. 376, No. 11, Mar. 2017, pp. 1015-1026.
Bellmunt, J. et al., "Randomized Phase III Study Comparing Paclitaxel/Cisplatin/Gemcitabine and Gemcitabine/Cisplatin in Patients with Locally Advanced or Metastatic Urothelial Cancer Without Prior Systemic Therapy: EORTC Intergroup Study 30987," J Clin Oncol., Apr. 1, 2012;30(10):1107-1113.
Bennett, F. et al., "Program death-1 engagement upon TCR activation has distinct effects on costimulation and cytokine-driven proliferation: attenuation of ICOS, IL-4 and IL-21, but not CD28, IL-7, and IL-15 responses," J. Immunol. 170:711-118 (2003).
Berger, R. et al., "Phase I safety and pharmacokinetic study of CT-011, a humanized antibody interacting with PD-1, in patients with advanced hematologic malignancies," Clinical Cancer Research, 14(10):3044-3051 (May 2008).
Blackburn, C. et al., "Discovery and optimization of N-acyl and N-aroylpyrazolines as B-Raf kinase inhibitors," Bioorganic & Medicinal Chemistry Letters 20 (201 0) 4795-4799.
Blank, C. et al., "Interaction of PD-L1 on tumor cells with PD-1 on tumor-specific T cells as a mechanism of immune evasion: implications for tumor immunotherapy," Cancer Immunol Immunother 54(4):307-314 (Apr. 2005).
Boniface, M. M. et al., "Multidisciplinary management for esophageal and gastric cancer," Cancer Management and Research, 2016:8 39-44.
Bour-Jordan, H. et al., "Intrinsic and extrinsic control of peripheral T-cell tolerance by costimulatory molecules of the CD28/ B7 family," Immunol. Rev. 241(1):180-205 (2011).
Bowker, M. J. et al., "A Procedure for Salt Selection and Optimization," Chapter 7 In: Handbook of Pharmaceutical Salts: Properties, Selection, and Use, Helvetica Chimca ACTA, pp. 162-173 (Jan. 2002).
Boyd et al., "Deep sequencing and human antibody repertoire analysis." Current Opinion in Immunology (Jun. 2016); 40: 103-109. Epub Apr. 8, 2016.
Bradshaw, J. M., "The Src, Syk, and Tec family kinases: Distinct types of molecular switches," Cell Signalling, 22:1175-1184 (2010).
Brahmer, J. R. et al., "Safety and Activity of Anti-PD-L1 Antibody in Patients with Advanced Cancer," N Engl J Med. (Jun. 28, 2012), 366(26):2455-2465.
Brahmer, J. R. et al., "Phase I study of single-agent anti-programmed death-1 (MDX-1106) in refractory solid tumors: safety, clinical activity, pharmacodynamics, and immunologic correlates," J Clin Oncol. Jul. 1, 2010;28(19):3167-75.
Brand, F-X et al., "Prospect for anti-HER2 receptor therapy in breast cancer," Anticancer Research, 26:463-470 (2006).
Caira, M. R., "Crystalline polymorphism of organic compounds," Topics in Current Chemistry, vol. 198, 1998, pp. 163-208.
Cantwell-Dorris, "BRAFV600E: Implications for Carcinogenesis and Molecular Therapy," Mol Cancer Ther., 10(3):385-394 (Mar. 2011).
Cartigny, D. et al., "General Asymmetric Hydrogenation of 2-Alkyl- and 2-Aryl-Substituted Quinoxaline Derivatives Catalyzed by Iridium-Difluorphos: Unusual Halide Effect and Synthetic Application," J. Org. Chem., Apr. 2012, vol. 77, No. 10, pp. 4544-4556.
Casset, F. et al., "A peptide mimetic of an anti-CD4 monoclonal antibody by rational design," Biochemical and Biophysical Research Communications, 307:198-205 (2003).
Chemical Abstract compound, STN Express, RN 1854985-74-2 (Entered STN: Jan. 28, 2016).
Chia-Jui, Y. et al., Abstract of "Preliminary results of a phase 1A/1B study of BGB-A317, an anti-PD-1 monoclonal antibody (mAb), in patients with advanced hepatocellular carcinoma (HCC)," Annals of Oncology (2017).
Chothia, C. et al., "Canonical structures for the hypervariable regions of immunoglobulins," J Mol Biol., Aug. 20, 1987;196(4):901-917.
Chothia, C. et al., "Conformations of immunoglobulin hypervariable regions," Nature 342:877-883 (Dec. 1989).
Clynes, R. A. et al., "Inhibitory Fc receptors modulate in vivo cytoxicity against tumor targets," Nat. Med. 6(4):443-446 (Apr. 2000).
Conley, M. E. et al., "Primary B Cell Immunodeficiencies: Comparisons and Contrasts," Annu. Rev. Immunol., 27:199-227 (2009).
Conroy, et al., "Antibodies: From novel repertoires to defining and refining the structure of biologically important targets," Methods (Mar. 2017); 116:12-22. Epub Jan. 11, 2017.
Dahan, R. et al., "FcRs Modulate the Anti-tumor Activity of Antibodies Targeting the PD-1/PD-L1 Axis," Cancer Cell (Sep. 2015), 28(3):285-95. doi: 10.1016/j.ccell.2015.08.004.
Damia, G. et al., "Contemporary pre-clinical development of anticancer agents—What are the optimal preclinical models?" European Journal of Cancer, 45 (2009) 2768-2781.
Damschroder et al., "Analysis of human and primate CD2 molecules by protein sequence and epitope mapping with anti-human CD2 antibodies," Mol Immunol. (Aug. 2004), 41(10):985-1000.
Davis, R. E. et al., "Chronic active B-cell-receptor signalling in diffuse large B-cell lymphoma," Nature, 463:88-92 (2010).
De Pascalis, R. et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology, vol. 169, pp. 3076-3084 (2002).
De Toni, E. N. et al., "Tapering of Immunosuppression and Sustained Treatment With Nivolumab in a Liver Transplant Recipient," Gastroenterology, May 2017;152(6):1631-1633. doi: 10.1053/j.gastro.2017.01.063.
Desai, J. et al., "Updated safety, efficacy, and pharmacokinetics (PK) results from thephase I study of BGB-A317, an anti-programmed death-1 (PD-1) mAb in patients with advanced solid tumors," J. Immunother. Cancer, 2016; 4(Suppl 1):P154, 2 pages.
Dorfman, D. M. et al., "Programmed death-1 (PD-1) is a marker of germinal center-associated T Cells and angioimmunoblastic T-cell lymphoma," American Journal of Surgical Pathology, 30(7):802-810 (Jul. 2006).
El-Khoueiry, A. B. et al., "Nivolumab in patients with advanced hepatocellular carcinoma (CheckMate 040): an open-label, non-comparative, phase 1/2 dose escalation and expansion trial," Lancet, . Jun. 24, 2017;389(10088):2492-2502. doi: 10.1016/S0140-6736(17)31046-2.
European Search Report for European Application No. 16167542.6, dated Nov. 14, 2016, 5 pages.
Extended European Search Report for European Application No. 14787642.9, dated Jan. 26, 2016, 5 pages.

(56) References Cited

OTHER PUBLICATIONS

Extended European Search Report for European Application No. 15815646.3, dated Dec. 21, 2017, 10 pages.
Extended European Search Report for European Application No. 16779601.0, dated Jul. 24, 2018, 6 pages.
Extended European Search Report for European Application No. 17841107.0, dated Feb. 21, 2020, 12 pages.
Extended European Search Report for European Application No. 17841172.4, dated Mar. 5, 2020, 6 pages.
Extended European Search Report for European Application No. 18744173.8, dated Oct. 21, 2020, 12 pages.
Extended European Search Report for European Application No. 18823691.3, dated Feb. 22, 2021, 9 pages.
Extended Supplementary European Search Report for European Application No. 11879096.3, dated Jul. 30, 2015, 4 pages.
Ferrara et al., "Recombinant renewable polyclonal antibodies." mABs (2015); 7(1):32-41.
Fuller, M. J. et al., "Immunotherapy of chronic hepatitis C virus infection with antibodies against programmed cell death-1 (PD-1)," Proceedings of the National Academy of Sciences, 110(37):15001-15006 (Sep. 2013).
Galsky, M. D. et al., "Effectiveness of Adjuvant Chemotherapy for Locally Advanced Bladder Cancer," J Clin Oncol. Mar. 10, 2016;34(8):825-832.
Gao, Q. et al., "Overexpression of PD-L1 significantly associates with tumor aggressiveness and postoperative recurrence in human hepatocellular carcinoma," Clin Cancer Res., Feb. 1, 2009;15(3):971-979.
Garson, "Models of ovarian cancer—Are we there yet?," Molecular and Cellular Endocrinology 239 (2005) 15-26.
Gelderman, K. A. et al., "Complement function in mAb-mediated cancer immunotherapy," Trends in Immunology, 25(3):158-164 (Mar. 2004).
Gerratana, L. et al., "Do platinum salts fit all triple negative breast cancers?" Cancer Treatment Reviews 48 (2016) 34-41.
Ghebeh, H. et al., "The B7-H1 (PD-L1) T lymphocyte-inhibitory molecule is expressed in breast cancer patients with infiltrating ductal carcinoma: correlation with important high-risk prognostic factors," Neoplasia, Mar. 2006;8(3):190-198.
Gurcan, H. M. et al., "A review of the current use of rituximab in autoimmune diseases," Int. Immunopharmacol., 9:10-25 (2009).
Gyawali, B. et al., "Chemotherapy in locally advanced head and neck squamous cell carcinoma," Cancer Treatment Reviews, 44 (2016) 10-16.
Hackam, D. G. et al., "Translation of research evidence from animals to humans," JAMA, 296(14):1731-1732 (2006).
Hamanishi, J. et al., "Programmed cell death 1 ligand 1 and tumor-infiltrating CD8 + T lymphocytes are prognostic factors of human ovarian cancer," Proc. Natl Acad Sci. 104(9):3360-3365 (Feb. 2007).
Hamid, O. et al., "Safety and tumor responses with lambrolizumab (Anti-PD-1) in melanoma," New England Journal of Medicine, 369(2):134-144 (Jul. 2013).
Hino, R. et al., "Tumor cell expression of programmed cell death-1 ligand 1 is a prognostic factor for malignant melanoma," Cancer, 116(7):1757-1766 (Apr. 2010).
Hirayama, Y., "Handbook for organic compound crystal—Principle and know-how," 2008, 28 pages.
"History of Changes for Study: NCT02690558. Phase 2 Study Of Pembrolizumab In Combination With Gemcitabine And Cisplatin As Neoadjuvant Therapy," NCT02690558, Mar. 10, Mar. 2017, Retrieved from the Internet: URL:https://clinicaltrials.gov/ct2/history/NCT02690558?V_4=View#StudyPageTop, 5 pages.
Howington, J. A. et al., "Treatment of Stage I and II Non-small Cell Lung Cancer," Diagnosis and Management of Lung Cancer, 3rd ed: American College of Chest Physicians Evidence-Based Clinical Practice Guidelines, Chest 2013; 143(5)(Suppl):e278S-e313S.
Humphries, L. A. et al., "Tec Kinases Mediate Sustained Calcium Influx via Site-specific Tyrosine Phosphorylation of the Phospholipase C Src Homology 2-Src Homology 3 Linker," J. Biol.Chem. 279(36):37651-37661 (2004).
International Preliminary Report on Patentability for International Application No. PCT/CN2011/085146, dated Jul. 1, 2014, 6 pages.
International Search Report and Written Opinion for International Application No. PCT/CN2011/085146, dated Sep. 27, 2012, 10 pages.
International Search Report and Written Opinion for International Application No. PCT/CN2013/083467, dated Jun. 16, 2014, 9 pages.
International Search Report and Written Opinion for International Application No. PCT/CN2014/075943, dated Jul. 18, 2014, 10 pages.
International Search Report and Written Opinion for International Application No. PCT/CN2015/083066, dated Sep. 24, 2015, 8 pages.
International Search Report and Written Opinion for International Application No. PCT/CN2016/079251, dated Jul. 21, 2016, 8 pages.
International Search Report and Written Opinion for International Application No. PCT/CN2017/098023, dated Nov. 16, 2017, 10 pages.
International Search Report and Written Opinion for International Application No. PCT/CN2018/074108, dated Apr. 23, 2018, 12 pages.
International Search Report and Written Opinion for International Application No. PCT/CN2018/092827, dated Sep. 29, 2018, 14 pages.
International Search Report and Written Opinion for International Application No. PCT/CN2018/100145, dated Nov. 14, 2018, 8 pages.
International Search Report and Written Opinion for International Application No. PCT/IB2017/053521, dated Jan. 11, 2018, 14 pages.
International Search Report and Written Opinion for International Application No. PCT/IB2017/054955, dated Sep. 10, 2018, 16 pages.
International Search Report and Written Opinion for International Application No. PCT/US2018/063068, dated Feb. 27, 2019, 7 pages.
International Search Report for International Application No. PCT/US2019/017313, dated Jun. 25, 2019, 16 pages.
InvivoGen Insight, "IgG-Fc Engineering For Therapeutic Use," Apr./May 2006, 4 pages.
James, L. K. et al., "Potential Mechanisms for IgG4 Inhibition of Immediate Hypersensitivity Reactions," Curr Allergy Asthma Rep. 2016; 16: 23. Published online Feb. 18, 2016. doi: 10.1007/s11882-016-0600-2.
Jenkins, S. M. et al., "Substituent variation in azabicyclic triazole- and tetrazole-based muscarinic receptor ligands," J. Med. Chem., 35(13):2392-2406 (1992).
Jett, J. R. et al., "Treatment of Small Cell Lung Cancer," Diagnosis and Management of Lung Cancer, 3rd ed: American College of Chest Physicians Evidence-Based Clinical Practice Guidelines, Chest 2013; 143(5)(Suppl):e400S-e419S.
Jiao, Y. et al., "Advances in the research of the anti-cancer agent—Raf kinase inhibitor," Strait Pharmaceutical Journal, vol. 19, No. 8, 2007, pp. 1-5 (with English Abstract).
Jie, L., "Deuterated Drugs Progress," Chemical Engineering Design Communication Medicine and Chemical Industry, 2016, vol. 42 (4), pp. 199.
Johnson, J. et al., "Relationships between drug activity in NCI preclinical in vitro and in vivo models and early clinical trials," British Journal of Cancer (2001) 84(10):1424-1431.
Jordan, V. C., "Tamoxifen: A most unlikely pioneering medicine," Nature Reviews: Drug Discovery, 2:205-213 (2003).
Kabat, E. A. et al., "Sequences of Proteins of Immunological Interest," vol. 1, Fifth Edition, U.S. Department of Health and Human Services, Public Health Service National Institutes of Health (1991), 152 pages.
Kabat, E. A. et al., "Unusual distributions of amino acids in complementarity-determining (hypervariable) segments of heavy

(56) References Cited

OTHER PUBLICATIONS and light chains of immunoglobulins and their possible roles in specificity of antibody-combining sites," J. Biol. Chem., Oct. 10, 1977;252(19):6609-6616.
Kabat, E. A., "The structural basis of antibody complementarity," Adv. Prot. Chem., 32:1-75 (1978).
Kebebew, "The Prevalence and Prognostic Value of BRAF Mutation in Thyroid Cancer," Ann. Surg., 2007; 246:466-471.
Kersseboom, R. et al., "Constitutive activation of Bruton's tyrosine kinaseinduces the formation of autoreactive IgM plasma cells," Eur. J. Immunol. 40:2643-2654, 2010.
Khan et al., "Cross-neutralizing anti-HIV-1 human single chain variable fragments (scFvs) against CD4 binding site and N332 glycan identified from a recombinant phage library." Scientific Reports (2017); Article No. 45163, 12 pages.
Khan, W. N., "Regulation of B lymphocyte development and activation by Bruton's tyrosine kinase," Immunol. Res., 23(2/3):147-156 (2001).
Khire, U. R. et al., "Omega-carboxypyridyl substituted ureas as Raf kinase inhibitors: SAR of the amide substituent," Bioorganic & Medicinal Chemistry Letters 14 (2004) 783-786.
Kim, K.-H. et al., "Imidazo[1,5-a]quinoxalines as irreversible BTK inhibitors for the treatment of rheumatoid arthritis," Bioorg. Med. Chem. Lett., 21:6258-6263 (2011).
Konishi, J. et al., "B7-H1 expression on non-small cell lung cancer cells and its relationship withtumor-infiltrating lymphocytes and their PD-1 expression," Clin Cancer Res. 10:5094-5100 (2004).
Konitzer et al., "Generation of a highly diverse panel of antagonistic chicken monoclonal antibodies against the GIP receptor," mABs (Apr. 2017); 9(3):536-549. Epub Jan. 5, 2017.
Kudo, M., Immune Checkpoint Blockade in Hepatocellular Carcinoma: 2017 Update, Liver Cancer, Nov. 2016; 6(1):1-12.
Kudo, M., "Immune Checkpoint Inhibition in Hepatocellular Carcinoma: Basics and Ongoing Clinical Trials," Oncology, 2017;92 Suppl 1:50-62. doi: 10.1159/000451016. Epub Feb. 2, 2017.
Labenz, J., "The epidemiology, diagnosis and treatment of Barrett's carcinoma," Dtsch Arztebllnt, 2015; 112:224-234.
Ledford, H., "US cancer institute overhauls cell lines," Nature, Feb. 25, 2016, vol. 530, p. 391.
Lee et al., "Molecular-level analysis of the serum antibody repertoire in young adults before and after seasonal influenza vaccination." Nat Med. (Dec. 2016); 22(12):1456-1464. Epub Nov. 7, 2016.
Li, N. et al., "BGB-3111 is a novel and highly selective Bruton's tyrosine kinase (BTK) inhibitor," Cancer Center, vol. 75, Supp. 1, Abstract No. 2597, 106th Annual Meeting of the American Association for Cancer Research, AACR 2015, Philadelphia, PA, United States, Apr. 2015.
Lou, Y. et al., "Bruton's tyrosine kinase inhibitors: Approaches to potent and selective inhibition, preclinical and clinical evaluation for inflammatory diseases and B cell malignancies," J. Med. Chem., 55(10):4539-4550 (2012).
Lowinger, T. B. et al., "Design and Discovery of Small Molecules Targeting Raf-1 Kinase," Current Pharmaceutical Design, (2002), 8:2269-2278.
Lund, J. et al., "Multiple interactions of IgG with its core oligosaccharide can modulate recognition by complement and human Fc gamma receptor I and influence the synthesis of its oligosaccharide chains," J Immunol., Dec. 1, 1996, 157(11):4963-4969.
Luo, J. et al., "Modern Physical Pharmaceutics Theory and Practice," Shang Hai Science and Technology Literature Publishing House, Apr. 2005, pp. 293-295.
Martin-Liberal, J. et al., "New RAF kinase inhibitors in cancer therapy," Expert Opinion on Pharmacotherapy, (2014) 15(9):1235-1245.
Mohamed, A. J. et al., "Bruton's tyrosine kinase (Btk): function, regulation, and transformation with special emphasis on the PH domain," Immunol. Rev., 228:58-73 (2009).
Nomi, T. et al., "Clinical significance and therapeutic potential of the programmed death-1 ligand/programmed death-1 pathway in human pancreatic cancer," Clin Cancer Res. 13(7):2151-2157 (Apr. 2007).
Ocana, A. et al., "Preclinical development of molecular targeted agents for cancer," Nat. Rev. Clin. Oncol., (2011) 8:200-209.
Ohigashi, Y. et al., "Clinical significance of programmed death-1 ligand-1 and programmed death-1 ligand-2 expression in human esophageal cancer," Clin Cancer Res., 11(8):2947-2953 (Apr. 2005).
Pan, Z, "Bruton's tyrosine kinase as a drug discovery target," Drug News Perspect, 21 (7):357-362 (2008).
Panka, D. J. et al., "Variable region framework differences result in decreased or increased affinity of variant anti-digoxin antibodies," May 1988, Proc. Natl. Acad. Sci. USA, 85:3080-3084.
Parola et al., "Integrating high-throughput screening and sequencing for monoclonal antibody discovery and engineering." Immunology (Jan. 2018); 153(1):31-41. Epub Oct. 30, 2017.
Paul, W. E. (Ed.), Chap. 9, Structure and Function of Immunoglobulins, In: Fundamental Immunology, Third Edition, pp. 292-295, 1993.
Plimack, E. R. et al., "Pembrolizumab (MK-3475) for advanced urothelial cancer: Updated results and biomarker analysis from KEYNOTE-012," J. Clin. Oncol., vol. 33, Issue 15 Suppl., May 2015, Abstract 4502, 2 pages.
Presta, L. G. et al., "Engineering therapeutic antibodies for improved function," Biochemical Society Transactions (2002) vol. 30, Part 4, pp. 487-490.
Raphael, "Identifying driver mutations in sequenced cancer genomes: computational approaches to enable precision medicine," Genome Medicine, 2014; 6(5):1-17.
Riley, J. L., "PD-1 signaling in primary T cells," Immunological Reviews, 229:114-125 (2009).
Rokosz, L. L. et al., "Kinase inhibitors as drugs for chronic inflammatory and immunological diseases: progress and challenges," Expert Opin. Ther. Targets, 12(7):883-903 (2008).
Rudikoff, S. et al., "Single amino acid substitution altering antigen-binding specificity," Proc. Natl. Acad. Sci. USA, 79:1979-1983 (Mar. 1982).
Sale, "Models of ovarian cancer metastasis: Murine models," Drug Discovery Today, Disease Models, 2006;3:150-154.
Samonakis, D. N. et al., "Systemic treatment for hepatocellular carcinoma: Still unmet expectations," World J Hepatol., Jan. 2017; 9(2):80-90.
Sanz-Garcia, E. et al., "Current and advancing treatments for metastatic colorectal cancer," Expert Opinion on Biological Therapy, 16(1):93-110 (2016).
Schober, "New Advances in the Treatment of Metastatic Pancreatic Cancer," Digestion, 2015;92:175-184.
Sequence Alignment, 2014, 1 page.
Sharma, P. et al., "Efficacy and safety of nivolumab monotherapy in metastatic urothelial cancer (mUC): Results from the phase I/II CheckMate 032 study," J. Clin. Oncol., vol. 34, No. 15 Suppl., May 2016, pp. 4501.
Sharma, P. et al., "Nivolumab monotherapy in recurrent metastatic urothelial carcinoma (CheckMate 032): a multicentre, open-label, two-stage, multi-arm, phase 1/2 trial," Lancet Oncol., Nov. 2016, vol. 17, No. 11, pp. 1590-1598.
Sharma, S. V. et al., "Cell line-based platforms to evaluate the therapeutic efficacy of candidate anticancer agents," Nature Reviews Cancer (Apr. 2010), 10:241-253.
Sheehan et al., "Phage and Yeast Display." Microbial. Spectr. (2015); 3(1):AID-0028-2014; 17 pages.
Shi, F. et al., "PD-1 and PD-L1 upregulation promotes CD8(+) T-cell apoptosis and postoperative recurrence in hepatocellular carcinoma patients," Int. J. Cancer 128(4):887-896 (Feb. 2011).
Shields, R. L. et al., "High Resolution Mapping of the Binding Site on Human IgG1 for FcRI, FcRII, FcRI 11, and FcRn and Design of IgG 1 Variants with Improved Binding to the FcR," The Journal of Biological Chemistry, 276(9):6591-6604 (2001).
Shioji, Y., "Production Technology of Solid Preparations," Tokyo, CMC Publication, Jan. 27, 2003, Popular Edition, pp. 9 and 12-13.

(56) References Cited

OTHER PUBLICATIONS

Simone, J. V., Part XIV Oncology, 154 Introduction, In: Cecil Textbook of Medicine, 20th Edition, vol. 1, Bennett, J. C. (ed.) (1996) pp. 1004-1010.
Singhal, D. et al., "Drug polymorphism and dosage form design: a practical perspective," Advanced Drug Delivery Reviews, 56 (2004) pp. 335-347.
Smith, C. I. E. et al., "Expression of Bruton's Agammaglobulinemia Tyrosine Kinase Gene, BTK, Is Selectively Down-Regulated in T Lymphocytes and Plasma Cells," J. Immunol., 152:557-565 (1994).
Smith, K. G. et al., "FcRIIB in autoimmunity and infection: evolutionary and therapeutic implications," Nat Rev Immunol. May 2010;10(5):328-43.
Socinski, M. A. et al., "Treatment of Stage IV Non-small Cell Lung Cancer," Diagnosis and Management of Lung Cancer, 3rd ed: AmericanCollege of Chest Physicians Evidence-Based Clinical Practice Guideline, Chest 2013; 143(5)(Suppl):e341 S-e368S.
Stave, J. W. et al., "Antibody and antigen contact residues define epitope and paratope size and structure," The Journal of Immunology, vol. 191, Jan. 2013, pp. 1428-1435.
Strome, S. E. et al., "A Mechanistic Perspective of Monoclonal Antibodies in Cancer Therapy Beyond Target-Related Effects," The Oncologist, 2007; 12:1084-1095.
Supplementary Partial European Search Report for European Application No. 13893636.4, dated Feb. 28, 2017, 13 pages.
Sznol, M. et al., "Antagonist antibodies to PD-1 and B7-H1 (PD-L1) in the treatment of advanced human cancer," Clinical Cancer Research, 19(5):1021-1034 (Mar. 2013).
Takada, N., "Bulk Drug Form Screening and Selection at Drug Discovery Phase," Pharm Stage, Jan. 15, 2007 Vol. 6, No. 10, pp. 20-25.
Takayama, T. et al., "Effects of the novel and potent lymphocyte-specific protein tyrosine kinase inhibitor TKM0150 on mixed lymphocyte reaction and contact hypersensitivity in mice," Arzneimittelforschung, 60(5):282-285 (2010).
Takayama, T. et al., "Ring-fused pyrazole derivatives as potent inhibitors of lymphocytespecific kinase (Lck): Structure, synthesis, and SAR," Bioorganic & Medicinal Chemistry Letters, 20(1):112-116 (Jan. 2010).
Tang, Z. et al., "BGB-283, a novel RAF kinase and EGFR inhibitor, displays potent antitumor activity in BRAF-mutated colorectal cancers," Molecular Cancer Therapeutics, 2015, vol. 14, No. 10, pp. 2187-2197.
Thompson, R. H. et al., "Costimulatory B7-H1 in renal cell carcinoma patients: Indicator of tumor aggressiveness and potential therapeutic target," Proc Natl Acad Sci 101(49):17174-17179 (Dec. 2004).
Thompson, R. H. et al., "EDPD-1 is expressed by tumor-infiltrating immune cells and is associated with poor outcome for patients with renal cell carcinoma," Clin. Cancer Res. 13(6):1757-1761 (2007).
Topalian, S. L., "Safety, Activity, and Immune Correlates of Anti-PD-1 Antibody in Cancer," N. Engl. J. Med., Jun. 2012; vol. 366, No. 26, pp. 2443-2454.
Uckun, F. M. et al., "Bruton's tyrosine kinase as a new therapeutic target," Anti-Cancer Agents in Medicinal Chemistry, 7(6):624-632 (2007).
Van Regenmortel, M. H. V., "Development of a Preventive HIV Vaccine Requires Solving Inverse Problems Which Is Unattainable by Rational Vaccine Design." Front Immunol. (Jan. 2018); 8: 2009. eCollection 2017.

Vetrie, D. et al., "The gene involved in X-linked agammaglobulinaemia is a member of the src family of protein-tyrosine kinases," Nature, 361:226-233 (1993).
Vibhakar, R. et al., "Activation-Induced Expression of Human Programmed Death-1 Gene in T-Lymphocytes," Exp. Cell Res., vol. 232, Issue 1, Apr. 1997, pp. 25-28.
Wang, C. et al., "In Vitro Characterization of the Anti-PD-1 Antibody Nivolumab, BMS-936558, and In Vivo Toxicology in Non-Human Primates," Cancer Immunol Res; 2(9):846-856 (Sep. 2014).
Wherry, E. J., "T cell exhaustion," Nature Immunology 12(6):492-499 (2011). Published online May 18, 2011.
Wilson, W. H. et al., "686—The Bruton's Tyrosine Kinase (Btk) Inhibitor, Ibrutinib (PCI-32765), Has Preferential Activity in the ABC Subtype of Relapsed/Refractory De Novo Diffuse Large B-Cell Lymphoma (DLBCL): Interim Results of a Multicenter, Open-Label, Phase2 Study," Poster #686, 54th American Society of Hematology (ASH) annual meeting abstract (Dec. 10, 2012).
Wu, C. et al., "Immunohistochemical localization of programmed death-1 ligand-1 (PD-L1) in gastric carcinoma and its clinical significance," Acta Histochem., 108(1):19-24 (2006).
Wu, H. et al., "Humanization of a murine monoclonal antibody by simultaneous optimization of framework and CDR residues," Journal of Molecular Biology, 294(1):151-162 (Nov. 1999).
Xu, D. et al., "In vitro characterization of five humanized OKT3 effector function variant antibodies," Cell Immunol. Feb. 25, 2000;200(1):16-26.
Yoo, S. et al., "New drugs in prostate cancer," Prostate International, 4 (2016) 37-42.
Zambon, A. et al., "Small molecule inhibitors of BRAF in clinical trials," Bioorganic & Medicinal Chemistry Letters, 22 (2012) 789-792.
Zhang, L. et al., "PD-1/PD-L1 interactions inhibit antitumor immune responses in a murine acute myeloid leukemia model," Blood, 114(8):1545-1552 (Aug. 2009).
Zheng, "Clinical detection and categorization of uncommon and concomitant mutations involving BRAF," BMC Cancer, 2015; 15:779.
Zhou et al., "Structural Repertoire of HIV-1-Neutralizing Antibodies Targeting the CD4 Supersite in 14 Donors." Cell (Jun. 2015); 161(6):1280-1292.
Blumenschein, G. R., Jr. et al., "A randomized phase II study of the MEK1/MEK2 inhibitor trametinib (GSK1120212) compared with docetaxel in KRAS-mutant advanced non-small-cell lung cancer (NSCLC)," Ann Oncol., May 2015;26(5):894-901. doi: 10.1093/annonc/mdv072. Epub Feb. 26, 2015.
Li, N. et al., "BGB-3111 is a novel and highly selective Bruton's tyrosine kinase (BTK) inhibitor," Cancer Center, vol. 75, No. 15, Supp. 1, Abstract No. 2597, 106th Annual Meeting of the American Association for Cancer Research, AACR 2015, Philadelphia, PA, United States, Aug. 2015, 2 pages.
MedChemExpress, "Zanubrutinib," Product Data Sheet, Retrieved from the Internet: www.medchemexpress.com, Retrieved Aug. 17, 2021, 2 pages.
Otsuka, J. et al., "K-ras mutation may promote carcinogenesis of endometriosis leading to ovarian clear cell carcinoma," Medical Electron Microscopy, vol. 37, pp. 188-192 (2004).
Philips, G. K. et al., "Therapeutic uses of anti-PD-1 and anti-PD-L1 antibodies," International Immunology, vol. 27, No. 1, Oct. 2014, pp. 39-46.

\* cited by examiner

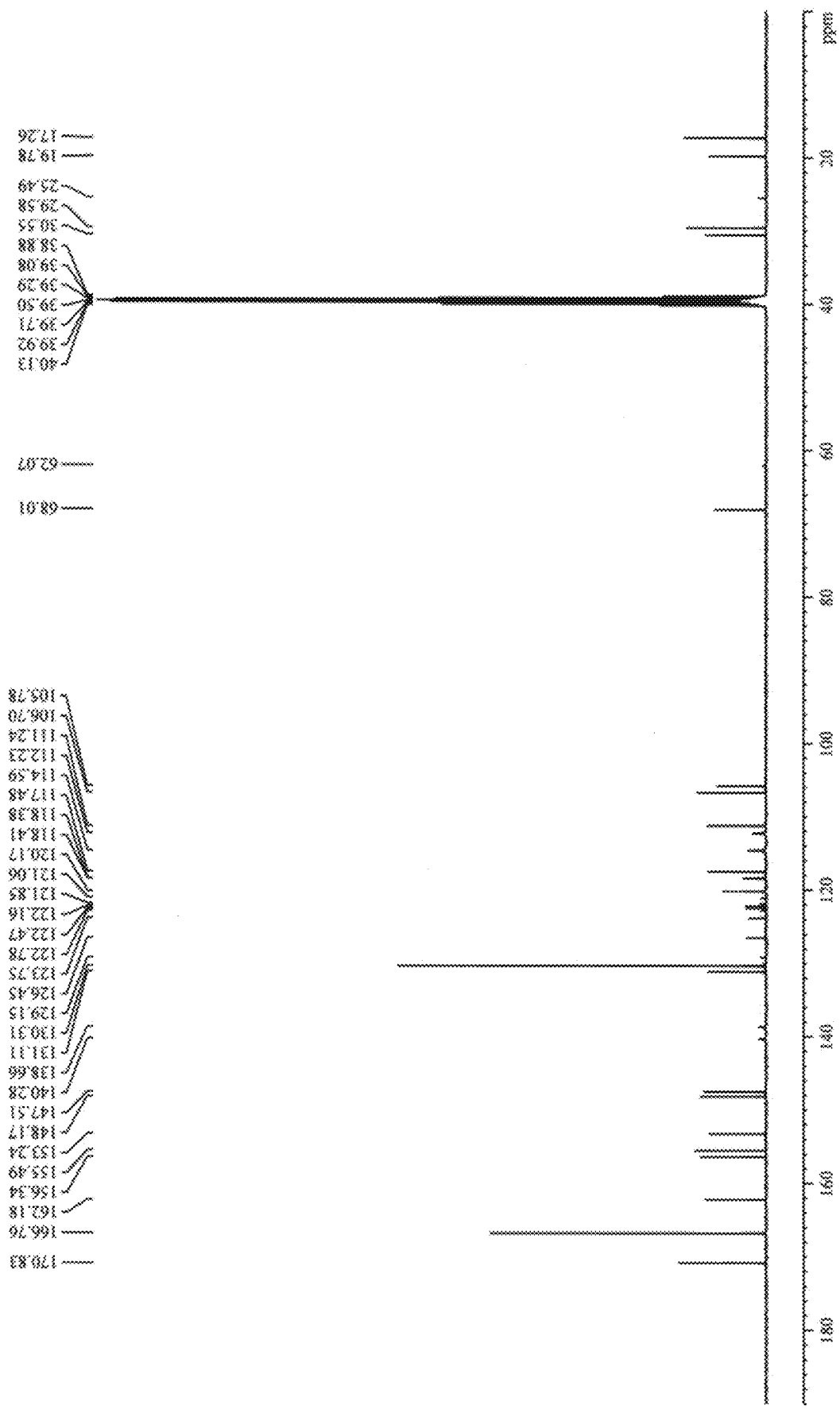

COMBINATION OF A PD-1 ANTAGONIST AND A RAF INHIBITOR FOR TREATING CANCER

CROSS-REFERENCE TO RELATED APPLICATIONS

This application is a continuation of U.S. patent application Ser. No. 16/315,539, filed on Jan. 4, 2019, now U.S. Pat. No. 10,864,203, which is a U.S. National Stage Application under 35 U.S.C. § 371 of International Application No. PCT/IB2017/053521, filed Jun. 14, 2017, which claims the benefit of priority to International Application No. PCT/CN2016/088591, filed on Jul. 5, 2016, the disclosures of which are incorporated herein by reference in their entireties for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: BEIG_015_02US_SeqList.txt, date recorded Apr. 5, 2021, file size 78 kilobytes).

FIELD OF THE INVENTION

Disclosed herein is a pharmaceutical combination for use in the prevention, delay of progression or treatment of cancer, wherein the pharmaceutical combination exhibits a synergistic efficacy. The pharmaceutical combination comprises a humanized antagonist monoclonal antibody against PD-1 and a RAF inhibitor. Also disclosed herein is a method for use in the prevention, delay of progression or treatment of cancer in a subject, comprising administering to the subject a therapeutically effective amount of a humanized antagonist monoclonal antibody against PD-1 and a therapeutically effective amount of a RAF inhibitor.

BACKGROUND OF THE INVENTION

Mitogen-activated protein kinase (MAPK) signaling pathway which consists of RAS-RAF-MEK-ERK kinase cascade is one of the critical signal transduction pathways in regulating diverse cellular activities, such as cell survival, growth, differentiation and proliferation. Genetic aberrations that lead to constitutive activation of the MAPK pathway are commonly observed in human cancers. Oncogenic B-Raf mutations, with V600E mutation accounting for at least 90%, have been detected in a variety of human malignancies. Inhibitors that selectively target mutated B-Raf such as vemurafenib and dabrafenib have achieved high response rate and been approved by FDA in treating melanoma patients harboring B-Raf$^{V600E}$. Prior studies suggested that B-Raf-targeting therapies could increase antigen expression, decrease immune suppressive factors in tumor microenvironment, and improve homing of T effector cells to the tumors. Thus, selective B-Raf inhibitors were suggested to possess immunosensitization properties and could be used in combination with immunotherapies to achieve more durable disease control/response in treating cancer.

Programmed Death 1 protein (PD-1, Pdcd-1, or CD279) is a 55 KD receptor protein related to CD28/CTLA4 co-stimulatory/inhibitory receptor family (Blank et al., 2005 *Cancer Immunol Immunother* 54:307-314). The full length PD-1 contains 288 amino acid residues (NCBI accession number: NP_005009). Its extracellular domain consists of amino acid residues 1-167, and the cytoplasmic C-terminal tail comprises residues 191-288, which has two hypothetical immune-regulatory motifs, an immunoreceptor tyrosine-based inhibitory motif (ITIM; Vivier et al., 1997 *Immunol Today* 18:286-291) and an immunoreceptor tyrosine switch motif (ITSM; Chemnitz et al, 2004 *J Immunol* 173:945-954).

Two sequence-related ligands, PD-L1 (B7-H1) and PD-L2 (B7-DC), have been identified to specifically interact with PD-1, inducing intracellular signal transduction that inhibits CD3 and CD28 mediated T-cell activation (Riley, 2009 *Immunol Rev* 229: 114-125), which, in turn, attenuates T-cell activities, for example, reduction of cell proliferation, IL-2 and IFN-γ secretion, as well as other growth factor and cytokine secretion.

Expression of PD-1 was frequently found in immune cells such as T-cells, B-cells, monocytes and natural killer (NK) cells. It was rarely expressed in other human tissues, such as muscle, epithelium, neuronal tissues, etc. Furthermore, high level of PD-1 expression is often associated with activation of immune cells. For example, when human T-cell line, Jurkat, was activated by phytohaemagglutinin (PHA) or phorbol ester (12-0-tetradecanoylphorbol-13-acetate, or TP A), the expression of PD-1 was up-regulated visible in Western Blot (Vibharka et al., 1997 *Exp Cell Res* 232:25-28). The same phenomenon was observed in stimulated murine T- and B-lymphocytes and in primary human CD4$^+$ T-cells upon stimulation by anti-CD3 antibody (Agata et al., 1996 *Int Immunol* 8:765-772; Bennett et al., 2003 *J Immunol* 170:711-118). The increase of PD-1 expression following stimulation of T effector cells redirects the activated T-effector cells towards exhaustion and reduced immune activities. Therefore, PD-1 mediated inhibitory signal plays an important role in immune tolerance (Bour-Jordan et al., 2011 *Immunol Rev* 241:180-205).

Increase of PD-1 expression in tumor-infiltrating lymphocytes (TILs) and PD-1 ligand expression in tumor cells were reported in varieties of cancers involved in different types of tissues and organs such as lung (Konishi et al., 2004 *Clin Cancer Res* 10:5094-5100), liver (Shi et al, 2008 *Int J Cancer* 128:887-896; Gao et al, 2009 *Clin Cancer Res* 15:971-979), stomach (Wu et al, 2006 *Acta Histochem* 108: 19-24), kidney (Thompson et al, 2004 *Proc Natl Acad Sci* 101: 17174-17179; Thompson et al, 2007 *Clin Cancer Res* 13: 1757-1761), breast (Ghebeh et al., 2006 *Neoplasia* 8: 190-198), ovary (Hamanishi et al. 2007 *Proc Natl Acad Sci* 104:3360-3365), pancreas (Nomi et al, 2007 *Clin Cancer Res* 13:2151-2157), melanocytes (Hino et al., 2010 *Cancer* 116: 1757-1766) and esophagus (Ohigashi et al., 2005 *Clin Cancer Res* 11:2947-2953). More frequently, the increased expression of PD-1 and PD-L1 in those cancers is associated with poor prognosis of patient survival outcome. Transgenic mice with PD-1 gene knockout inhibiting xenograft cancer cell growth further elucidated the significance of PD-1 signaling in the modulation of immune system for cancer eradication or tolerance (Zhang et al., 2009 *Blood* 114: 1545-1552).

WO 2013/097224 A1 disclosed a second generation B-RAF inhibitor, which has demonstrated potent inhibitory activity against RAF family of serine/threonine kinases.

PCT application PCT/CN2016/079251 discloses pharmaceutically-acceptable salt of the second generation B-RAF inhibitors in WO 2013/097224 A1, particularly, 5-(((1R,1aS, 6bR)-1-(6-(trifluoromethyl)-1H-benzo[d]imidazol-2-yl)-1a, 6b-dihydro-1H-cyclopropa[b]benzofuran-5-yl)oxy)-3,4-dihydro-1,8-naphthyrdin-2(1H)-one Sesqui-Maleate (hereinafter Compound 1) for the treatment of cancers with aberrations in the RAF-MEK-ERK MAPK pathway including B-Raf mutations, K-Ras/N-Ras mutations and NF1 mutations, which has potent and reversible inhibitory activities against RAF family kinases including A-Raf, B-Raf, C-Raf and B-Raf$^{V600E}$.

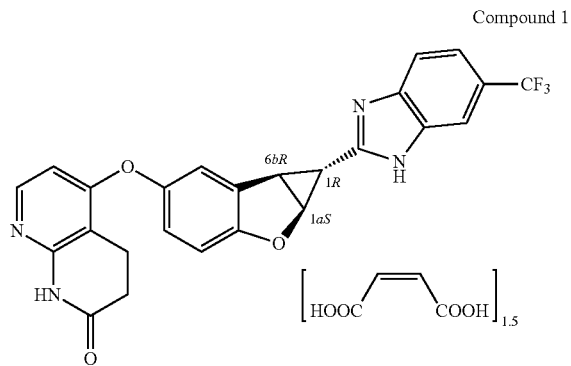

Compound 1

WO 2015/035606 A1 disclosed a monoclonal antibody comprising a heavy chain variable region (Vh) and a light chain variable region (Vk) (comprising SEQ ID No 24 and SEQ ID No 26, respectively) and a IgG4 heavy chain effector or constant domain (comprising SEQ ID NOs: 88), hereinafter Mab 1, which specifically binds to PD-1, especially PD-1 residues including K45 and 193; or, 193, L95 and P97, and inhibits PD-1-medidated cellular signaling and activities in immune cells, antibodies binding to a set of amino acid residues required for its ligand binding.

The inventors of the present application have found that the combination of the above Anti-PD1 Antibodies (i.e., Mab 1) and antibody fragments thereof with the selective B-Raf inhibitor (i.e., Compound 1) surprisingly and unexpectedly augments T cell responses in a subject suffering from cancer associated with K-Ras mutations by enhancing IFN-γ production. In particular, the inventors of the present application have unexpectedly found that the combination of the particular Anti-PD1 Antibodies (i.e., Mab 1) and the particular selective B-Raf inhibitor (i.e., Compound 1) resulted in synergistic inhibition of tumor growth in cancers associated with K-Ras mutations as compared with the monotherapy of the Anti-PD1 Antibodies or the B-Raf inhibitor alone.

SUMMARY OF THE INVENTION

In a first aspect, disclosed herein is a pharmaceutical combination for use in the prevention, delay of progression or treatment of cancer, comprising a humanized antagonist monoclonal antibody against PD-1 and a RAF inhibitor. The pharmaceutical combination produces synergistic efficacy in inhibiting tumor growth in cancer.

In a second aspect, disclosed herein is a method for the prevention, delay of progression or treatment of cancer in a subject, comprising administering to the subject in need thereof a therapeutically effective amount of a humanized antagonist monoclonal antibody against PD-1 and a therapeutically effective amount of a RAF inhibitor.

In a third aspect, disclosed herein is a humanized antagonist monoclonal antibody against PD-1 for use in the prevention, delay of progression or treatment of cancer in combination with a RAF inhibitor. In one embodiment of this aspect, disclosed herein is a RAF inhibitor for use in the prevention, delay of progression or treatment of cancer in combination with a humanized antagonist monoclonal antibody against PD-1.

In a fourth aspect, disclosed herein is a use of a pharmaceutical combination in the manufacture of a medicament for use in the prevention, delay of progression or treatment of cancer, said pharmaceutical combination comprising a humanized antagonist monoclonal antibody against PD-1 and a RAF inhibitor.

In a fifth aspect, disclosed herein is an article of manufacture, or "kit" comprising a first container, a second container and a package insert, wherein the first container comprises at least one dose of a medicament comprising a PD-1 antagonist, the second container comprises at least one dose of a medicament comprising a RAF inhibitor, and the package insert comprises instructions for treating cancer a subject using the medicaments.

BRIEF DESCRIPTION OF THE DRAWINGS

FIG. 6 shows a $^{13}$C-NMR spectrum of the crystalline form of Compound 1.

DETAILED DESCRIPTION OF THE INVENTION

Abbreviations

Figure 1:
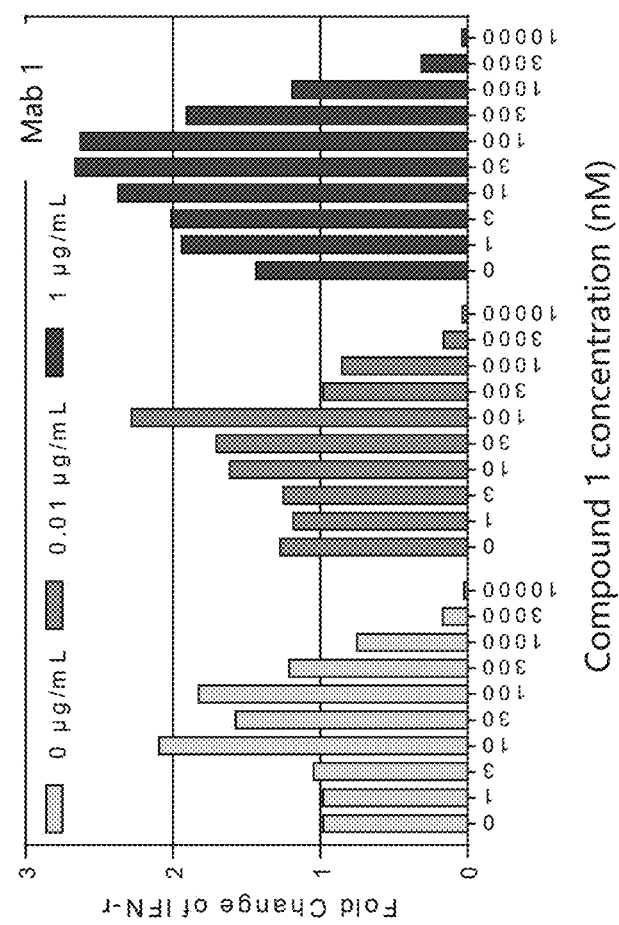
FIG. 1 shows the level of IFN-γ produced from activated PBMC in tumor spheriod/PBMC co-culture system after treatment with RAF inhibitor alone or combination of RAF inhibitor and anti-PD-1 mAb.

Throughout the detailed description and examples disclosed herein, the following abbreviations will be used:

| | |
|---|---|
| CDR | Complementarity determining region |
| DPBS | Dulbecco's Phosphate Buffered Saline |
| DMEM | Dulbecco minimum essential medium |
| IgG | immunoglobulin G |
| i.p. | Intraperitoneal or Intraperitoneally |
| i.v. | intravenous or intravenously |
| IFN-γ | Interferon-γ |
| mAb | Monoclonal antibodies |
| MAPK | Mitogen-activated protein kinase |
| NK | Natural killer |
| PD-1 | Programmed Death 1 protein, Pdcd-1, or CD279 |
| PBMC | Peripheral blood mononuclear cell |
| PDX | Patient-derived xenograft |
| PHA | Phytohaemagglutinin |
| p.o. | "by mouth" or "per os" |
| QD | Once daily |
| QW | Once weekly |
| Q2W | Once every two weeks |
| Q3W | Once every three weeks |
| Q4W | Once every four weeks |
| TILs | Tumor-infiltrating lymphocytes |
| Vh | Heavy chain variable region |
| Vk | Light chain variable region |

Definitions

Unless specifically defined elsewhere in this document, all other technical and scientific terms used herein have the meaning commonly understood by one of ordinary skill in the art to which this invention belongs.

As used herein, including the appended claims, the singular forms of words such as "a", "an", and "the", include their corresponding plural references unless the context clearly dictates otherwise.

The term "about" used in the context of quantitative measurements means the indicated amount±20%, or alternatively the indicated amount±10% or ±5% or ±1%. For example, for Compound 1, a molar ratio (free base/maleic acid, n) of about 1 may vary between 0.8 and 1.2.

The term "alkyl" herein means a monoradical branched or linear saturated hydrocarbon chain comprising from 1 to 18, such as from 1 to 12, further such as from 1 to 6, carbon atoms. Alkyl groups include, but not limited to, methyl, ethyl, n-propyl, iso-propyl, n-butyl, iso-butyl, t-butyl, n-hexyl, n-decyl, tetradecyl, and the like.

The term "alkenyl" herein means a monoradical branched or linear unsaturated hydrocarbon group comprising at least one C═C double bond and from 2 to 18, such as from 2 to 8, further such as from 2 to 6 carbon atoms. Alkenyl groups include, but not limited to, ethenyl (or vinyl, i.e. —CH═CH$_2$), 1-propylene (or allyl, i.e. —CH$_2$CH═CH$_2$), isopropylene (—C(CH$_3$)═CH$_2$), and the like.

The term "alkynyl" herein means a monoradical branched or linear unsaturated hydrocarbon group comprising at least one C≡C triple bond and from 2 to 18, such as from 2 to 8, further such as from 2 to 6 carbon atoms. Alkynyl groups include, but not limited to, ethynyl (—C≡CH), propargyl (or propynyl, i.e. —C≡CCH$_3$), and the like.

The term "cycloalkyl" herein means a cyclic alkyl group comprising from 3 to 20 carbon atoms, or from 3 to 10 carbon atoms, or from 3 to 8 carbon atoms or from 3 to 6 carbon atoms having a monocyclic ring or multiple condensed rings. A cycloalkyl group may be saturated and partially unsaturated. Examples of monocyclic saturated cycloalkyl groups include, but not limited to, $C_{3-8}$ cycloalkyl selected from the group consisting of cyclopropyl, cyclobutyl, cyclopentyl, cyclohexyl, cycloheptyl, and cyclooctyl. Examples of monocyclic partially unsaturated cycloalkyl groups include, but not limited to, cyclopent-1-enyl, 1-cyclopent-2-enyl, 1-cyclopent-3-enyl, 1-cyclohex-1-enyl, 1-cyclohex-2-enyl, 1-cyclohex-3-enyl, and cyclohexadienyl.

The term "aryl" herein means a monovalent aromatic hydrocarbon radical comprising from 6 to 20 carbon atoms, such as from 6 to 10 carbon atoms derived by the removal of one hydrogen atom from a single carbon atom of a parent aromatic ring system. Aryl includes bicyclic radicals comprising an aromatic ring fused to a saturated, partially unsaturated ring, or aromatic carbocyclic or heterocyclic ring. Examples of aryl groups include, but not limited to, radicals derived from benzene (phenyl), substituted benzenes, naphthalene, anthracene, biphenyl, indenyl, indanyl, 1,2-dihydronapthalene, 1,2,3,4-tetrahydronapthyl, and the like.

The term "halogen" or "halo" herein means F, Cl, Br or I.

The term "heteroaryl" herein means a group selected from:

5- to 7-membered aromatic, monocyclic rings comprising at least one heteroatom, for example, from 1 to 4, or, in some embodiments, from 1 to 3, heteroatoms, selected from N, O, and S, with the remaining ring atoms being carbon;

8- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and 11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

For example, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" herein means a ring selected from 4- to 12-membered monocyclic, bicyclic and tricyclic, saturated and partially unsaturated rings comprising at least one carbon atoms in addition to at least one heteroatom, such as from 1-4 heteroatoms, further such as from 1-3, or further such as 1 or 2 heteroatoms, selected from oxygen, sulfur, and nitrogen. "Heterocycle" herein also means a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl. "Heterocycle" herein also means an aliphatic spirocyclic ring comprising at least one heteroatom selected from N, O, and S, provided that the point of attachment is at the heterocyclic ring. The rings may be saturated or have at least one double bond (i.e., partially unsaturated). The heterocycle may be substituted with oxo. The point of the attachment may be carbon or heteroatom in the heterocyclic ring. A heterocycle is not a heteroaryl as defined herein.

Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-morpholinyl, oxiranyl, aziridinyl, thiiranyl, azetidinyl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. A substituted heterocycle also includes a ring system substituted with one or more oxo moieties, such as piperidinyl N-oxide, morpholinyl-N-oxide, 1-oxo-1-thiomorpholinyl and 1,1-dioxo-1-thiomorpholinyl.

The term "fused ring" herein means a polycyclic ring system, e.g., a bicyclic or tricyclic ring system, in which two rings share only two ring atoms and one bond in common. Examples of fused rings may comprise a fused bicyclic cycloalkyl ring such as those having from 7 to 12 ring atoms arranged as a bicyclic ring selected from [4,4], [4,5], [5,5], [5,6] and [6,6] ring systems as mentioned above; a fused bicyclic aryl ring such as 7 to 12 membered bicyclic aryl ring systems as mentioned above, a fused tricyclic aryl ring such as 10 to 15 membered tricyclic aryl ring systems mentioned above; a fused bicyclic heteroaryl ring such as 8- to 12-membered bicyclic heteroaryl rings as mentioned above, a fused tricyclic heteroaryl ring such as 11- to 14-membered tricyclic heteroaryl rings as mentioned above; and a fused bicyclic or tricyclic heterocyclyl ring as mentioned above.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. The term "administration" and "treatment" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, rabbit) and most preferably a human.

The term "pharmaceutically acceptable salt" herein includes, but not limited to salts with inorganic acids, selected, for example, from hydrochlorates, phosphates, diphosphates, hydrobromates, sulfates, sulfinates, and nitrates; as well as salts with organic acids, selected, for example, from malates, maleates, fumarates, tartrates, succinates, citrates, lactates, methanesulfonates, p-toluenesulfonates, 2-hydroxyethylsulfonates, benzoates, salicylates, stearates, alkanoates such as acetate, and salts with HOOC—$(CH_2)_n$—COOH, wherein n is selected from 0 to 4.

Similarly, examples of pharmaceutically acceptable cations include, but not limited to, sodium, potassium, calcium, aluminum, lithium, and ammonium.

The term "antibody" herein is used in the broadest sense and specifically covers antibodies (including full length monoclonal antibodies) and antibody fragments so long as they recognize PD-1. An antibody molecule is usually monospecific, but may also be described as idiospecific, heterospecific, or polyspecific. Antibody molecules bind by means of specific binding sites to specific antigenic determinants or epitopes on antigens. "Antibody fragments" comprise a portion of a full length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments.

The term "monoclonal antibody" or "mAb" or "Mab" herein means a population of substantially homogeneous antibodies, i.e., the antibody molecules comprised in the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. Monoclonal antibodies (mAbs) may be obtained by methods known to those skilled in the art. See, for example Kohler et al (1975); U.S. Pat. No. 4,376,110; Ausubel et al (1987-1999); Harlow et al (1988); and Colligan et al (1993). The mAbs disclosed herein may be of any immunoglobulin class including IgG, IgM, IgD, IgE, IgA, and any subclass thereof. A hybridoma producing a mAb may be cultivated in vitro or in vivo. High titers of mAbs can be obtained in in vivo production where cells from the individual hybridomas are injected intraperitoneally into mice, such as pristine-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art.

In general, the basic antibody structural unit comprises a tetramer. Each tetramer includes two identical pairs of polypeptide chains, each pair having one "light chain" (about 25 kDa) and one "heavy chain" (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as α, δ, ε, γ, or μ, and define the antibody's isotypes as IgA, IgD, IgE, IgG, and IgM, respectively. Within light and heavy chains, the variable and constant regions are joined by a "J" region of about 12 or more amino acids, with the heavy chain also including a "D" region of about 10 more amino acids.

The variable regions of each light/heavy chain (Vk/Vh) pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called "complementarity determining regions (CDRs)", which are located within relatively conserved framework regions (FR). The CDRs are usually aligned by the framework regions, enabling binding to a specific epitope. In general, from N-terminal to C-terminal, both light and heavy chains variable domains comprise FR-1, CDR-1, FR-2, CDR-2, FR-3, CDR-3, and FR-4. The assignment of amino acids to each domain is, generally, in accordance with the definitions of Sequences of Proteins of Immunological Interest, Kabat, et al. *National Institutes of Health*, Bethesda, Md.; 5<m>ed.; NIH Publ. No. 91-3242 (1991); Kabat (1978) *Adv. Prot. Chem.* 32: 1-75; Kabat, et al., (1977) *J. Biol. Chem.* 252:6609-6616; Chothia, et al, (1987) *J Mol. Biol.* 196:901-917 or Chothia, et al, (1989) *Nature* 342:878-883.

The term "hypervariable region" means the amino acid residues of an antibody that are responsible for antigen-binding. The hypervariable region comprises amino acid residues from a "complementarity determining region" or "CDR" (i.e., CDR-L1, CDR-L2 and CDR-L3 in the light chain variable domain and CDR-H1, CDR-H2 and CDR-H3 in the heavy chain variable domain). See, Kabat et al. (1991) *Sequences of Proteins of Immunological Interest, 5th Ed. Public Health Service, National Institutes of Health*, Bethesda, Md. (defining the CDR regions of an antibody by sequence); see also Chothia and Lesk (1987) *J. Mol. Biol.* 196: 901-917 (defining the CDR regions of an antibody by structure). The term "framework" or "FR" residues means those variable domain residues other than the hypervariable region residues defined herein as CDR residues.

Unless otherwise indicated, "antibody fragment" or "antigen binding fragment" means antigen binding fragments of antibodies, i.e. antibody fragments that retain the ability to bind specifically to the antigen bound by the full-length antibody, e.g. fragments that retain one or more CDR regions. Examples of antibody binding fragments include, but not limited to, Fab, Fab', F(ab')$_2$, and Fv fragments; diabodies; linear antibodies; single-chain antibody molecules, e.g., sc-Fv; nanobodies and multispecific antibodies formed from antibody fragments.

An antibody that "specifically binds to" a specified target protein is an antibody that exhibits preferential binding to that target as compared to other proteins, but this specificity does not require absolute binding specificity. An antibody is considered "specific" for its intended target if its binding is determinative of the presence of the target protein in a sample, e.g. without producing undesired results such as false positives. Antibodies, or binding fragments thereof, useful in the present invention will bind to the target protein with an affinity that is at least two fold greater, preferably at least ten times greater, more preferably at least 20-times greater, and most preferably at least 100-times greater than the affinity with non-target proteins. An antibody herein is said to bind specifically to a polypeptide comprising a given amino acid sequence, e.g. the amino acid sequence of a mature human PD-1 molecule, if it binds to polypeptides comprising that sequence but does not bind to proteins lacking that sequence.

The term "human antibody" herein means an antibody that comprises human immunoglobulin protein sequences only. A human antibody may contain murine carbohydrate chains if produced in a mouse, in a mouse cell, or in a hybridoma derived from a mouse cell. Similarly, "mouse antibody" or "rat antibody" mean an antibody that comprises only mouse or rat immunoglobulin sequences, respectively.

The term "humanized antibody" means forms of antibodies that contain sequences from non-human (e.g., murine) antibodies as well as human antibodies. Such antibodies contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. The prefix "hum", "hu" or "h" is added to antibody clone designations when necessary to distinguish humanized antibodies from parental rodent antibodies. The humanized forms of rodent antibodies will generally comprise the same CDR sequences of the parental rodent antibodies, although certain amino acid substitutions may be included to increase affinity, increase stability of the humanized antibody, or for other reasons.

The terms "cancer" or "tumor" herein mean or describe the physiological condition in mammals that is typically characterized by unregulated cell growth. Examples of cancer include but not limited to, adrenal cancer, bladder cancer, bone cancer, brain cancer, breast cancer, cervical cancer, colorectal cancer, endometrial cancer, head and neck cancer, kidney cancer, liver cancer, lung cancer (including small-cell lung cancer, or non-small cell lung cancer), lymphoma, melanoma, ovarian cancer, pancreatic cancer, skin cancer, or thyroid tumors and their complications. Particularly preferred cancers or tumors that may be treated by the combination disclosed herein include those characterized by B-Raf mutations, K-Ras/N-Ras mutations and/or NF1 mutations. The most preferred cancers or tumors that may be treated by the combination disclosed herein include non-small cell lung cancer, colorectal cancer, and endometrial cancer, each of which is associated with K-Ras mutations.

The term "CDRs" means complementarity determining region(s) in an immunoglobulin variable region, defined using the Kabat numbering system, unless otherwise indicated.

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL-1, B7H1, B7-4, CD274 and B7-H for PD-L1; and PDCD1L2, PDL2, B7-DC, Btdc and CD273 for PD-L2.

PD-1 Antagonist

As disclosed in each of the above five aspects, the PD-1 antagonist is an antibody or a fragment antigen binding thereof, which specifically binds to human PD-1.

As disclosed in each of the above five aspects, the PD-1 antagonist is an antibody which comprises a heavy chain variable region (Vh) and a light chain variable region (Vk) that contain complement determinant regions (CDRs) listed as follows:

| | |
|---|---|
| a) mu317 | CDR-H1, CDR-H2 and CDR-H3 (SEQ ID NOs: 11, 12, 13, respectively); and CDR-L1, CDR-L2 and CDR-L3 (SEQ ID NOs: 14, 15, 16, respectively); |
| b) mu326 | CDR-H1, CDR-H2 and CDR-H3 (SEQ ID NOs: 17, 18, 19, respectively); and CDR-L1, CDR-L2 and CDR-L3 (SEQ ID NOs: 20, 21, 22, respectively); |
| c) 317-4B6 | CDR-H1, CDR-H2 and CDR-H3 (SEQ ID NOs: 31, 32, 33, respectively); and CDR-L1, CDR-L2 and CDR-L3 (SEQ ID NOs: 34, 35, 36, respectively); |
| d) 326-4A3 | CDR-H1, CDR-H2 and CDR-H3 (SEQ ID NOs: 37, 38, 39, respectively); and CDR-L1, CDR-L2 and CDR-L3 (SEQ ID NOs: 40, 41, 42, respectively); |
| e) 317-1H | CDR-H1, CDR-H2 and CDR-H3 (SEQ ID NOs: 11, 59, 13, respectively); and CDR-L1, CDR-L2 and CDR-L3 (SEQ ID NOs: 14, 15, 16, respectively); |
| f) 317-4B2 | CDR-HL CDR-H2 and CDR-H3 (SEQ ID NOs: 11, 60, 13, respectively); and CDR-L1, CDR-L2 and CDR-L3 (SEQ ID NOs: 61, 15, 16, respectively); |
| g) 317-4B5 | CDR-H1, CDR-H2 and CDR-H3 (SEQ ID NOs: 11, 60, 13, respectively); and CDR-L1, CDR-L2 and CDR-L3 (SEQ ID NOs: 61, 15, 16, respectively); |
| h) 317-4B6 | CDR-H1, CDR-H2 and CDR-H3 (SEQ ID NOs: 11, 32, 13, respectively); and CDR-L1, CDR-L2 and CDR-L3 (SEQ ID NOs: 61, 15, 16, respectively); |
| i) 326-1 | CDR-H1, CDR-H2 and CDR-H3 (SEQ ID NOs: 17, 62, 19, respectively); and CDR-L1, CDR-L2 and CDR-L3 (SEQ ID NOs: 20, 21, 22, respectively); |
| j) 326-3B1 | CDR-H1, CDR-H2 and CDR-H3 (SEQ ID NOs: 17, 62, 19, respectively); and CDR-L1, CDR-L2 and CDR-L3 (SEQ ID NOs: 20, 21, 22, respectively); |
| or k) 326-3G1 | CDR-H1, CDR-H2 and CDR-H3 (SEQ ID NOs: 17, 62, 19, respectively); and CDR-L1, CDR-12 and CDR-L3 (SEQ ID NOs: 20, 21, 22, respectively). |

As disclosed in each of the above five aspects, the PD-1 antagonist is an antibody which comprises a heavy chain variable region (Vh) and alight chain variable region (Vk) that contain any combinations of CDRs-listed-as-follows:

| | |
|---|---|
| (a) | CDR-H1 (SEQ ID NO 31), CDR-H2 (SEQ ID NO 12, 32, 59 or 60) and CDR-H3 (SEQ ID NO 33), CDR-L1 ( SEQ ID NO 14, 34 or 61), CDR-L2 (SEQ ID NO 35) and CDR-L3 (SEQ ID NO 36); or |
| (b) | CDR-H1 (SEQ ID NO 37), CDR-H2 (SEQ ID NO 18, 38 or 62) and CDR-H3 (SEQ ID NO 39), CDR-L1 (SEQ ID NO 40), CDR-L2 (SEQ ID NO 41) and CDR-L3 (SEQ ID NO 42). |

As disclosed in each of the above five aspects, the PD-1 antagonist is an antibody which comprises a heavy chain variable region (Vh) and a light chain variable region (Vk) comprising:

a) mu317 (SEQ ID NOs: 4 and 6, respectively);
b) mu326 (SEQ ID NOs: 8 and 10, respectively);
c) 317-4B6 (SEQ ID NOs: 24 and 26, respectively);
d) 326-4A3 (SEQ ID NOs: 28 and 30, respectively);
e) 317-4B2 (SEQ ID NOs: 43 and 44, respectively);
f) 317-4B5 (SEQ ID NOs: 45 and 46, respectively);
g) 317-1 (SEQ ID NOs: 48 and 50, respectively);
h) 326-3B1 (SEQ ID NOs: 51 and 52, respectively);
i) 326-3GI (SEQ ID NOs: 53 and 54, respectively);
j) 326-1 (SEQ ID NOs: 56 and 58, respectively);
k) 317-3A1 (SEQ ID NOs: 64 and 26, respectively);
l) 317-3C1 (SEQ ID NOs: 65 and 26, respectively);
m) 317-3E1 (SEQ ID NOs: 66 and 26, respectively);
n) 317-3F1 (SEQ ID NOs: 67 and 26, respectively);
o) 317-3G1 (SEQ ID NOs: 68 and 26, respectively);
p) 317-3H1 (SEQ ID NOs: 69 and 26, respectively);
q) 317-311 (SEQ ID NOs: 70 and 26, respectively);
r) 317-4B 1 (SEQ ID NOs: 71 and 26, respectively);
s) 317-4B3 (SEQ ID NOs: 72 and 26, respectively);
t) 317-4B4 (SEQ ID NOs: 73 and 26, respectively);
u) 317-4A2 (SEQ ID NOs: 74 and 26, respectively);
v) 326-3 A 1 (SEQ ID NOs: 75 and 30, respectively);
w) 326-3C1 (SEQ ID NOs: 76 and 30, respectively);
x) 326-3D1 (SEQ ID NOs: 77 and 30, respectively);
y) 326-3E1 (SEQ ID NOs: 78 and 30, respectively);
z) 326-3F1 (SEQ ID NOs: 79 and 30, respectively);
aa) 326-3B N55D (SEQ ID NOs: 80 and 30, respectively);
ab) 326-4A1 (SEQ ID NOs: 28 and 81, respectively); or
ac) 326-4A2 (SEQ ID NOs: 28 and 82, respectively).

As disclosed in each of the above five aspects, the PD-1 antagonist is an antibody which comprises a IgG4 heavy chain effector or constant domain comprising any of SEQ ID NOs: 83-88.

As disclosed in each of the above five aspects, the PD-1 antagonist is an antibody which contains a F(ab) or F(ab)$_2$ comprising a domain said above, including a heavy chain variable region (Vh), a light chain variable region (Vk) and a IgG4 heavy chain effector or constant domain.

As disclosed in each of the above five aspects, the PD-1 antagonist is an antibody which comprise a heavy chain variable region (Vh) and a light chain variable region (Vk), and a IgG4 heavy chain effector or constant domain comprising SEQ ID NOs: 87 or 88, wherein the heavy chain variable region (Vh) and the light chain variable region (Vk) comprise:

a) mu317 (SEQ ID NOs: 4 and 6, respectively);
b) mu326 (SEQ ID NOs: 8 and 10, respectively);
c) 317-4B6 (SEQ ID NOs: 24 and 26, respectively);
d) 326-4A3 (SEQ ID NOs: 28 and 30, respectively);
e) 317-4B2 (SEQ ID NOs: 43 and 44, respectively);
f) 317-4B5 (SEQ ID NOs: 45 and 46, respectively);
g) 317-1 (SEQ ID NOs: 48 and 50, respectively);
h) 326-3B1 (SEQ ID NOs: 51 and 52, respectively);
i) 326-3GI (SEQ ID NOs: 53 and 54, respectively);
j) 326-1 (SEQ ID NOs: 56 and 58, respectively);
k) 317-3A1 (SEQ ID NOs: 64 and 26, respectively);
l) 317-3C1 (SEQ ID NOs: 65 and 26, respectively);
m) 317-3E1 (SEQ ID NOs: 66 and 26, respectively);
n) 317-3F1 (SEQ ID NOs: 67 and 26, respectively);
o) 317-3G1 (SEQ ID NOs: 68 and 26, respectively);
p) 317-3H1 (SEQ ID NOs: 69 and 26, respectively);
q) 317-311 (SEQ ID NOs: 70 and 26, respectively);
r) 317-4B 1 (SEQ ID NOs: 71 and 26, respectively);
s) 317-4B3 (SEQ ID NOs: 72 and 26, respectively);
t) 317-4B4 (SEQ ID NOs: 73 and 26, respectively);
u) 317-4A2 (SEQ ID NOs: 74 and 26, respectively);
v) 326-3 A 1 (SEQ ID NOs: 75 and 30, respectively);
w) 326-3C1 (SEQ ID NOs: 76 and 30, respectively);
x) 326-3D1 (SEQ ID NOs: 77 and 30, respectively);
y) 326-3E1 (SEQ ID NOs: 78 and 30, respectively);
z) 326-3F1 (SEQ ID NOs: 79 and 30, respectively);
aa) 326-3B N55D (SEQ ID NOs: 80 and 30, respectively);
ab) 326-4A1 (SEQ ID NOs: 28 and 81, respectively); or
ac) 326-4A2 (SEQ ID NOs: 28 and 82, respectively).

As disclosed in each of the above five aspects, the PD-1 antagonist is an antibody which comprises a heavy chain variable region (Vh) and a light chain variable region (Vk), and an IgG4 heavy chain effector or constant domain comprising SEQ ID NO: 88, wherein the heavy chain variable region (Vh) and the light chain variable region (Vk) comprises SEQ ID NO: 24 and SEQ ID NO: 26, respectively.

The Anti-PD1 Antibodies and antibody fragments thereof disclosed herein may be prepared in accordance with the disclosure of WO 2015/035606 A1, the entire disclosure of which is expressly incorporated herein by reference.

RAF Inhibitors

"RAF inhibitor" means a compound of Formula (I), or a stereoisomer thereof, or a pharmaceutically acceptable salt thereof.

As disclosed in each of the above five aspects, the RAF inhibitor is a compound of Formula (I),

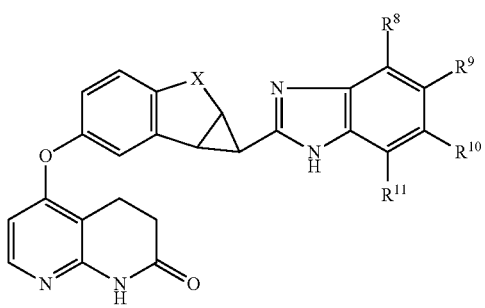

(I)

or a stereoisomer thereof, or a pharmaceutically acceptable salt thereof, wherein:

X is selected from $CH_2$ and O;

$R^8$, $R^9$, $R^{10}$ and $R^{11}$, which may be the same or different, are each selected from hydrogen, halogen, alkyl, alkenyl, cycloalkyl, aryl, heterocyclyl, heteroaryl, alkynyl, $-NR^{13}R^{14}$, $-OR^{13}$, $-COR^{13}$, $-CO_2R^{13}$, $-CONR^{13}R^{14}$, $-C(=NR^{13})NR^{14}R^{15}$, $-NR^{13}COR^{14}$, $-NR^{13}CONR^{14}R^{15}$, $-NR^{13}CO_2R^{14}$, $-SO_2R^{13}$, $-SO_2$aryl, $-NR^{13}SO_2NR^{14}R^{15}$, and $-NR^{13}SO_2R^{14}$, wherein the alkyl, alkenyl, alkynyl, cycloalkyl, heteroaryl, aryl, and heterocyclyl are each optionally substituted with at least one substituent $R^{16}$, or ($R^8$ and $R^9$), and/or ($R^9$ and $R^{10}$), and/or ($R^{10}$ and $R^{11}$) together with the ring to which they are attached, form a fused ring selected from heterocyclyl, and heteroaryl rings optionally substituted with at least one substituent $R^{16}$;

$R^{13}$, $R^{14}$ and $R^{15}$, which may be the same or different, are each selected from H, haloalkyl, alkyl, alkenyl, alkynyl, cycloalkyl, heterocyclyl, aryl, and heteroaryl; or ($R^{13}$ and $R^{14}$), and/or ($R^{14}$ and $R^{15}$) together with the atom(s) to which they are attached, each form a ring selected from heterocyclyl, and heteroaryl rings optionally substituted with at least one substituent $R^{16}$; $R^{16}$ is selected from halogen, haloalkyl, alkyl, alkenyl, cycloalkyl, aryl, heteroaryl, heterocyclyl, alkynyl, oxo, $-CN$, $-OR'$, $-NR'R''$, $-COR'$, $-CO_2R'$, $-CONR'R''$, $-C(=NR')NR''R'''$, $-NR'COR''$, $-NR'CONR'R''$, $-NR'CO_2R''$, $-SO_2R'$, $-SO_2$aryl, $-NR'SO_2NR''R'''$, $-NR'O_2R''$, and $-NR'SO_2$aryl, wherein R', R'', and R''' are independently selected from H, haloalkyl, alkyl, alkenyl, alkynyl, cycloalkyl, heterocyclyl, aryl, and heteroaryl, or (R' and R''), and/or (R'' and R''') together with the atoms to which they are attached, form a ring selected from heterocyclyl, and heteroaryl rings.

In some embodiments, the compound of Formula (I) is optically pure.

In some embodiments, X in Formula (I) is O.

In some embodiments, X in Formula (I) is $CH_2$.

In some embodiments, $R^8$, $R^9$, $R^{10}$, and $R^{11}$ in Formula (I), which may be the same or different, are each independently selected from alkyl (e.g., methyl, tert-butyl), hydrogen, haloalkyl (e.g., $-CF_3$), halogen, hydroxy, $-CN$, $-$Oalkyl (e.g., methoxy), $-$Ohaloalkyl (e.g., $OCF_3$), and aryl (e.g., phenyl).

As disclosed in each of the above five aspects, the RAF inhibitor is a compound of Formula (I),

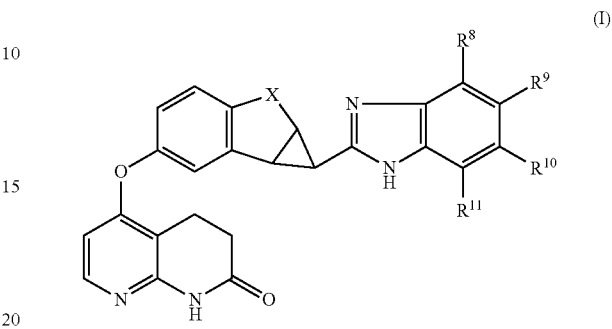

(I)

or a stereoisomer thereof, or a pharmaceutically acceptable salt thereof, wherein:

X is selected from $CH_2$ and O;

$R^8$, $R^9$, $R^{10}$ and $R^{11}$, which may be the same or different, are each selected from hydrogen, halogen, alkyl, $-CN$, cycloalkyl, aryl, heterocyclyl, $-OR^{13}$, $-CONR^{13}R^{14}$, wherein the alkyl, and aryl are each optionally substituted with at least one substituent $R^{16}$, or ($R^8$ and $R^9$), and/or ($R^9$ and $R^{10}$), and/or ($R^{10}$ and $R^{11}$) together with the ring to which they are attached, form a fused ring selected from cycloalkyl;

$R^{13}$, and $R^{14}$, which may be the same or different, are each selected from H, alkyl, and haloalkyl;

$R^{16}$ is selected from halogen, haloalkyl, and alkyl.

As disclosed in each of the above five aspects, the RAF inhibitor is a compound of Formula (I),

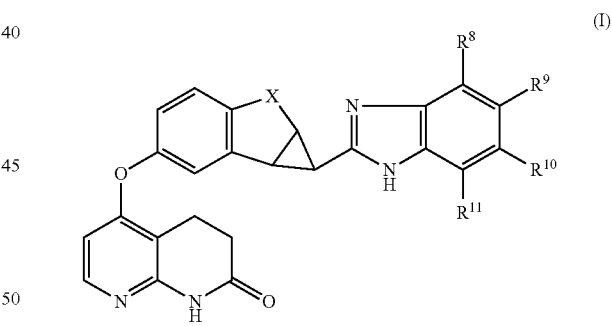

(I)

or a stereoisomer thereof, or a pharmaceutically acceptable salt thereof, wherein:

X is selected from $CH_2$ and O;

$R^8$ is selected from H, F, Cl, and Br;

$R^9$ is selected from H, F, Cl, Br, and $C_{1-6}$alkyl;

$R^{10}$ is selected from H, F, Cl, Br, OH, $-CN$, $C_{1-6}$alkyl, $CF_3$, phenyl, $OC_{1-6}$alkyl, $OC_{1-6}$haloalkyl, and $-CONR^{13}R^{14}$, wherein $R^{13}$ and $R^{14}$ may be the same or different, are each selected from H, and $C_{1-6}$alkyl;

$R^{11}$ is selected from H, F, Cl, Br, and $CF_3$;

or ($R^9$ and $R^{10}$) together with the ring to which they are attached, form a fused ring selected from $C_{5-6}$cycloalkyl.

As disclosed in each of the above five aspects, the RAF inhibitor is a compound of selected from the following compounds:

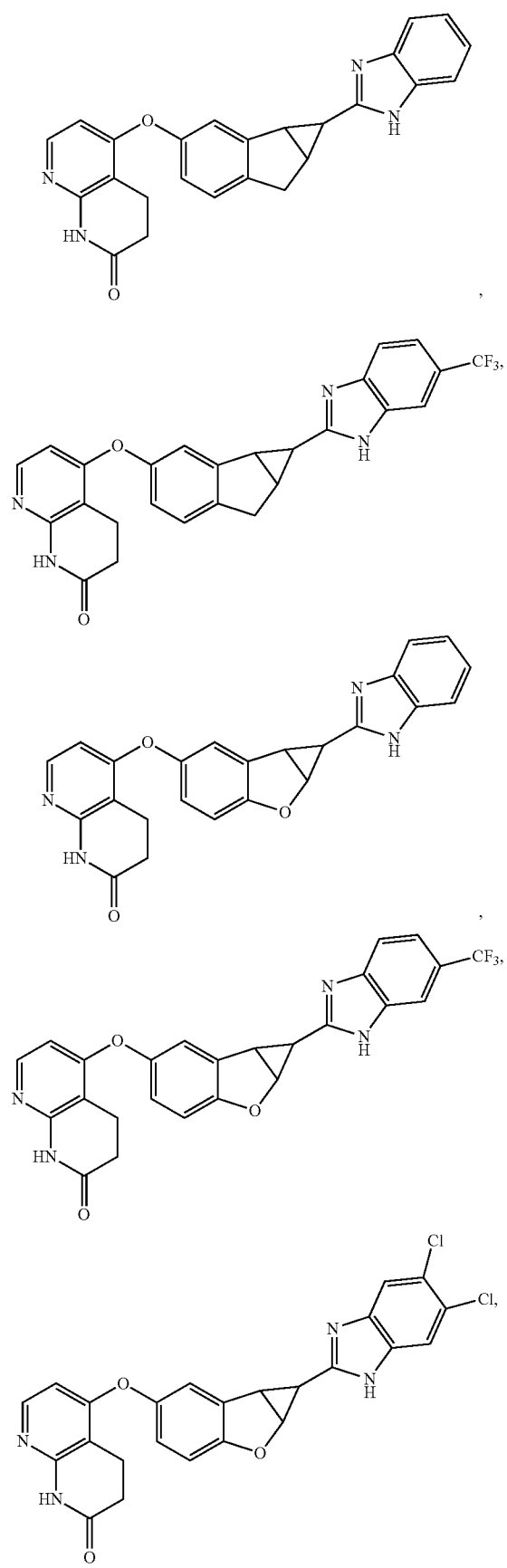 [SMILES: O=C1CCc2c(Oc3ccc4c(c3)C3C(C4)C3c3nc4ccccc4[nH]3)ccnc2N1 ; O=C1CCc2c(Oc3ccc4c(c3)C3C(C4)C3c3nc4ccc(C(F)(F)F)cc4[nH]3)ccnc2N1 ; O=C1CCc2c(Oc3ccc4c(c3)C3C(O4)C3c3nc4ccccc4[nH]3)ccnc2N1 ; O=C1CCc2c(Oc3ccc4c(c3)C3C(O4)C3c3nc4ccc(C(F)(F)F)cc4[nH]3)ccnc2N1 ; O=C1CCc2c(Oc3ccc4c(c3)C3C(O4)C3c3nc4cc(Cl)c(Cl)cc4[nH]3)ccnc2N1]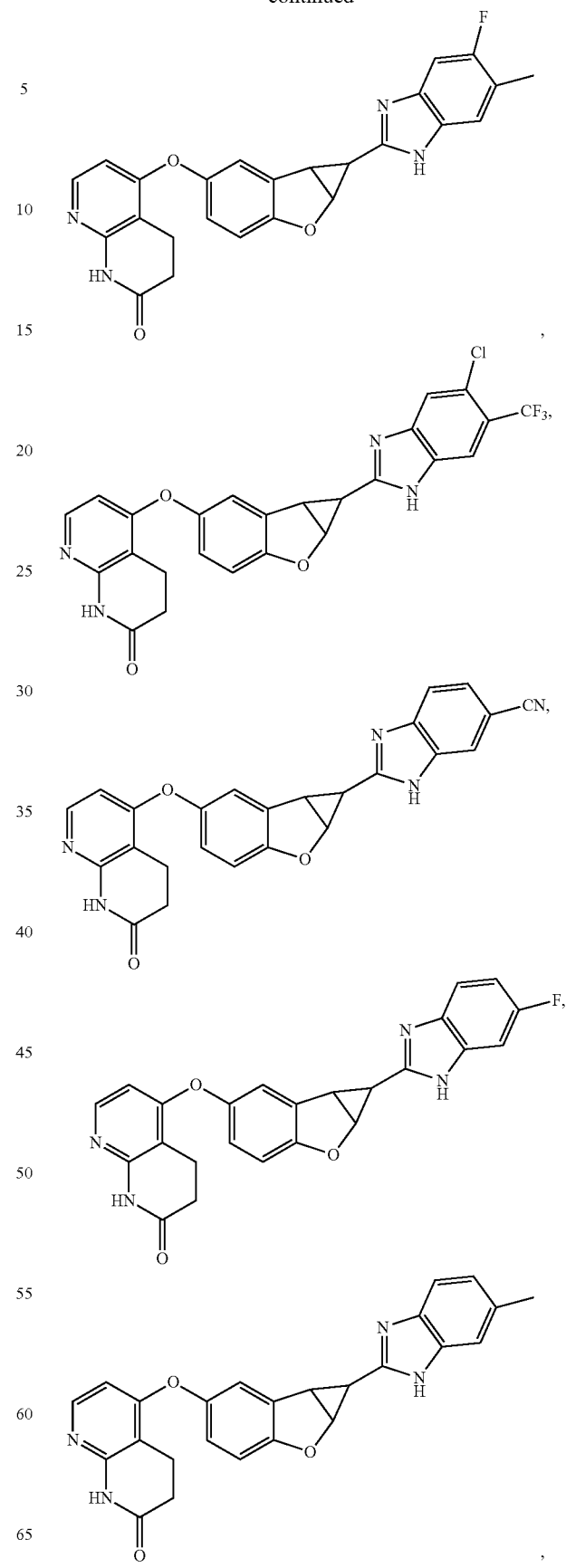

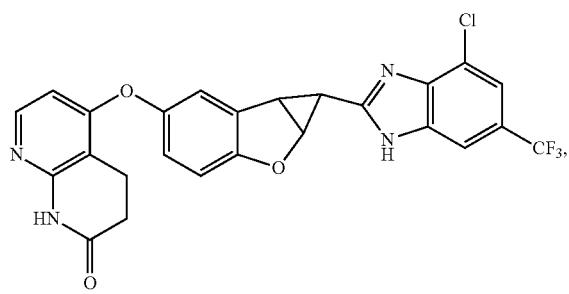
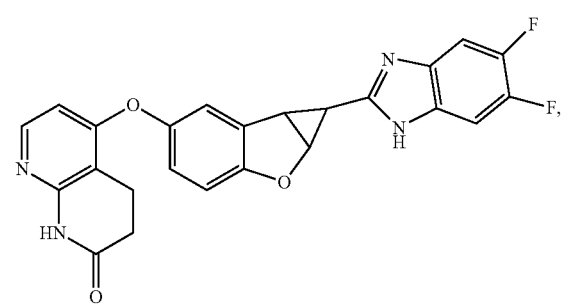
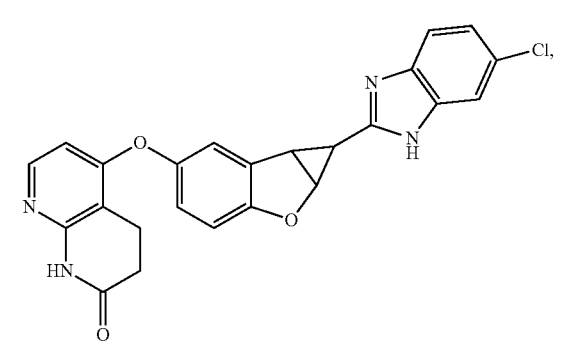
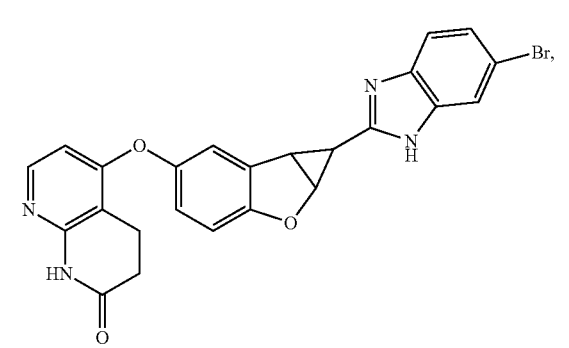
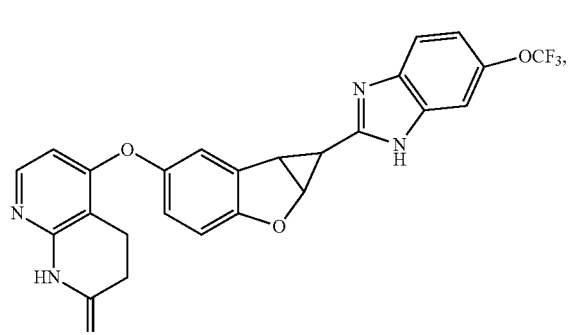
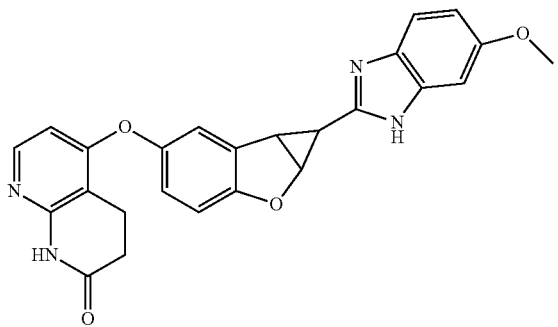
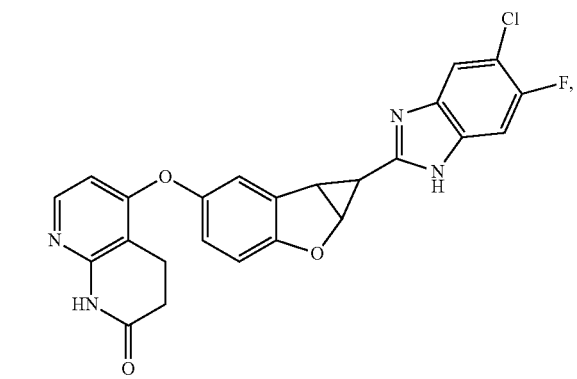
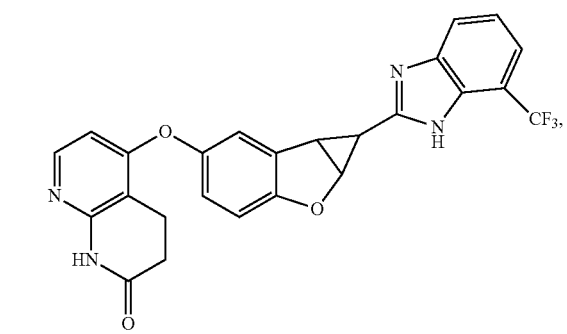
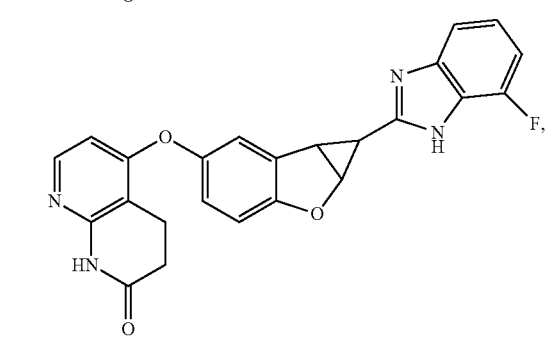
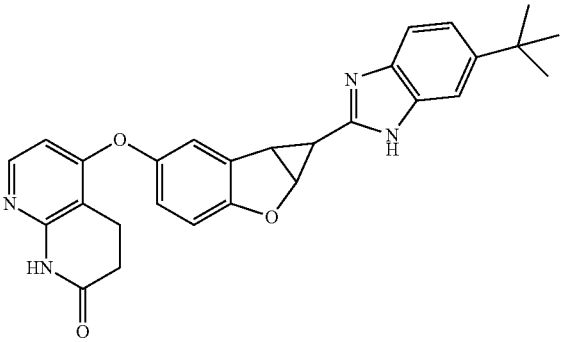

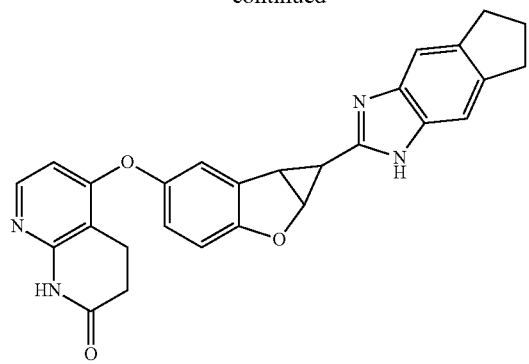
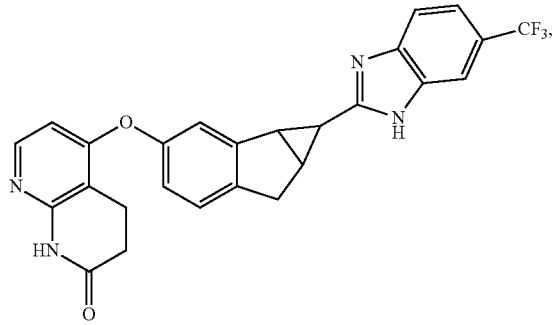
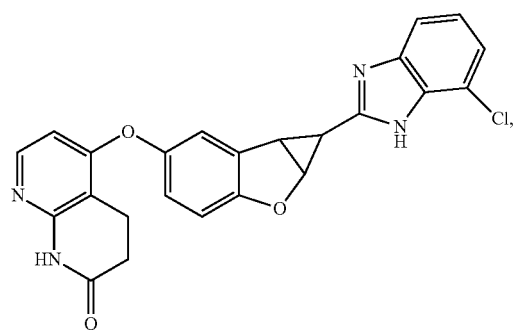
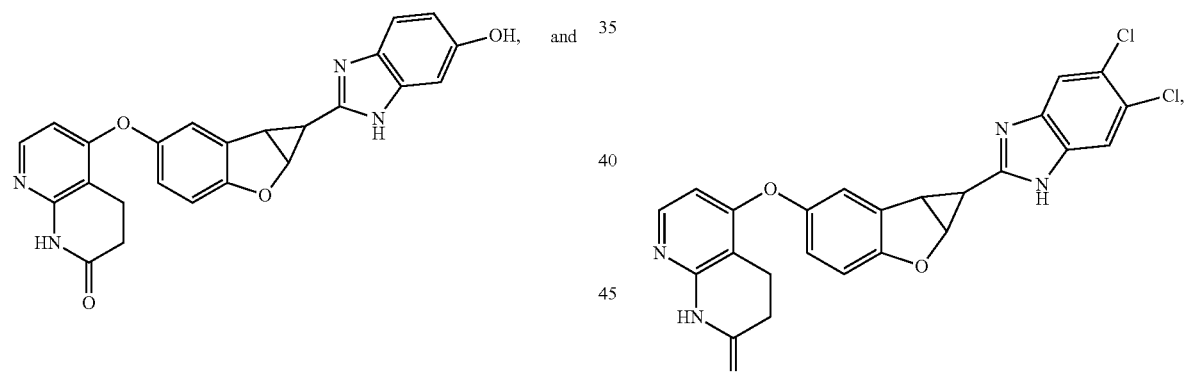
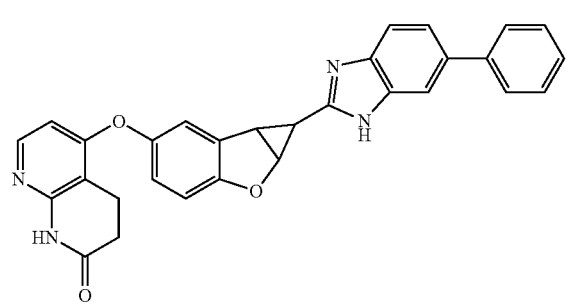
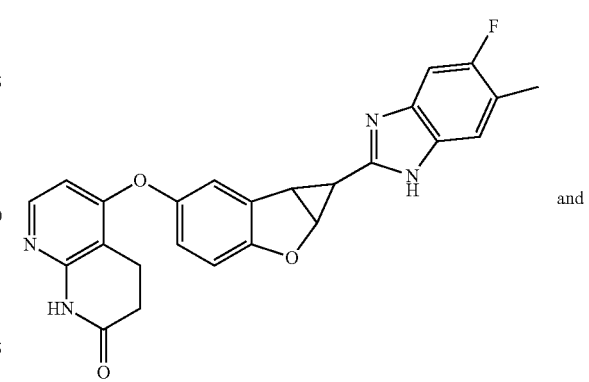
or a stereoisomer thereof, or a pharmaceutically acceptable salt thereof.
As disclosed in each of the above five aspects, the RAF inhibitor is a compound of selected from the following compounds:

-continued
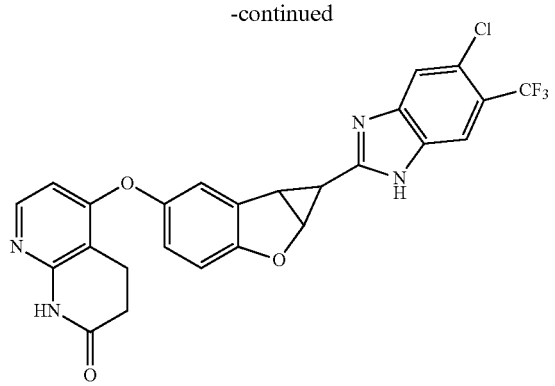
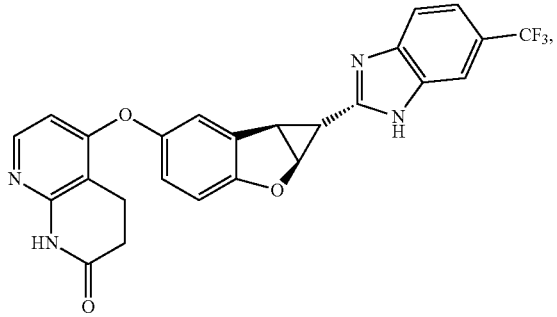
or a stereoisomer thereof, or a pharmaceutically acceptable salt thereof.
As disclosed in each of the above five aspects, the RAF inhibitor is a compound of selected from the following compounds:
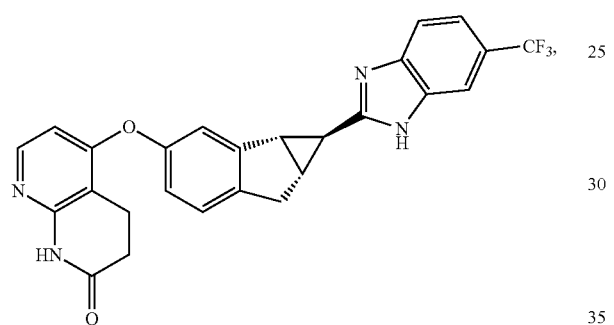
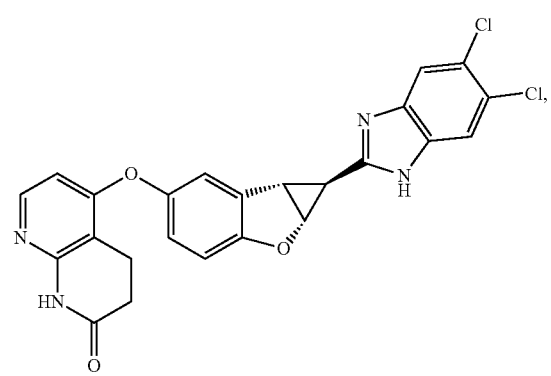
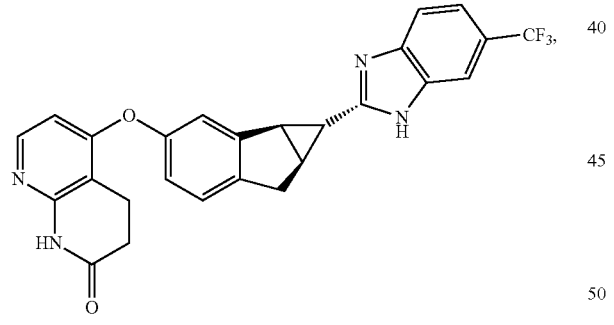
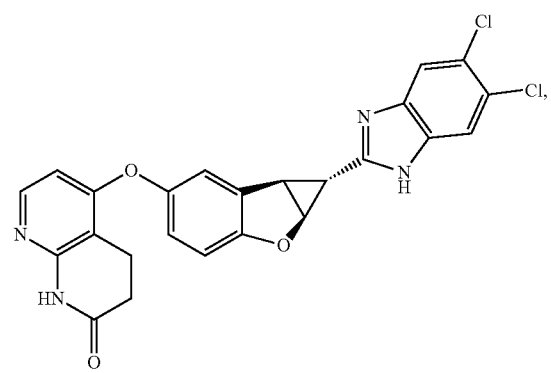
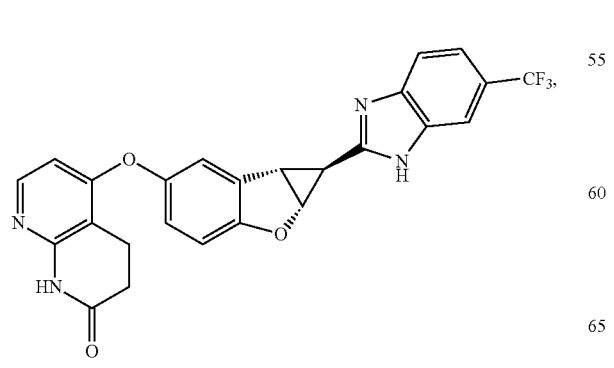
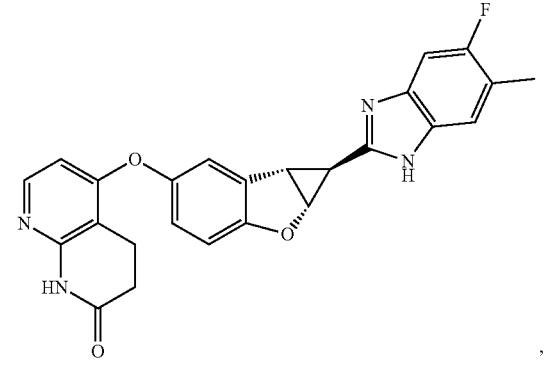

-continued

[Chemical structure]

,

[Chemical structure]

[Chemical structure]

or a pharmaceutically acceptable salt thereof.

As disclosed in each of the above five aspects, the RAF inhibitor is a compound of Formula (II),

[Chemical structure (II)]

or a pharmaceutically acceptable salt thereof.

As disclosed in each of the above five aspects, the RAF inhibitor is a maleate salt of the compound of Formula (II).

As disclosed in each of the above five aspects, the RAF inhibitor is a compound of Formula (III),

[Chemical structure (III)]

wherein n is a number from about 0.5 to about 1.5.

As disclosed in each of the above five aspects, the RAF inhibitor is a compound of Formula (IIIa)—i.e., Compound 1,

[Chemical structure (IIIa)]

The RAF inhibitor disclosed herein, such as the compound of Formula (I), may be synthesized by synthetic routes disclosed in WO 2013/097224 A1, the entire disclosure of which is expressly incorporated herein by reference. The RAF inhibitor, i.e., Compound 1, disclosed herein, may be prepared in accordance with the procedures in PCT/CN2016/079251, the entire disclosure of which is expressly incorporated herein by reference.

Combination Therapy

The combination therapy may be administered as a simultaneous, or separate or sequential regimen. When administered sequentially, the combination may be administered in two or more administrations. The combined administration includes coadministration, using separate formulation, and consecutive administration in either order, wherein preferably there is a time period while both (or all) active agents simultaneously exert their biological activities.

In one embodiment of each of the above five aspects, the RAF inhibitor or the pharmaceutically acceptable salt thereof can be administered for a time period of about 1 to about 10 days after administration of the PD-1 antagonist. In another embodiment of each of the above five aspects, the RAF inhibitor or the pharmaceutically acceptable salt thereof can be administered for a time period of about 1 to 10 days before administration of the combination begins. In another embodiment of each of the above five aspects, administration of the RAF inhibitor or the pharmaceutically acceptable salt thereof and administration of the PD-1 antagonist begin on the same day.

Suitable dosages for any of the above coadministered agents are those presently used and may be lowered due to the combined action (synergy) of the RAF inhibitor and the PD-1 antagonist, such as to increase the therapeutic index or mitigate toxicity or other side-effects or consequences.

In a particular embodiment of anti-cancer therapy, the RAF inhibitor and the PD-1 antagonist may be further combined with surgical therapy and radiotherapy.

In an embodiment of each of the above five aspects, the amounts of the RAF inhibitor and the PD-1 antagonist disclosed herein and the relative timings of administration be determined by the individual needs of the patient to be treated, administration route, severity of disease or illness, dosing schedule, as well as evaluation and judgment of the designated doctor.

For example, the administered dosage of the RAF inhibitor is 1-100 mg/day (in terms of the parent compound), and the administration frequency is one to three times a day; preferably, the administered dosage of the RAF inhibitor is 5-80 mg/day (in terms of the parent compound), and the administration frequency is one to three times a day; more preferably, the administered dosage of the RAF inhibitor is 10-40 mg/day (in terms of the parent compound), and the administration frequency is one time a day. However, based on the active compound, the preferred range of the effective dosage of the RAF inhibitor disclosed herein may be approximately 0.01-10 mg daily per kilogram of body weight; or more preferably 0.1-1 mg per day per kilo gram of body weight in single or separate doses. In some cases, it is more suitable to apply the lower end of the above described dosage ranges, while in other cases the higher dosages may be used without causing harmful side effects. In some preferred embodiment of each of the above five aspects, the RAF inhibitor is administered at a dose of 5-80 mg once daily.

The PD-1 antagonist is administered at a dose of 0.5-30 mg/kg, such as 0.5-20 mg/kg, further such as 0.5-10 mg/kg once weekly, or every two weeks, or every three weeks, or every four weeks.

The RAF inhibitor and the PD-1 antagonist disclosed herein may be administered in various known manners, such as orally, topically, rectally, parenterally, by inhalation spray, or via an implanted reservoir, although the most suitable route in any given case will depend on the particular host, and nature and severity of the conditions for which the active ingredient is being administered.

The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

In one embodiment of each of the above five aspects, the RAF inhibitor and the PD-1 antagonist disclosed herein may be administered in different route. In a preferred embodiment, the RAF inhibitor is administered orally, and the PD-1 antagonist is administered parenterally such as subcutaneously, intracutaneously, intravenously or intraperitoneally.

In an embodiment of each of the above five aspects, the PD-1 antagonist is an antibody which comprises a heavy chain variable region (Vh) and a light chain variable region (Vk), and a IgG4 heavy chain effector or constant domain comprising SEQ ID NO: 88, wherein the heavy chain variable region (Vh) and the light chain variable region (Vk) comprise SEQ ID NO: 24 and SEQ ID NO: 26, respectively; and the RAF inhibitor is the compound of Formula (IIIa) disclosed herein.

In an embodiment of each of the above five aspects, the PD-1 antagonist Mab-1 is administrated to a subject at a dose of 0.5-10 mg/kg i.v. or i.p. QW or Q2W or Q3W, and the RAF inhibitor Compound 1 is administrated to a subject at a dose of 5-80 mg QD. In some preferred embodiments, the PD-1 antagonist Mab-1 is administrated to a subject at a dose of 0.5-10 mg/kg i.v. or i.p. QW or Q2W or Q3W, and the RAF inhibitor Compound 1 is administrated to a subject at a dose of 10-30 mg QD. In an even more preferred embodiment, the PD-1 antagonist Mab-1 is administrated parenterally such as subcutaneously, intracutaneously, intravenously or intraperitoneally.

Methods of Treatment

The pharmaceutical combination produces synergistic efficacy in inhibiting tumor growth in cancer, such as adrenal cancer, bladder cancer, bone cancer, brain cancer, breast cancer, cervical cancer, colorectal cancer, endometrial cancer, head and neck cancer, kidney cancer, liver cancer, lung cancer (including small-cell lung cancer, or non-small cell lung cancer), lymphoma, melanoma, ovarian cancer, pancreatic cancer, skin cancer, or thyroid tumors and their complications. Particularly, the combination is effective in the above cancer associated with B-Raf mutations, K-Ras/N-Ras mutations and/or NF1 mutations. The most preferred cancers or tumors that may be treated by the combination disclosed herein include non-small cell lung cancer, colorectal cancer, and endometrial cancer, each of which is associated with K-Ras mutations. The combination is useful in a method for the prevention, delay of progression or treatment of cancer.

EXAMPLES

Example A: Preparation of Compound 1 (i.e., the Sesqui-Maleate Salt)

Step 1: Synthesis of Intermediate 1

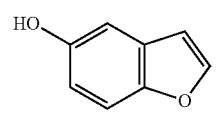

Intermediate 1

To a stirred solution of EtONa (154 kg) in DMF (989 kg) was added EtSH (68.6 kg) at an inner temperature ≤ 35° C. under nitrogen protection. The mixture was stirred for 60-90 min at the inner temperature ≤ 35° C. 5-Methoxybenzofuran (58.75 kg) in DMF (55.0 kg) was added. The mixture was heated to 110-130° C., stirred for 45 hours, and then concentrated under vacuum below 90° C. After the mixture was cooled to 10~20° C., 2N HCl (1326 kg) was added dropwise, followed by addition of EtOAc (531 kg) and $H_2O_2$ (129 kg) at the inner temperature ≤ 35° C. The mixture was stirred for 30-60 min. After separation of the organic layer, the aqueous phase was extracted with EtOAc. The combined organic phase was washed with saturated brine twice, and then the solvent was evaporated to dryness. MeOH and a solution of NaOH (44.5 kg) in water (185 kg) were added dropwise into the residue below 40° C. The mixture was stirred for 5-7 hours at 30~40° C. Active carbon (74 kg) wet up with water (77 kg) was added. The mixture was stirred for 4-6 hours at 30~40° C. and filtered; and the filter cake was washed with MeOH and water. DCM was charged into the filtrate and pH was adjusted to 1 with 35% aq. HCl below 40° C. The aqueous phase was extracted with DCM, and the organic phase was washed with 25% NaCl and concentrated below 40° C. The residue was used in the next step directly. $^1$H NMR (400 MHz, DMSO-d6) δ 9.14 (s, 1H), 7.86 (d, J=2.0 Hz, 1H), 7.36 (d, J=8.8 Hz, 1H), 6.94 (d, J=2.4 Hz, 1H), 6.79 (dd, J=2.0, 0.9 Hz, 1H), 6.74 (dd, J=8.8, 2.4 Hz, 1H) ppm. MS: M/e 135 (M+1)+.

Step 2: Synthesis of Intermediate 2

Intermediate 2

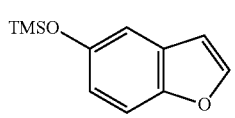

To a stirred solution of benzofuran-5-ol (Intermediate 1, 33.1 kg) and Et$_3$N (50.8 kg) in DCM (155 kg) was added dropwise a solution of TMSCl (30.4 kg) in DCM (50 kg) at −5 to 0° C. The mixture was warmed to 0~10° C. and stirred at the temperature for 2 hours (IPC checked INT-1/INT-2=37.4%). The mixture was cooled to between −5 and 0° C. and was added dropwise a solution of TMSCl (10.6 kg) in DCM (8 kg), and then the mixture was warmed to 0~10° C. and stirred at the temperature for 1h. The mixture was concentrated below 40° C., and to the mixture was added n-heptane. The mixture was stirred for 20-30 mins and filtered, and the cake was washed with n-heptane. The solvent was distilled out from the filtrate to obtain a crude Intermediate 2 (INT-2%: 62.7%, KF: 0.01%). To a stirred solution of the crude Intermediate 2 above and Et$_3$N (8.6 kg) in DCM (149 kg) was added dropwise a solution of TMSCl (9.0 kg) in DCM (10 kg) at −5 to 0° C. The mixture was warmed to 0~10° C. and stirred at the temperature for 1h (TLC showed the reaction was finished). The reaction mixture was concentrated below 40° C., and to the mixture was added n-heptane. The mixture was stirred for 20-30 mins and then filtered, and the cake was washed with n-heptane. The solvent was distilled out from the filtrate to obtain Intermediate 2 (41.5 kg, INT-2%: 98.1%) as a colorless oil. H NMR (400 MHz, DMSO-d6) δ 7.69 (d, J=2.0 Hz, 1H), 7.21 (d, J=8.8 Hz, 1H), 6.84 (d, J=2.5 Hz, 1H), 6.61 (d, J=2.0 Hz, 1H), 6.56 (dd, J=8.8, 2.5 Hz, 1H), 0.00 (s, 9H) ppm.

Step 3: Synthesis of Intermediate 3

Intermediate 3

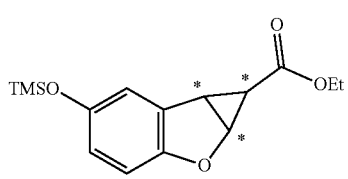

Copper (I) triflate (2:1 complex with toluene, 0.41 kg) and (S,S)-Evans Ligand (0.552 kg) were stirred in DCM (160 kg) at ambient temperature under N2 atmosphere for 1-2 hours. Intermediate 2 (37.0 kg) was added, followed by a slow addition of ethyl diazoethanoate (58 kg) in DCM (450 kg) at 20~30° C. The reaction was stirred for 0.5-1h at 20~30° C. (IPC: INT-2/INT-3≤ 0.2%, residual N$_2$CHCO$_2$Et: 0.05%≤ 1.0%). A solution of EDTA disodium (0.05 mol/L, 150 kg) was added to the reaction mixture for 40~50 min at 20~30° C. in three times. The organic phase was washed with 25% aqueous NaCl at 20~30° C. in two times and concentrated below 30° C. The residue was distilled under reduced pressure and crude Intermediate 3 (36.26 kg, 84.5%) was collected at 120~144° C. The crude compound included the endo-enantiomer which could be removed in the next step. $^1$H NMR (400 MHz, DMSO-d6) δ 6.79 (d, J=2.4 Hz, 1H), 6.59 (d, J=8.4 Hz, 1H), 6.42 (dd, J=8.4, 2.4 Hz, 1H), 4.95 (dd, J=5.4, 1.0 Hz, 1H), 3.08 (dd, J=5.4, 3.2 Hz, 1H), 1.02 (dd, J=3.1, 1.2 Hz, 1H), 0.00 (s, 9H) ppm.

Steps 4 and 5: Syntheses of Intermediate 5 and Intermediate 6

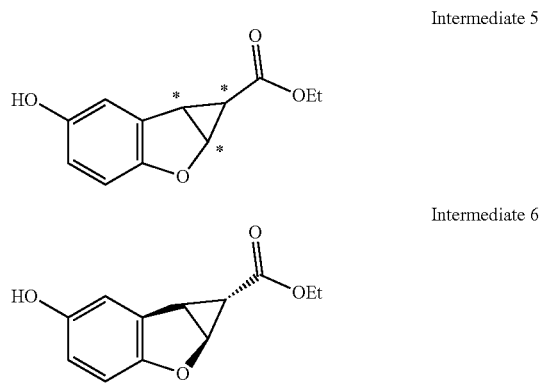

To a solution of Intermediate 4 (36.3 kg) in MeOH (108 kg) was added a solution of HCl/MeOH (5M, 0.11 kg) at 20~30° C., and the mixture was stirred for 2-3 hours (IPC: L/M: 0.5%, chiral purity 90.0%). Et$_3$N (0.22 kg) was added dropwise at 20~30° C. The mixture was concentrated and the residue was diluted with n-heptane/EtOAc (4:1) and then concentrated. After adjusting the temperature to 10~20° C. and stirring for 2~4 hours at 10~20° C., the mixture was filtered to give a wet product (Intermediate 5: 94.0%, chiral purity: 90.5%). $^1$H NMR (400 MHz, DMSO-d6) δ 9.05 (s, 1H), 6.89 (d, J=2.4 Hz, 1H), 6.72 (d, J=8.4 Hz, 1H), 6.55 (dd, J=8.4, 2.4 Hz, 1H), 5.11 (dd, J=5.4, 1.0 Hz, 1H), 3.27 (dd, J=5.4, 3.0 Hz, 1H), 1.19-1.17 (m, 1H) ppm. The crude product was slurried with n-heptane/EtOAc (20:1) three times to give a light yellow solid, which was dried for 12~16 hours at 40~50° C. to give 16.55 kg product (Intermediate 6: 98.6%; chiral purity: 99.3%).

Steps 6 and 7: Syntheses of Intermediate 7 and Intermediate 8

Intermediate 7

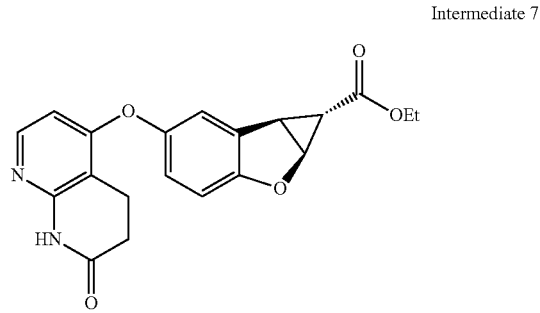

-continued

Intermediate 8

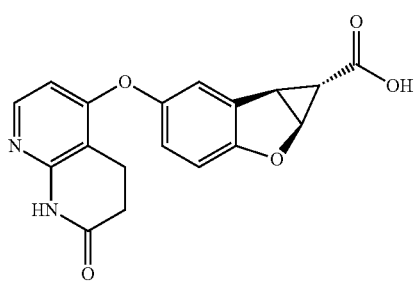

To a solution of Intermediate 6 (14 kg) and 5-fluoro-3,4-dihydro-1,8-naphthyridin-2(1H)-one (SM2, 11.2 kg) in DMF (66 kg) was added Cs$_2$CO$_3$ (26 kg) at 40~60° C., and the mixture was warmed to 110~120° C. and stirred for 3 hours at 110~120° C. The reaction pH was adjusted to 6 with acetic acid (12.0 kg) at 25~35° C. Water (520 kg) was added and the mixture was stirred for 1~2 hours. After filtration, the solid was slurried with EA (78 kg) to get a wet product (the purity: (Intermediate 7+Intermediate 8) %: 98%). An aqueous sodium hydroxide solution (125 kg, 2M) was added to a stirred solution of the wet product in THF (240 kg) and stirred for 2~3 hours at 20~30° C. (IPC: INT-7/INT-8: 0.9%). The mixture was adjusted to pH 4~5 with 4N HCl (37 kg) at 20~30° C. and then stirred for 0.5~1h. The mixture was concentrated at below 50° C. and a solid precipitated out of the solution. After filtration, the wet product was re-slurried in THF at 35~45° C. for 1~2 hours, and then filtered. The resultant wet product was dried for 40 hours at 45~65° C. to give the title compound Intermediate 8 (18.95 kg: chemical purity 99%, chiral purity 100%). $^1$H NMR (400 MHz, DMSO-d6) δ 12.59 (s, 1H), 10.43 (s, 1H), 7.92 (d, J=5.8 Hz, 1H), 7.29 (d, J=2.4 Hz, 1H), 6.97 (d, J=8.8 Hz, 1H), 6.93 (dd, J=8.8, 2.4 Hz, 1H), 6.21 (d, J=5.8 Hz, 1H), 5.21 (dd, J=5.4, 1.0 Hz, 1H), 3.27-3.25 (m, 1H), 2.89 (t, J=7.8 Hz, 2H), 2.51 (d, J=8.8 Hz, 2H), 1.19 (dd, J=3.0, 1.0 Hz, 1H) ppm. MS: M/e 339 (M+1)+.

Step 8: Synthesis of Intermediate 9

Intermediate 9

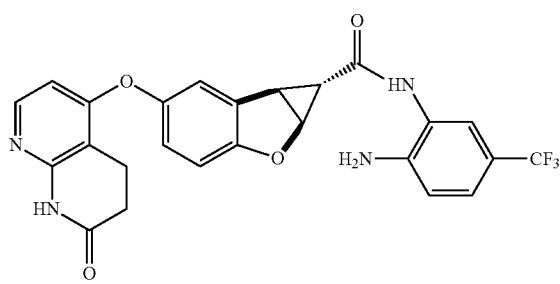

A solution of Intermediate 8(13.3 kg), DIPEA (16 kg) and HATU (18.1 kg) in DMF (167 kg) was added dropwise into a mixture of 4-(trifluoromethyl)benzene-1,2-diamine (SM3, 7.6 kg) in DMF (74 kg) at 0~15° C. The mixture was stirred at 20~25° C. for 4~6 hours (IPC: INT-9/INT-9: not detected). Active carbon (5.3 kg) in DMF (7.5 kg) was added into the reaction mixture, stirred for 2~4 hours at 40~45° C., and then filtered. Water (846 kg) was added dropwise into the filtrate at 15~30° C., and a solid precipitated out of the solution when stirred for 12 hours. The precipitate was filed and slurried in EtOH at 20~30° C. for 2-4 hours. After filtration, the wet product was dried for 37 hours at 45~60° C. to obtain the title compound Intermediate 9 (17.60 kg: 95.5%).

Step 9: Syntheses of Free Base of Compound 1 free base of Compound 1

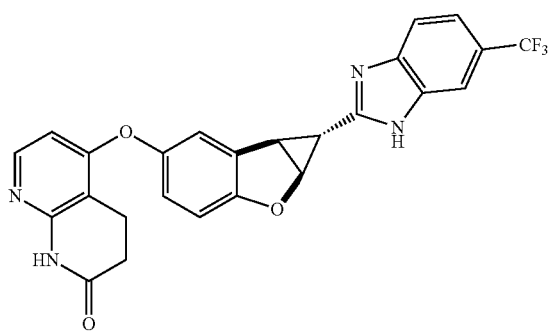

A solution of Intermediate 9 (17 kg) and water (1.5 kg) in AcOH (360 kg) was stirred at 65-70° C. for 20 hours (IPC: R/S≤1.0%). The mixture was concentrated to dryness at below 55° C., and active carbon (17 kg) with MeOH (32 kg) was added to the residue. The mixture was stirred for 1h at about 50° C. After filtration, the filtration was concentrated to remove the solvent at below 45° C. EA (160 kg) and water (330 kg) were added to the residue, followed with an aqueous solution of NaOH (2 mol/L) until pH to 8-9 at 20-30° C. The organic layer was separated, and extracted the aqueous phase with EA. The combined organic phase was washed with water twice, concentrated to dryness to obtain Compound 1 in the form of free base. $^1$H-NMR (600 MHz, DMSO-d$_6$) δ 12.84 (s, 1H), 10.47 (s, 1H), 7.98 (d, J=5.8 Hz, 1H), 7.86 (d, J=1.2 Hz, 1H), 7.69 (m, 1H), 7.48 (t, J=6.2 Hz, 1H), 7.38 (d, J=2.6 Hz, 1H), 7.08 (d, J=8.7 Hz, 1H), 7.02 (dd, J=8.7, 2.6 Hz, 1H), 6.29 (d, J=5.8 Hz, 1H), 5.43 (dd, J=5.4, 1.2 Hz, 1H), 3.55 (dd, J=5.3, 3.3 Hz, 1H), 2.95 (t, J=7.7 Hz, 2H), 2.55 (t, J=7.7 Hz, 2H), 1.97 (d, J=1.3 Hz, 1H) ppm.

Step 10: Syntheses of Compound 1

Compound 1

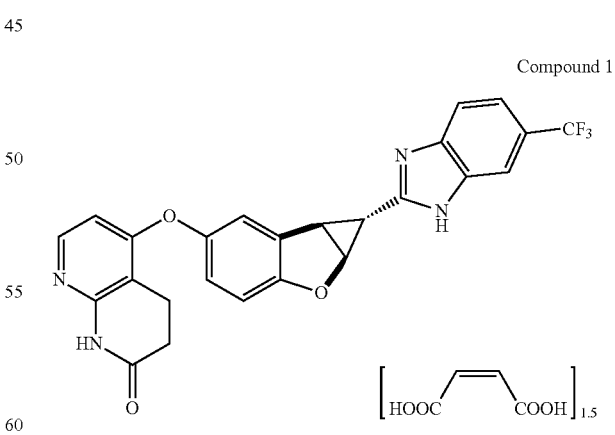

Figure 4:
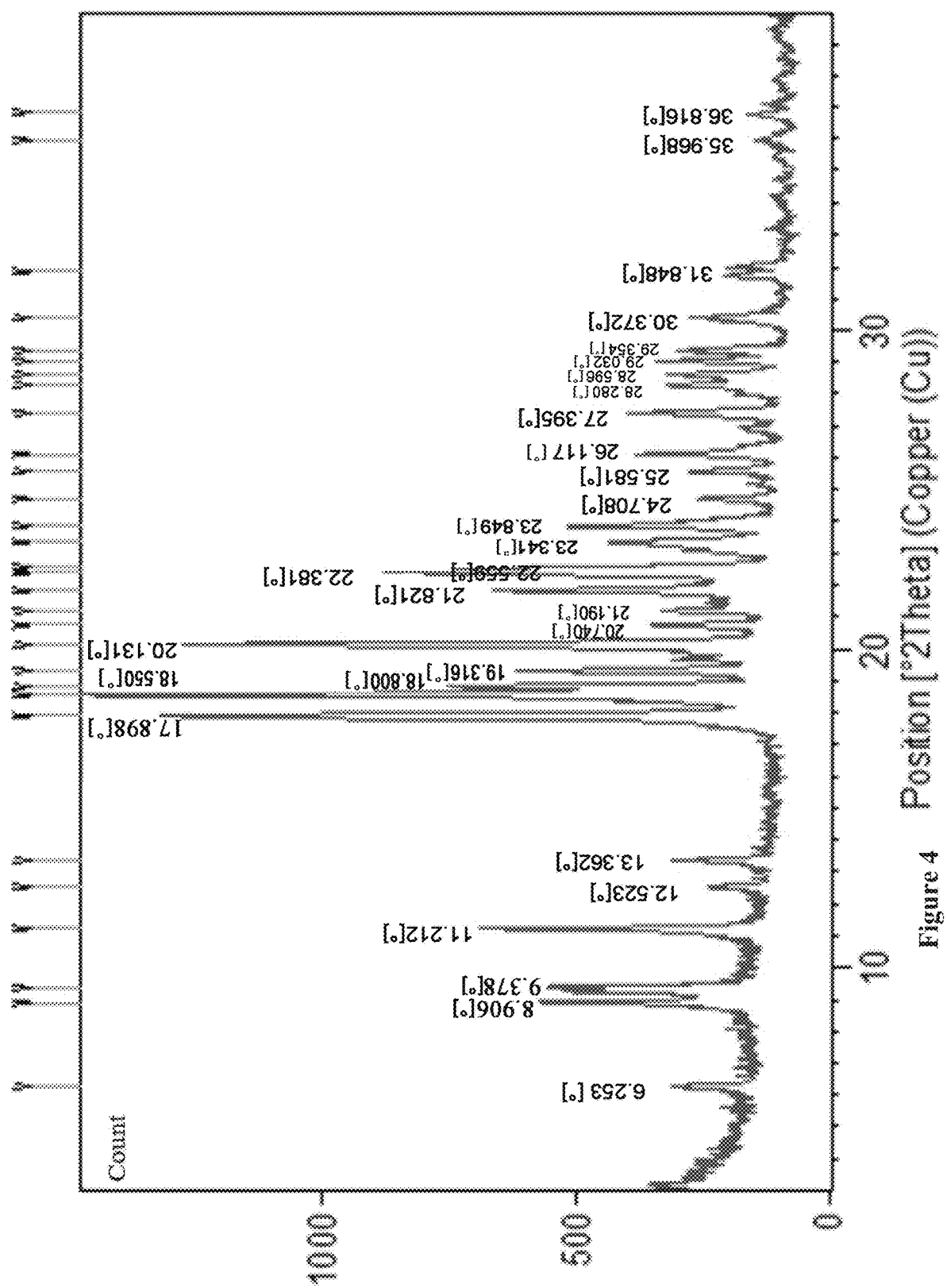
FIG. 4 shows an X-ray diffraction pattern of Compound 1 in a crystalline form (crystallization from isopropanol/water).
Figure 5:
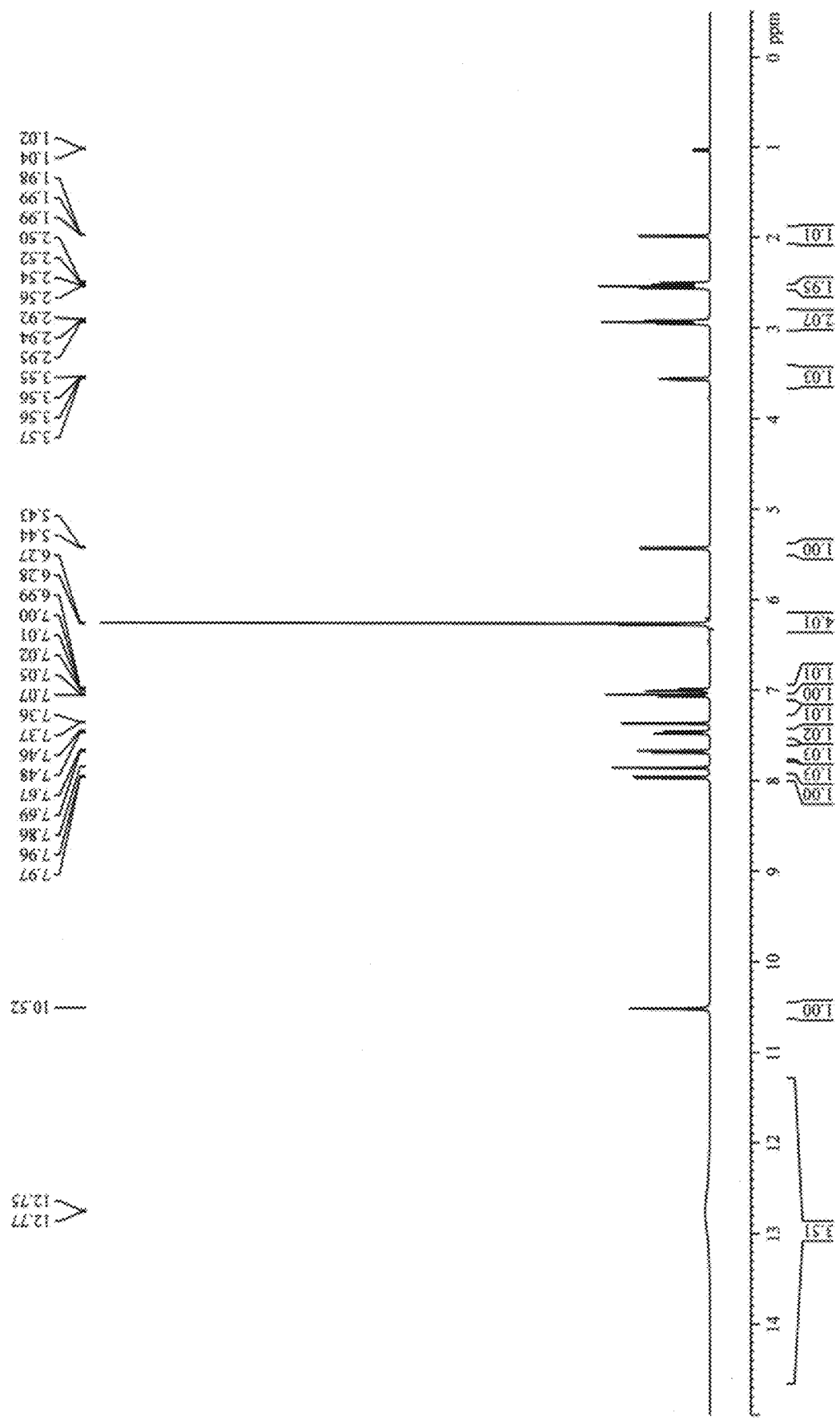
FIG. 5 shows a $^1$H-NMR spectrum of the crystalline form of Compound 1.

IPA (83 kg) was added to the residue of Step 9. Maleic acid (5 kg) in water (29 kg) was added into the mixture and stirred for 4 hours at about 50° C., then cooled to 35° C. and stirred for 12 hours at that temperature. The resultant solid was filtered, dried at 40~60° C., and micronized in a micronizer to give a white powder (Compound 1 Sesqui- Maleate Salt, 8.36 kg) with particle sizes of D90=4.1 μm, D10=1.5 μm, D50=2.4 μm. Compound 1 was identified as a crystalline form by powder X-ray diffraction pattern method as shown in FIG. 4. $^1$H-NMR spectra for Compound 1 in the crystalline form is shown in FIG. 5. $^{13}$C-NMR spectra for Compound 1 in the crystalline form is shown in FIG. 6.

Example 1

Effect of the Combination of RAF Inhibitor and Anti-PD-1-mAb on T Cell Function In Vitro 3D Spheroid/PBMC Co-Culture Model Method For tumor spheroid generation, HEK-293-OS8-PD-L1 cells and Sk-Mel-28 cells (B-Raf$^{V600E}$) were mixed at 1:1 ratio at a density of $5\times10^4$ cells/mL in ice-cold medium. The Matrigel® Matrix (Corning) was added to the cell suspension at a final concentration of 2% to assist the formation of three-dimensional structures. Cells were plated into ULA 96-well round-bottomed plates (Corning) and grow for three days to form tumor spheroids. Blood samples from healthy donors were collected in heparinized tubes and PBMCs were isolated using Fioll-Paque PLUS reagent (GE Healthcare) according to the instruction of manufacturer. Prior to co-culture with tumor spheroids, PBMCs were activated with 1 μg/mL anti-CD3 antibody for two days. Co-culture was performed in ULA 96-well round-bottomed plates containing one tumor spheroid and 104 PBMCs/well in the present of a series dilution of Compound 1(5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyrdin-2(1H)-one Sesqui-Maleate) combining with Mab 1 (containing a heavy chain variable region (Vh) as shown in SEQ ID NO: 24, a light chain variable region (Vk) as shown in SEQ ID NO: 26, and a IgG4 heavy chain effector or constant domain comprising SEQ ID NO: 88) for three days. IFN-γ production level in culture supernatant was determined using an ELISA kit from eBioscience.

Result:

Compound 1 alone promoted IFN-γ releasing from PBMCs in co-culture system at concentration between 10 nM and 100 nM, and suppressed IFN-γ releasing at high concentrations (≥3 μM). Combination of intermediate level Compound 1 and Mab 1 showed significantly enhanced PBMC IFN-γ production, indicating better in vitro T cell activity (FIG. 1).

Example 2

Effect of the Combination of Anti-PD-1 mAb and RAF Inhibitor in a K-Ras Mutation Lung Cancer and B-Raf$^{V600E}$ Mutation Colon Cancer Models in the Presence of in the Presence of Human PBMCs Method On the day of implantation, human peripheral blood mononuclear cells (PBMCs) were isolated from 120 mL blood donated by a healthy volunteer. Briefly, peripheral blood was collected into vacuum blood collection tubes containing sodium heparin. PBMCs were separated by density gradient centrifugation using Histopaque-1077 and washed one time by Dulbecco's Phosphate Buffered Saline (DPBS). The cell pellet was suspended with DPBS at appropriate volume to give a final concentration of $1\times10^8$ cells/ml and placed on ice prior to inoculation. NOD/SCID mice were pre-treated with cyclophosphamide (prepared in saline, 150 mg/kg, i.p.) and disulfiram (prepared in 0.8% Tween-80 in saline, 125 mg/kg, p.o., one hour after each dose of cyclophosphamide) once daily for two days. Animals were then injected with tumor cells or tumor fragments and PBMCs mixture 24 hours after the second dose of cyclophosphamide.

For Calu-6 K-Ras mutation lung cancer model, the cells were cultured in Dulbecco minimum essential medium (DMEM) supplemented with 10% (v/v) fetal bovine serum, and 100 g/ml of penicillin and streptomycin. On the day of implantation, culture medium was replaced with fresh medium. Five hours later, media was removed and cells were collected as described above, except that cells were re-suspended in cold (4° C.) DPBS to give a final concentration of $5\times10^7$ cells/ml and placed on ice prior to inoculation. Mix the Calu-6 cells, PBMCs and matrigel (BD, Cat #356237) at the ratio of 1:1:2. The right axilla region of each mouse was cleaned with 70% ethanol prior to cell inoculation. Each animal was injected subcutaneously with $5\times10^6$ Calu-6 cells and $2.5\times10^6$ PBMC (200 μl cell mixture in 50% matrigel) in the right front flank via a 26-gauge needle.

For B-Raf$^{V600E}$ mutation Colon cancer Patient-derived xenograft (PDX) model, BCCO-028 is derived from tumor tissues surgically removed from a patient with colon cancer. Within 2 to 4 hours following patient surgery, the tumor samples were subcutaneously engrafted into the scapular area of anesthetized NOD/SCID mice. After tumors grew to around 300-1000 mm$^3$, tumors were surgically removed and fragments were passaged in NOD/SCID mice by subsequent engraftments. Animals were then implanted with BCCO-028 tumor fragments and PBMCs 24 hours after the second dose of cyclophosphamide. The right axilla region of each NOD/SCID mouse was cleaned with 70% ethanol prior to tumor fragments inoculation. Each animal was implanted subcutaneously with a fragment (around 3×3×3 mm$^3$) of BCCO-028 colon cancer (passage 5) in the right flank via 14-gauge trocar needle, followed by subcutaneously injection of $5\times10^6$ PBMC in 200 μl of 50% matrigel near the edge of tumor fragment via a 26-gauge needle.

Starting from day 0 after cell or fragment inoculation, animals were randomly assigned into 4 groups with 8-11 mice per group. The groups consisted of a control group (no drug treatment), 5 mg/kg of Compound 1 (based on free-base weight), 10 mg/kg of Mab 1, and the combination of Compound 1 and Mab 1. Treatments were administered in a volume of 10 ml/kg body weight, assessed immediately before dosing and the volume dosed was adjusted accordingly. Compound 1 was administered by oral gavage (p.o.) once daily (QD) and Mab 1 was administered by intraperitoneal (i.p.) injection once weekly (QW). After implantation, primary tumor volume was measured in two dimensions using a calliper.

Individual body weight was recorded twice weekly, with mice being monitored daily for clinical signs of toxicity for the duration of the study. Mice were euthanized using carbon dioxide once their tumor volume reached 2,500 mm$^3$, the tumor was ulcerated, or body weight loss exceeded 20%.

Tumor volume was calculated using the formula: V=0.5× (a×b$^2$) where a and b are the long and short diameters of the tumor, respectively. Tumor growth inhibition (TGI) was calculated using the following formula:

% TGI=100×[1−(treated$_t$/placebo$_t$)]

treated$_t$=treated tumor volume at time t
placebo$_t$=placebo tumor volume at time t Result:

In vivo efficacy of Compound 1 and Mab 1 was examined in BCCO-028 PDX and Calu-6 cells grown subcutaneously in NOD/SCID mice in the presence of human PBMCs.

Figure 2:
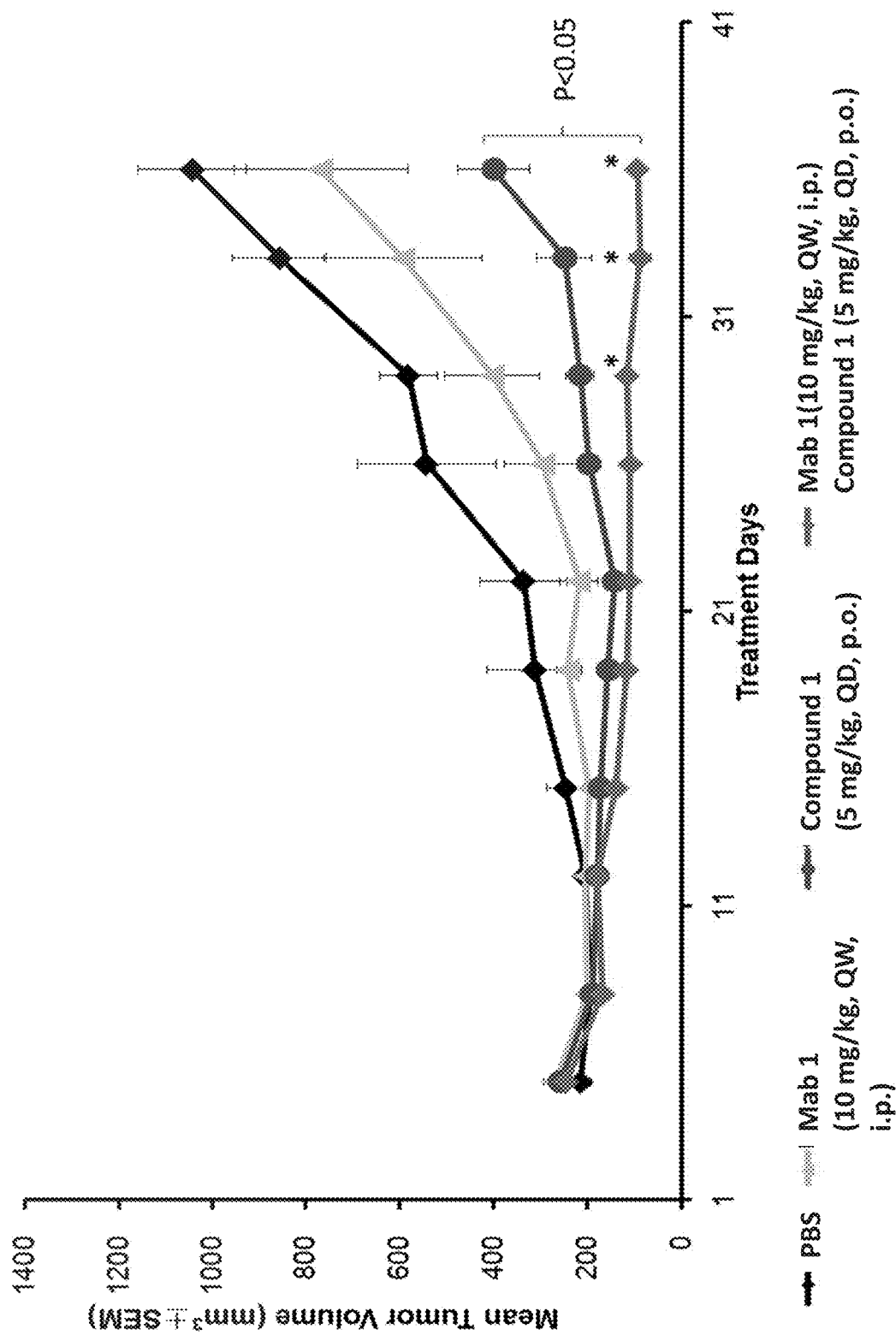
FIG. 2 shows the combination effect of RAF inhibitor and anti-PD-1 mAb on tumor growth in Calu-6 xenograft model in the presence of human PBMCs.
Figure 3:
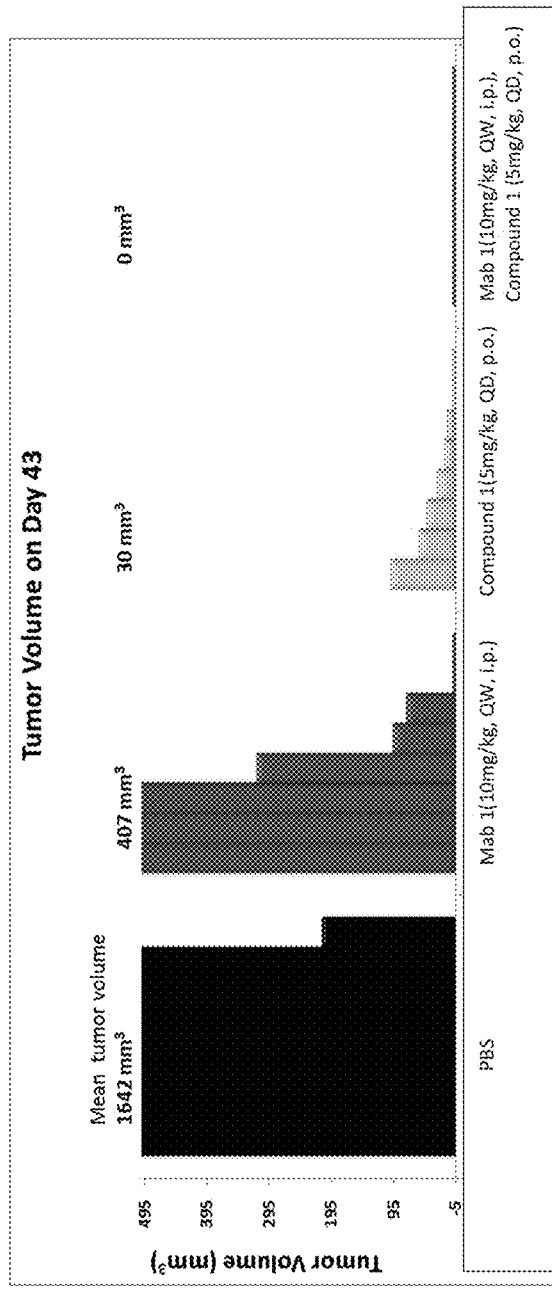
FIG. 3 shows the combination effect of RAF inhibitor and anti-PD-1 mAb on tumor growth in human primary colon cancer BCCO-028 xenograft model in the presence of human PBMCs.

Compound 1 has marked antitumor activity against PDX BCCO-028 colorectal carcinoma (B-Raf$^{V600E}$ mutation) and human Calu-6 lung adenocarcinoma (K-Ras mutation) tumors xenografts in nude mice. In addition, as shown in the figure below, the synergistic efficacy of Compound 1 and Mab 1 is clearly demonstrated by the tumor growth curves in these models. The tumor in the combination-treated group is significantly smaller than either of the monography treatment (FIG. 2, FIG. 3).

The foregoing examples and description of certain embodiments should be taken as illustrating, rather than as limiting the present invention as defined by the claims. As will be readily appreciated, numerous variations and combinations of the features set forth above can be utilized without departing from the present invention as set forth in the claims. All such variations are intended to be included within the scope of the present invention. All references cited are incorporated herein by reference in their entireties.

It is to be understood that, if any prior art publication is referred to herein, such reference does not constitute an admission that the publication forms a part of the common general knowledge in the art in any country.

In the claims which follow and in the preceding description of the invention, except where the context requires otherwise due to express language or necessary implication, the word "comprise" or variations such as "comprises" or "comprising" is used in an inclusive sense, i.e., to specify the presence of the stated features but not to preclude the presence or addition of further features in various embodiments of the invention.

The disclosures of all publications, patents, patent applications and published patent applications referred to herein by an identifying citation are hereby incorporated herein by reference in their entirety.

What is claimed is:

1. A method for the delay of progression or treatment of cancer in a subject, comprising administering to the subject in need thereof a therapeutically effective amount of a PD-1 antagonist in combination with a therapeutically effective amount of a RAF inhibitor,
wherein the cancer is associated with a B-Raf mutation or a K-Ras mutation, wherein the cancer is a lung cancer or a colon cancer;
wherein the PD-1 antagonist is an antibody or an antigen binding fragment thereof, which specifically binds to human PD-1 and which comprises a heavy chain variable region (Vh) and a light chain variable region (Vk), wherein the Vh comprises complementarity determining region (CDR)1, CDR2, and CDR3 comprising SEQ ID NOs: 31, 32, and 33, respectively; and the Vk comprises CDR1, CDR2, CDR3 comprising SEQ ID NO: 34, 35, and 36, respectively; and
wherein the RAF inhibitor is a compound of Formula (I),

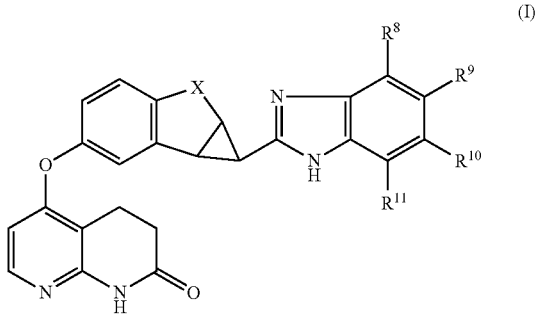

or a stereoisomer thereof, or a pharmaceutically acceptable salt thereof, wherein:
X is selected from $CH_2$ and O;
$R^8$, $R^9$, $R^{10}$ and $R^{11}$, which may be the same or different, are each selected from the group consisting of hydrogen, halogen, alkyl, alkenyl, cycloalkyl, aryl, heterocyclyl, heteroaryl, alkynyl, —$NR^{13}R^{14}$, —$OR^{13}$, —$COR^{13}$, —$CO_2R^{13}$, —$CONR^{13}R^{14}$, —$C(=NR^{13})NR^{14}R^{15}$, —$NR^{13}COR^{14}$, —$NR^{13}CONR^{14}R^{15}$, —$NR^{13}C$ $O_2R^{14}$, —$SO_2R^{13}$, —$SO_2$aryl, —$NR^{13}S$ $O_2NR^{14}R^{15}$, and —$NR^{13}SO_2R^{14}$, wherein the alkyl, alkenyl, alkynyl, cycloalkyl, heteroaryl, aryl, and heterocyclyl are each optionally substituted with at least one substituent $R^{16}$, or ($R^8$ and $R^9$), and/or ($R^9$ and $R^{10}$), and/or ($R^{10}$ and $R^{11}$) together with the ring to which they are attached, form a fused ring selected from the group consisting of heterocyclyl and heteroaryl rings optionally substituted with at least one substituent $R^{16}$;
$R^{13}$, $R^{14}$ and $R^{15}$, which may be the same or different, are each selected from the group consisting of H, haloalkyl, alkyl, alkenyl, alkynyl, cycloalkyl, heterocyclyl, aryl, and heteroaryl; or ($R^{13}$ and $R^{14}$), and/or ($R^{14}$ and $R^{15}$) together with the atom(s) to which they are attached, each form a ring selected from the group consisting of heterocyclyl and heteroaryl rings optionally substituted with at least one substituent $R^{16}$;
$R^{16}$ is selected from the group consisting of halogen, haloalkyl, alkyl, alkenyl, cycloalkyl, aryl, heteroaryl, heterocyclyl, alkynyl, oxo, —CN, —OR', —NR'R", —COR', —$CO_2R'$, —CONR'R", —C(=NR')NR"R''', —NR'COR", —NR'CONR'R", —NR'$CO_2R$", —$SO_2R'$, —$SO_2$aryl, —NR'S $O_2NR"R'''$, —NR'$O_2R"$, and —NR'$SO_2$aryl, wherein R', R", and R''' are independently selected from the group consisting of H, haloalkyl, alkyl, alkenyl, alkynyl, cycloalkyl, heterocyclyl, aryl, and heteroaryl, or (R' and R"), and/or (R" and R''') together with the atoms to which they are attached, form a ring selected from the group consisting of heterocyclyl and heteroaryl rings.

2. The method of claim 1, wherein the heavy chain variable region (Vh) comprises SEQ ID NO: 24 and the light chain variable region (Vk) comprises SEQ ID NO: 26.

3. The method of claim 1, wherein the antibody comprises a IgG4 heavy chain constant domain comprising any of SEQ ID NOs:83-88.

4. The method of claim 1, wherein the antibody fragment is a Fv fragment, F(ab), Fab', or F(ab').

5. The method according to claim 1, wherein the antibody comprises an IgG4 heavy chain constant domain comprising SEQ ID NO: 88, and wherein the heavy chain variable region (Vh) and the light chain variable region (Vk) comprise SEQ ID NO: 24 and SEQ ID NO: 26, respectively.

6. The method of claim 1, wherein $R^8$, $R^9$, $R^{10}$, and $R^{11}$ in Formula (I), which may be the same or different, are each independently selected from the group consisting of alkyl, hydrogen, haloalkyl, halogen, hydroxy, —CN, —Oalkyl, —Ohaloalkyl, and aryl.

7. The method of claim 1, wherein the RAF inhibitor is a compound of Formula (I),

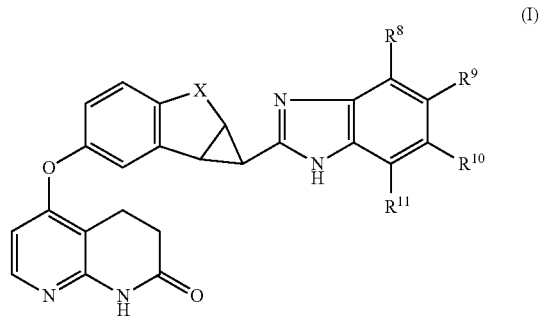

or a stereoisomer thereof, or a pharmaceutically acceptable salt thereof, wherein:

X is selected from the group consisting of $CH_2$ and O;

$R^8$, $R^9$, $R^{10}$ and $R^{11}$, which may be the same or different, are each selected from the group consisting of hydrogen, halogen, alkyl, —CN, cycloalkyl, aryl, heterocyclyl, —$OR^{13}$, and —$CONR^{13}R^{14}$, wherein the alkyl, and aryl are each optionally substituted with at least one substituent $R^{16}$, or ($R^8$ and $R^9$), and/or ($R^9$ and $R^{10}$), and/or ($R^{10}$ and $R^{11}$) together with the ring to which they are attached, form a fused ring selected from cycloalkyl;

$R^{13}$ and $R^{14}$, which may be the same or different, are each selected from the group consisting of H, alkyl, and haloalkyl;

$R^{16}$ is selected from halogen, haloalkyl, and alkyl.

8. The method of claim 1, wherein the RAF inhibitor is a compound of Formula (I),

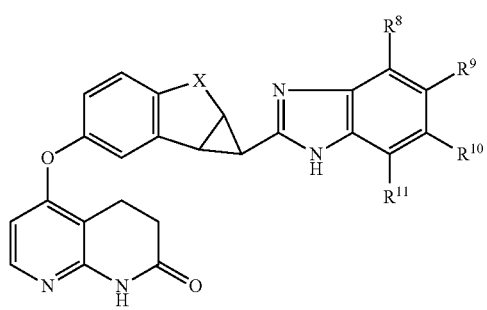

or a stereoisomer thereof, or a pharmaceutically acceptable salt thereof, wherein:

X is selected from the group consisting of $CH_2$ and O;

$R^8$ is selected from the group consisting of H, F, Cl, and Br;

$R^9$ is selected from the group consisting of H, F, Cl, Br, and $C_{1-6}$alkyl;

$R^{10}$ is selected from H, F, Cl, Br, OH, —CN, $C_{1-6}$alkyl, $CF_3$, phenyl, $OC_{1-6}$alkyl, $OC_{1-6}$haloalkyl, and —$CONR^{13}R^{14}$, wherein $R^{13}$ and $R^{14}$ may be the same or different, are each selected from the group consisting of H and $C_{1-6}$alkyl;

$R^{11}$ is selected from the group consisting of H, F, Cl, Br, and $CF_3$;

or ($R^9$ and $R^{10}$) together with the ring to which they are attached, form a fused ring selected from $C_{5-6}$cycloalkyl.

9. The method of claim 1, wherein the cancer is associated with a B-Raf mutation.

10. The method of claim 1, wherein the cancer is associated with a K-Ras mutation.

11. The method of claim 1, wherein the PD-1 antagonist and the RAF inhibitor are administered simultaneously.

12. The method of claim 1, wherein the RAF inhibitor is administered orally at a dose of 5-80 mg QD.

13. The method of claim 1, wherein the PD-1 antagonist is administered parenterally at a dose of 0.5-10 mg/kg QW, or Q2W, or Q3W, or Q4W.

14. The method of claim 1, wherein the PD-1 antagonist is administered at a dose of 0.5-10 mg/kg QW or Q2W or Q3W, and the RAF inhibitor is administered at a dose of 5-80 mg QD.

15. The method of claim 1, wherein the PD-1 antagonist is administered at a dose of 0.5-10 mg/kg QW or Q2W or Q3W, and the RAF inhibitor is administered at a dose of 10-30 mg QD.

16. The method of claim 1, wherein the RAF inhibitor is a compound of Formula (II),

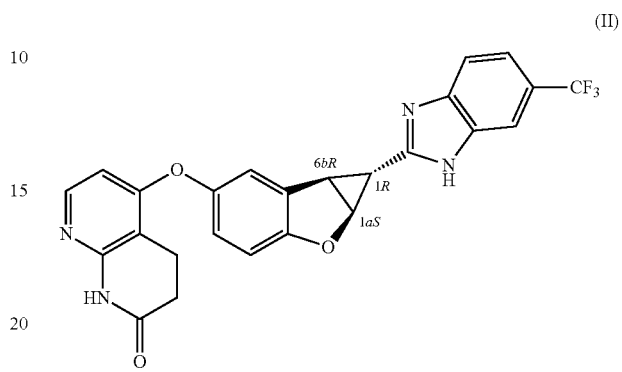

or a pharmaceutically acceptable salt thereof.

17. The method of claim 1, wherein the PD-1 antagonist and the RAF inhibitor are administered sequentially.

18. The method of claim 1, wherein the subject is a human.

19. The method of claim 16, wherein the subject is a human.

20. A method for the delay of progression or treatment of cancer in a subject, comprising administering to the subject in need thereof a therapeutically effective amount of a PD-1 antagonist in combination with a therapeutically effective amount of a RAF inhibitor;

wherein the cancer is associated with a B-Raf mutation or a K-Ras mutation, wherein the cancer is a lung cancer or a colon cancer; and wherein the PD-1 antagonist is an antibody which comprises a heavy chain variable region (Vh), a light chain variable region (Vk), and a IgG4 heavy chain effector or constant domain comprising SEQ ID NO: 88, wherein the heavy chain variable region (Vh) and the light chain variable region (Vk) comprise SEQ ID NO: 24 and SEQ ID NO: 26, respectively; and wherein the RAF inhibitor is the compound of Formula (IIIa)

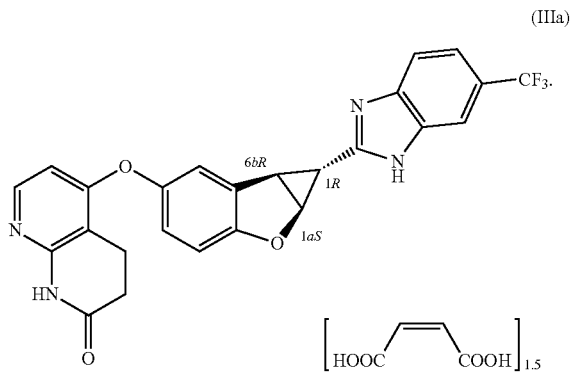

21. The method of claim 20, wherein the subject is a human.

* * * * *

UNITED STATES PATENT AND TRADEMARK OFFICE
CERTIFICATE OF CORRECTION

PATENT NO. : 11,534,431 B2
APPLICATION NO. : 17/099115
DATED : December 27, 2022
INVENTOR(S) : Jing Song et al.

It is certified that error appears in the above-identified patent and that said Letters Patent is hereby corrected as shown below:

In the Claims

In Claim 1, Column 97, Line 56 please replace "-$NR^{13}C\ O_2R^{14}$," with -- -$NR^{13}CO_2R^{14}$,--

In Claim 1, Column 97, Lines 56-57 please replace "-$NR^{13}S\ O_2NR^{14}R^{15}$," with -- -$NR^{13}SO_2NR^{14}R^{15}$,--

In Claim 1, Column 98, Line 23 please replace "-NR'S $O_2$NR"R'"," with -- -NR'$SO_2$NR"R'",--

In Claim 7, Column 99, Line 17 please replace "$R^{16}$ is selected from halogen, haloalkyl, and alkyl." with --$R^{16}$ is selected from the group consisting of halogen, haloalkyl, and alkyl.--

In Claim 8, Column 99, Line 43 please replace "$R^{10}$ is selected from H," with --$R^{10}$ is selected from the group consisting of H,--

Signed and Sealed this
Fourteenth Day of March, 2023

Katherine Kelly Vidal
*Director of the United States Patent and Trademark Office*

SEQUENCE LISTING

<160> NUMBER OF SEQ ID NOS: 90

<210> SEQ ID NO 1
<211> LENGTH: 444
<212> TYPE: DNA
<213> ORGANISM: Homo sapiens

<400> SEQUENCE: 1

```
ccaggatggt tcttagactc cccagacagg ccctggaacc ccccaccttt ctcccagcc      60 ctgctcgtgg tgaccgaagg ggacaacgcc accttcacct gcagcttctc caacacatcg    120
gagagcttcg tgctaaactg gtaccgcatg agccccagca accagacgga caagctggcc    180
gccttccccg aggaccgcag ccagcccggc caggactgcc gcttccgtgt cacacaactg    240
cccaacgggc gtgacttcca catgagcgtg gtcagggccc ggcgcaatga cagcggcacc    300
tacctctgtg gggccatctc cctggccccc aaggcgcaga tcaaagagag cctgcgggca    360
gagctcaggg tgacagagag aaggggcagaa gtgcccacag cccacccag cccctcaccc    420 aggccagccg gccagttcca aacc                                           444
```

<210> SEQ ID NO 2
<211> LENGTH: 148
<212> TYPE: PRT
<213> ORGANISM: Homo sapiens

<400> SEQUENCE: 2

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125
```

Ala Glu Val Pro Thr Ala His Pro Ser Pro Ser Pro Arg Pro Ala Gly
    130                 135                 140

Gln Phe Gln Thr
145

<210> SEQ ID NO 3
<211> LENGTH: 354
<212> TYPE: DNA
<213> ORGANISM: Mus musculus

<400> SEQUENCE: 3
caggtgcagc tgaaggagtc aggacctggc ctggtggcgc cctcaaagaa cctgtccatc    60
acttgcactg tctctgggtt ttcattaacc agctatggtg tacactggat tcgccagcct   120
ccaggaaagg gactggaatg gctgggagta atatgggccg gtggaagcac aaattataat   180
tcggctctca tgtccagact gagcatcagc aaagacaact ccaggagcca gttttctta   240 agaatgaaca gtctgcaaac tgatgacaca gccatgtact actgtgccag agcctatggt   300
aactactggt acatcgatgt ctggggcgca gggaccacgg tcaccgtctc ctca         354

<210> SEQ ID NO 4
<211> LENGTH: 118
<212> TYPE: PRT
<213> ORGANISM: Mus musculus

<400> SEQUENCE: 4

Gln Val Gln Leu Lys Glu Ser Gly Pro Gly Leu Val Ala Pro Ser Lys
1               5                   10                  15

Asn Leu Ser Ile Thr Cys Thr Val Ser Gly Phe Ser Leu Thr Ser Tyr
            20                  25                  30

Gly Val His Trp Ile Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Arg Ser Gln Val Phe Leu
65                  70                  75                  80

Arg Met Asn Ser Leu Gln Thr Asp Asp Thr Ala Met Tyr Tyr Cys Ala
                85                  90                  95

Arg Ala Tyr Gly Asn Tyr Trp Tyr Ile Asp Val Trp Gly Ala Gly Thr
            100                 105                 110

Thr Val Thr Val Ser Ser
        115

<210> SEQ ID NO 5
<211> LENGTH: 321
<212> TYPE: DNA
<213> ORGANISM: Mus musculus

<400> SEQUENCE: 5
gacattgtga tgacccagac tcccaaattc ctgcttgtat cagcaggaga cagggttacc    60
ataacctgca aggccagtca gagtgtgagt aatgatgtag cttggtacca acagaagcca   120
gggcagtctc ctaaactgct gataaactat gcatttcatc gcttcactgg agtccctgat   180
cgtttcactg gcagtggata tgggacggat tcattttca ccatcagcac tgtgcaggct   240
gaagacctgg cagtttattt ctgtcaccag gcttatagtt ctccgtacac gttcggaggg   300
gggaccaagc tggaaatgaa a                                              321

<210> SEQ ID NO 6
<211> LENGTH: 107
<212> TYPE: PRT
<213> ORGANISM: Mus musculus

<400> SEQUENCE: 6

```
Asp Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Asn Tyr Ala Phe His Arg Phe Thr Gly Val Pro Asp Arg Phe Thr Gly
    50                  55                  60

Ser Gly Tyr Gly Thr Asp Phe Ile Phe Thr Ile Ser Thr Val Gln Ala
65                  70                  75                  80

Glu Asp Leu Ala Val Tyr Phe Cys His Gln Ala Tyr Ser Ser Pro Tyr
                85                  90                  95

Thr Phe Gly Gly Gly Thr Lys Leu Glu Met Lys
            100                 105
```

<210> SEQ ID NO 7
<211> LENGTH: 342
<212> TYPE: DNA
<213> ORGANISM: Mus musculus

<400> SEQUENCE: 7

```
cagatccagt tggtgcagtc tggacctgag ctgaagaagc ctggagagac agtcaagatc      60
tcctgcaagg cttctgggta taccttcaca aactatggaa tgaactgggt gaagcaggct     120
ccaggaaagg gtttaaagtg gatgggctgg ataaacaata taatggaga gccaacatat      180 gctgaagagt tcaagggacg gtttgccttc tctttggaaa cctctgccag cactgcctat     240
ttgcagatca acaacctcaa aaatgaggac acggctacat atttctgtgc aagagatgtt     300
atggactatt ggggtcaagg aacctcagtc accgtctcct ca                        342
```

<210> SEQ ID NO 8
<211> LENGTH: 114
<212> TYPE: PRT
<213> ORGANISM: Mus musculus

<400> SEQUENCE: 8

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Asn Asn Gly Glu Pro Thr Tyr Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Asp Val Met Asp Tyr Trp Gly Gln Gly Thr Ser Val Thr Val
            100                 105                 110

Ser Ser
```

<210> SEQ ID NO 9
<211> LENGTH: 330
<212> TYPE: DNA
<213> ORGANISM: Mus musculus

<400> SEQUENCE: 9

```
gacattgtgc tgacccaatc tccagcttct ttggctgtgt ctctagggca gagggccacc    60
atatcctgca gagccagtga aagtgttgat aattatggct atagttttat gcactggtac   120
cagcagaaac caggacagcc accccaactc ctcatctatc gtgcatccaa cctagaatct   180
gggatccctg ccaggttcag tggcagtggg tctaggacag gcttcaccct caccattaat   240
cctgtggagg ctgatgatgt tgcaacctat tactgtcagc aaagtaaaga atatccgacg   300
ttcggtggag gcaccaagct ggaagtcaaa                                     330
```

<210> SEQ ID NO 10
<211> LENGTH: 110
<212> TYPE: PRT
<213> ORGANISM: Mus musculus

<400> SEQUENCE: 10

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

Gln Leu Leu Ile Tyr Arg Ala Ser Asn Leu Glu Ser Gly Ile Pro Ala
    50                  55                  60

Arg Phe Ser Gly Ser Gly Ser Arg Thr Gly Phe Thr Leu Thr Ile Asn
65                  70                  75                  80

Pro Val Glu Ala Asp Asp Val Ala Thr Tyr Tyr Cys Gln Gln Ser Lys
                85                  90                  95

Glu Tyr Pro Thr Phe Gly Gly Gly Thr Lys Leu Glu Val Lys
            100                 105                 110

<210> SEQ ID NO 11
<211> LENGTH: 10
<212> TYPE: PRT
<213> ORGANISM: Mus musculus

<400> SEQUENCE: 11

Gly Phe Ser Leu Thr Ser Tyr Gly Val His
1               5                   10

<210> SEQ ID NO 12
<211> LENGTH: 16
<212> TYPE: PRT
<213> ORGANISM: Mus musculus

<400> SEQUENCE: 12

Val Ile Trp Ala Gly Gly Ser Thr Asn Tyr Asn Ser Ala Leu Met Ser
1               5                   10                  15

<210> SEQ ID NO 13
<211> LENGTH: 12
<212> TYPE: PRT
<213> ORGANISM: Mus musculus

<400> SEQUENCE: 13

Ala Arg Ala Tyr Gly Asn Tyr Trp Tyr Ile Asp Val
1               5                   10

<210> SEQ ID NO 14
<211> LENGTH: 11
<212> TYPE: PRT
<213> ORGANISM: Mus musculus

<400> SEQUENCE: 14

Lys Ala Ser Gln Ser Val Ser Asn Asp Val Ala
1               5                   10

<210> SEQ ID NO 15
<211> LENGTH: 7
<212> TYPE: PRT
<213> ORGANISM: Mus musculus

<400> SEQUENCE: 15

Tyr Ala Phe His Arg Phe Thr
1               5

<210> SEQ ID NO 16
<211> LENGTH: 9
<212> TYPE: PRT
<213> ORGANISM: Mus musculus

<400> SEQUENCE: 16

His Gln Ala Tyr Ser Ser Pro Tyr Thr
1               5

<210> SEQ ID NO 17
<211> LENGTH: 10
<212> TYPE: PRT
<213> ORGANISM: Mus musculus

<400> SEQUENCE: 17

Gly Tyr Thr Phe Thr Asn Tyr Gly Met Asn
1               5                   10

<210> SEQ ID NO 18
<211> LENGTH: 17
<212> TYPE: PRT
<213> ORGANISM: Mus musculus

<400> SEQUENCE: 18

Trp Ile Asn Asn Asn Asn Gly Glu Pro Thr Tyr Ala Glu Glu Phe Lys
1               5                   10                  15

Gly

<210> SEQ ID NO 19
<211> LENGTH: 7
<212> TYPE: PRT
<213> ORGANISM: Mus musculus

<400> SEQUENCE: 19

Ala Arg Asp Val Met Asp Tyr
1               5

<210> SEQ ID NO 20
<211> LENGTH: 15
<212> TYPE: PRT
<213> ORGANISM: Mus musculus

<400> SEQUENCE: 20

Arg Ala Ser Glu Ser Val Asp Asn Tyr Gly Tyr Ser Phe Met His
1               5                   10                  15

<210> SEQ ID NO 21
<211> LENGTH: 7
<212> TYPE: PRT
<213> ORGANISM: Mus musculus

<400> SEQUENCE: 21

Arg Ala Ser Asn Leu Glu Ser
1               5

<210> SEQ ID NO 22
<211> LENGTH: 8
<212> TYPE: PRT
<213> ORGANISM: Mus musculus

<400> SEQUENCE: 22

Gln Gln Ser Lys Glu Tyr Pro Thr
1               5

<210> SEQ ID NO 23
<211> LENGTH: 354
<212> TYPE: DNA
<213> ORGANISM: Artificial Sequence
<220> FEATURE:
<223> OTHER INFORMATION: 317-4B6 cDNA-Vh

<400> SEQUENCE: 23
caggtgcagc tgcaggagtc gggaccagga ctggtgaagc cttcggagac cctgtccctc      60
acctgcactg tctctgggtt ttcattaacc agctatggtg tacactggat ccggcagccc     120
ccagggaagg gactggagtg gatcggggtc atatacgccg atggaagcac aaattataat     180
ccctccctca gagtcgagt gaccatatca aagacacct ccaagaacca ggtttccctg       240
aagctgagct ctgtgaccgc tgcggacacg gccgtgtatt actgtgcgag agcctatggt     300
aactactggt acatcgatgt ctggggccaa gggaccacgg tcaccgtctc ctca           354

<210> SEQ ID NO 24
<211> LENGTH: 118
<212> TYPE: PRT
<213> ORGANISM: Artificial Sequence
<220> FEATURE:
<223> OTHER INFORMATION: 317-4B6 pro-Vh

<400> SEQUENCE: 24

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
                20                  25                  30

Gly Val His Trp Ile Arg Gln Pro Pro Gly Lys Gly Leu Glu Trp Ile
            35                  40                  45

Gly Val Ile Tyr Ala Asp Gly Ser Thr Asn Tyr Asn Pro Ser Leu Lys
        50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 25
<211> LENGTH: 321
<212> TYPE: DNA
<213> ORGANISM: Artificial Sequence
<220> FEATURE:
<223> OTHER INFORMATION: 317-4B6 cDNA-Vk

<400> SEQUENCE: 25

```
gacatcgtga tgacccagtc tccagactcc ctggctgtgt ctctgggcga gagggccacc    60
atcaactgca gtccagcga gagtgtgagt aatgatgtag cttggtacca gcagaaacca   120
ggacagcctc ctaagctgct cattaactat gcatttcatc gcttcactgg ggtccctgac   180
cgattcagtg gcagcgggta tgggacagat ttcactctca ccatcagcag cctgcaggct   240
gaagatgtgg cagtttatta ctgtcaccag gcttatagtt ctccgtacac gtttggccag   300
gggaccaagc tggagatcaa a                                             321
```

<210> SEQ ID NO 26
<211> LENGTH: 107
<212> TYPE: PRT
<213> ORGANISM: Artificial Sequence
<220> FEATURE:
<223> OTHER INFORMATION: 317-4B6 pro-Vk

<400> SEQUENCE: 26

Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Val Ser Asn Asp
            20                  25                  30

Val Ala Trp Tyr Gln Gln Lys Pro Gly Gln Pro Pro Lys Leu Leu Ile
        35                  40                  45

Asn Tyr Ala Phe His Arg Phe Thr Gly Val Pro Asp Arg Phe Ser Gly
    50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys His Gln Ala Tyr Ser Ser Pro Tyr
                85                  90                  95

Thr Phe Gly Gln Gly Thr Lys Leu Glu Ile Lys
            100                 105

<210> SEQ ID NO 27
<211> LENGTH: 342
<212> TYPE: DNA
<213> ORGANISM: Artificial Sequence
<220> FEATURE:
<223> OTHER INFORMATION: 326-4A3 cDNA-Vh

<400> SEQUENCE: 27

```
caggtgcagc tggtgcagag cggcagcgag ctgaagaagc ccggcgccag cgtgaaggtg    60
agctgcaagg ccagcggcta caccttcacc aactacggca tgaactgggt gagacaggcc   120
cccggccagg gcctgaagtg gatgggctgg atcaacaaca acaacgccga gcccacctac   180
gcccaggact tcagaggcag attcgtgttc agcctggaca ccagcgccag caccgcctac   240
ctgcagatca gcagcctgaa gaccgaggac accgccgtgt actactgcgc cagagacgtg   300
atggactact ggggccaggg caccctggtg accgtgagcg gc                      342
```

```
<210> SEQ ID NO 28
<211> LENGTH: 114
<212> TYPE: PRT
<213> ORGANISM: Artificial Sequence
<220> FEATURE:
<223> OTHER INFORMATION: 326-4A3 pro-Vh

<400> SEQUENCE: 28

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Asn Asn Asn Ala Glu Pro Thr Tyr Ala Gln Asp Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Leu Val Thr Val
            100                 105                 110

Ser Ser

<210> SEQ ID NO 29
<211> LENGTH: 330
<212> TYPE: DNA
<213> ORGANISM: Artificial Sequence
<220> FEATURE:
<223> OTHER INFORMATION: 326-4A3 cDNA-Vk

<400> SEQUENCE: 29
gacattgtgc tgacccagtc tccagcctcc ttggccgtgt ctccaggaca gagggccacc      60
atcacctgca gagccagtga aagtgttgat aattatggct atagttttat gcactggtat     120
cagcagaaac caggacaacc tcctaaactc ctgatttacc gtgcatccaa cctagaatct     180
ggggtcccag ccaggttcag cggcagtggg tctgggaccg atttcaccct cacaattaat     240
cctgtggaag ctgaggatac tgcaaattat tactgtcagc aaagtaaaga atatccgacg     300
ttcggcggag ggaccaaggt ggagatcaaa                                      330

<210> SEQ ID NO 30
<211> LENGTH: 110
<212> TYPE: PRT
<213> ORGANISM: Artificial Sequence
<220> FEATURE:
<223> OTHER INFORMATION: 326-4A3 pro-Vk

<400> SEQUENCE: 30

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80
```

Pro Val Glu Ala Glu Asp Thr Ala Asn Tyr Tyr Cys Gln Gln Ser Lys
                85                  90                  95
Glu Tyr Pro Thr Phe Gly Gly Gly Thr Lys Val Glu Ile Lys
            100                 105                 110

<210> SEQ ID NO 31
<211> LENGTH: 10
<212> TYPE: PRT
<213> ORGANISM: Mus musculus

<400> SEQUENCE: 31

Gly Phe Ser Leu Thr Ser Tyr Gly Val His
1               5                   10

<210> SEQ ID NO 32
<211> LENGTH: 16
<212> TYPE: PRT
<213> ORGANISM: Artificial Sequence
<220> FEATURE:
<223> OTHER INFORMATION: 317-4B6 H-CDR2 or CDR-H2

<400> SEQUENCE: 32

Val Ile Tyr Ala Asp Gly Ser Thr Asn Tyr Asn Pro Ser Leu Lys Ser
1               5                   10                  15

<210> SEQ ID NO 33
<211> LENGTH: 12
<212> TYPE: PRT
<213> ORGANISM: Mus musculus

<400> SEQUENCE: 33

Ala Arg Ala Tyr Gly Asn Tyr Trp Tyr Ile Asp Val
1               5                   10

<210> SEQ ID NO 34
<211> LENGTH: 11
<212> TYPE: PRT
<213> ORGANISM: Artificial Sequence
<220> FEATURE:
<223> OTHER INFORMATION: 317-4B6 L-CDR1 or CDR-L1

<400> SEQUENCE: 34

Lys Ser Ser Glu Ser Val Ser Asn Asp Val Ala
1               5                   10

<210> SEQ ID NO 35
<211> LENGTH: 7
<212> TYPE: PRT
<213> ORGANISM: Mus musculus

<400> SEQUENCE: 35

Tyr Ala Phe His Arg Phe Thr
1               5

<210> SEQ ID NO 36
<211> LENGTH: 9
<212> TYPE: PRT
<213> ORGANISM: Mus musculus

<400> SEQUENCE: 36

His Gln Ala Tyr Ser Ser Pro Tyr Thr
1               5

<210> SEQ ID NO 37
<211> LENGTH: 10

```
<212> TYPE: PRT
<213> ORGANISM: Mus musculus

<400> SEQUENCE: 37

Gly Tyr Thr Phe Thr Asn Tyr Gly Met Asn
1               5                   10

<210> SEQ ID NO 38
<211> LENGTH: 17
<212> TYPE: PRT
<213> ORGANISM: Artificial Sequence
<220> FEATURE:
<223> OTHER INFORMATION: 326-4A3 H-CDR2 or CDR-H2

<400> SEQUENCE: 38

Trp Ile Asn Asn Asn Ala Glu Pro Thr Tyr Ala Gln Asp Phe Arg
1               5                   10                  15

Gly

<210> SEQ ID NO 39
<211> LENGTH: 7
<212> TYPE: PRT
<213> ORGANISM: Mus musculus

<400> SEQUENCE: 39

Ala Arg Asp Val Met Asp Tyr
1               5

<210> SEQ ID NO 40
<211> LENGTH: 15
<212> TYPE: PRT
<213> ORGANISM: Mus musculus

<400> SEQUENCE: 40

Arg Ala Ser Glu Ser Val Asp Asn Tyr Gly Tyr Ser Phe Met His
1               5                   10                  15

<210> SEQ ID NO 41
<211> LENGTH: 7
<212> TYPE: PRT
<213> ORGANISM: Mus musculus

<400> SEQUENCE: 41

Arg Ala Ser Asn Leu Glu Ser
1               5

<210> SEQ ID NO 42
<211> LENGTH: 8
<212> TYPE: PRT
<213> ORGANISM: Mus musculus

<400> SEQUENCE: 42

Gln Gln Ser Lys Glu Tyr Pro Thr
1               5

<210> SEQ ID NO 43
<211> LENGTH: 118
<212> TYPE: PRT
<213> ORGANISM: Artificial Sequence
<220> FEATURE:
<223> OTHER INFORMATION: 317-4B2 pro-Vh

<400> SEQUENCE: 43

Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Phe Ser Leu Thr Ser Tyr
            20                  25                  30

Gly Val His Trp Ile Arg Gln Pro Gly Lys Gly Leu Glu Trp Ile
            35                  40              45

Gly Val Ile Tyr Ala Gly Gly Ser Thr Asn Tyr Asn Pro Ser Leu Lys
        50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
            115

<210> SEQ ID NO 44
<211> LENGTH: 107
<212> TYPE: PRT
<213> ORGANISM: Artificial Sequence
<220> FEATURE:
<223> OTHER INFORMATION: 317-4B2 pro-Vk

<400> SEQUENCE: 44

Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Val Ser Asn Asp
            20                  25                  30

Val Ala Trp Tyr Gln Gln Lys Pro Gly Gln Pro Pro Lys Leu Leu Ile
            35                  40                  45

Asn Tyr Ala Phe His Arg Phe Thr Gly Val Pro Asp Arg Phe Ser Gly
        50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys His Gln Ala Tyr Ser Ser Pro Tyr
                85                  90                  95

Thr Phe Gly Gln Gly Thr Lys Leu Glu Ile Lys
            100                 105

<210> SEQ ID NO 45
<211> LENGTH: 118
<212> TYPE: PRT
<213> ORGANISM: Artificial Sequence
<220> FEATURE:
<223> OTHER INFORMATION: 317-4B5 pro-Vh

<400> SEQUENCE: 45

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
            35                  40                  45

Gly Val Ile Tyr Ala Gly Gly Ser Thr Asn Tyr Asn Pro Ser Leu Lys
        50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
```

```
                    85                  90                  95
Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 46
<211> LENGTH: 107
<212> TYPE: PRT
<213> ORGANISM: Artificial Sequence
<220> FEATURE:
<223> OTHER INFORMATION: 317-4B5 pro-Vk

<400> SEQUENCE: 46

Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Val Ser Asn Asp
            20                  25                  30

Val Ala Trp Tyr Gln Gln Lys Pro Gly Gln Pro Pro Lys Leu Leu Ile
        35                  40                  45

Asn Tyr Ala Phe His Arg Phe Thr Gly Val Pro Asp Arg Phe Ser Gly
    50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys His Gln Ala Tyr Ser Ser Pro Tyr
                85                  90                  95

Thr Phe Gly Gln Gly Thr Lys Leu Glu Ile Lys
            100                 105

<210> SEQ ID NO 47
<211> LENGTH: 354
<212> TYPE: DNA
<213> ORGANISM: Artificial Sequence
<220> FEATURE:
<223> OTHER INFORMATION: 317-1 cDNA-Vh

<400> SEQUENCE: 47
caggtgcagc tgcaggagtc gggaccagga ctggtgaagc cttcggagac cctgtccctc      60
acctgcactg tctctggggtt ttcattaacc agctatggtg tacactggat ccggcagccc    120
ccagggaagg gactggagtg gctggggggtc atatgggccg gtggaagcac aaattataat    180
ccctccctca agagtcgact gaccatatca aagacaact ccaagagcca ggtttccctg      240
aagatgagct ctgtgaccgc tgcggacacg gccgtgtatt actgtgcgag agcctatggt    300
aactactggt acatcgatgt ctggggccaa gggaccacgg tcaccgtctc ctca            354

<210> SEQ ID NO 48
<211> LENGTH: 118
<212> TYPE: PRT
<213> ORGANISM: Artificial Sequence
<220> FEATURE:
<223> OTHER INFORMATION: 317-1 pro-Vh

<400> SEQUENCE: 48

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Leu
        35                  40                  45
```

Gly Val Ile Trp Ala Gly Ser Thr Asn Tyr Asn Pro Ser Leu Lys
50               55                  60

Ser Arg Leu Thr Ile Ser Lys Asp Asn Ser Lys Ser Gln Val Ser Leu
65                  70                  75                  80

Lys Met Ser Ser Val Thr Ala Ala Asp Thr Ala Val Tyr Tyr Cys Ala
                85                  90                  95

Arg Ala Tyr Gly Asn Tyr Trp Tyr Ile Asp Val Trp Gly Gln Gly Thr
            100                 105                 110

Thr Val Thr Val Ser Ser
        115

<210> SEQ ID NO 49
<211> LENGTH: 321
<212> TYPE: DNA
<213> ORGANISM: Artificial Sequence
<220> FEATURE:
<223> OTHER INFORMATION: 317-1 cDNA-Vk

<400> SEQUENCE: 49
gacatcgtga tgacccagtc tccagactcc ctggctgtgt ctctgggcga gagggccacc    60
atcaactgca aggccagcca gagtgtgagt aatgatgtag cttggtacca gcagaaacca   120
ggacagcctc ctaagctgct cattaactat gcatttcatc gcttcactgg ggtccctgac   180
cgattcagtg gcagcgggta tgggacagat ttcactctca ccatcagcag cctgcaggct   240
gaagatgtgg cagtttatta ctgtcaccag gcttatagtt ctccgtacac gtttggcggg   300
gggaccaagc tggagatcaa a                                             321

<210> SEQ ID NO 50
<211> LENGTH: 107
<212> TYPE: PRT
<213> ORGANISM: Artificial Sequence
<220> FEATURE:
<223> OTHER INFORMATION: 317-1 pro-Vk

<400> SEQUENCE: 50

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Ser Asn Asp
                20                  25                  30

Val Ala Trp Tyr Gln Gln Lys Pro Gly Gln Pro Pro Lys Leu Leu Ile
            35                  40                  45

Asn Tyr Ala Phe His Arg Phe Thr Gly Val Pro Asp Arg Phe Ser Gly
50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys His Gln Ala Tyr Ser Ser Pro Tyr
                85                  90                  95

Thr Phe Gly Gly Gly Thr Lys Leu Glu Ile Lys
            100                 105

<210> SEQ ID NO 51
<211> LENGTH: 114
<212> TYPE: PRT
<213> ORGANISM: Artificial Sequence
<220> FEATURE:
<223> OTHER INFORMATION: 326-3B1 pro-Vh

<400> SEQUENCE: 51

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Asn Asn Gly Glu Pro Thr Tyr Ala Gln Asp Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Leu Val Thr Val
            100                 105                 110

Ser Ser

<210> SEQ ID NO 52
<211> LENGTH: 110
<212> TYPE: PRT
<213> ORGANISM: Artificial Sequence
<220> FEATURE:
<223> OTHER INFORMATION: 326-3B1 pro-Vk

<400> SEQUENCE: 52

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Arg Thr Asp Phe Thr Leu Thr Ile Asn
65                  70                  75                  80

Pro Val Glu Ala Asn Asp Thr Ala Asn Tyr Tyr Cys Gln Gln Ser Lys
                85                  90                  95

Glu Tyr Pro Thr Phe Gly Gly Gly Thr Lys Val Glu Ile Lys
            100                 105                 110

<210> SEQ ID NO 53
<211> LENGTH: 114
<212> TYPE: PRT
<213> ORGANISM: Artificial Sequence
<220> FEATURE:
<223> OTHER INFORMATION: 326-3G1 pro-Vh

<400> SEQUENCE: 53

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Asn Asn Gly Glu Pro Thr Tyr Ala Gln Asp Phe
    50                  55                  60

Arg Gly Arg Phe Val Phe Ser Leu Asp Thr Ser Ala Ser Thr Ala Tyr
65                  70                  75                  80
```

-continued

Leu Gln Ile Ser Ser Leu Lys Thr Glu Asp Thr Ala Val Tyr Tyr Cys
            85                  90                  95

Ala Arg Asp Val Met Asp Tyr Trp Gly Gln Gly Thr Leu Val Thr Val
        100                 105                 110

Ser Ser

<210> SEQ ID NO 54
<211> LENGTH: 110
<212> TYPE: PRT
<213> ORGANISM: Artificial Sequence
<220> FEATURE:
<223> OTHER INFORMATION: 326-3G1 pro-Vk

<400> SEQUENCE: 54

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
50                  55                  60

Arg Phe Ser Gly Ser Gly Ser Arg Thr Asp Phe Thr Leu Thr Ile Asn
65                  70                  75                  80

Pro Val Glu Ala Asn Asp Thr Ala Asn Tyr Tyr Cys Gln Gln Ser Lys
            85                  90                  95

Glu Tyr Pro Thr Phe Gly Gly Thr Lys Val Glu Ile Lys
        100                 105                 110

<210> SEQ ID NO 55
<211> LENGTH: 342
<212> TYPE: DNA
<213> ORGANISM: Artificial Sequence
<220> FEATURE:
<223> OTHER INFORMATION: 326-1 cDNA-Vh

<400> SEQUENCE: 55
caggtgcagc tggtgcagag cggcagcgag ctgaagaagc ccggcgccag cgtgaaggtg      60
agctgcaagg ccagcggcta caccttcacc aactacggca tgaactgggt gagacaggcc     120
cccggccagg gcctggagtg gatgggctgg atcaacaaca caacggcga gcccacctac      180 gcccagggct tcagaggcag attcgtgttc agcctggaca ccagcgccag caccgcctac     240
ctgcagatca gcagcctgaa gaccgaggac accgccgtgt acttctgcgc cagagacgtg     300
atggactact ggggccaggg caccaccgtg accgtgagca gc                        342

<210> SEQ ID NO 56
<211> LENGTH: 114
<212> TYPE: PRT
<213> ORGANISM: Artificial Sequence
<220> FEATURE:
<223> OTHER INFORMATION: 326-1 pro-Vh

<400> SEQUENCE: 56

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Asn Asn Gly Glu Pro Thr Tyr Ala Gln Gly Phe
            50                  55                  60

Arg Gly Arg Phe Val Phe Ser Leu Asp Thr Ser Ala Ser Thr Ala Tyr
 65                  70                  75                  80

Leu Gln Ile Ser Ser Leu Lys Thr Glu Asp Thr Ala Val Tyr Phe Cys
                 85                  90                  95

Ala Arg Asp Val Met Asp Tyr Trp Gly Gln Gly Thr Thr Val Thr Val
                100                 105                 110

Ser Ser

<210> SEQ ID NO 57
<211> LENGTH: 330
<212> TYPE: DNA
<213> ORGANISM: Artificial Sequence
<220> FEATURE:
<223> OTHER INFORMATION: 326-1 cDNA-Vk

<400> SEQUENCE: 57
gacattgtgc tgacccagtc tccagcctcc ttggccgtgt ctccaggaca gagggccacc      60
atcacctgca gagccagtga aagtgttgat aattatggct atagttttat gcactggtat     120
cagcagaaac caggacaacc tcctaaactc ctgatttacc gtgcatccaa cctagaatct     180
ggggtcccag ccaggttcag cggcagtggg tctaggaccg atttcaccct cacaattaat     240
cctgtggaag ctaatgatac tgcaaattat tactgtcagc aaagtaaaga atatccgacg     300
ttcggcggag ggaccaaggt ggagatcaaa                                      330

<210> SEQ ID NO 58
<211> LENGTH: 110
<212> TYPE: PRT
<213> ORGANISM: Artificial Sequence
<220> FEATURE:
<223> OTHER INFORMATION: 326-1 pro-Vk

<400> SEQUENCE: 58

Asp Ile Val Leu Thr Gln Ser Pro Ala Ser Leu Ala Val Ser Pro Gly
 1               5                  10                  15

Gln Arg Ala Thr Ile Thr Cys Arg Ala Ser Glu Ser Val Asp Asn Tyr
                 20                  25                  30

Gly Tyr Ser Phe Met His Trp Tyr Gln Gln Lys Pro Gly Gln Pro Pro
             35                  40                  45

Lys Leu Leu Ile Tyr Arg Ala Ser Asn Leu Glu Ser Gly Val Pro Ala
 50                  55                  60

Arg Phe Ser Gly Ser Gly Ser Arg Thr Asp Phe Thr Leu Thr Ile Asn
 65                  70                  75                  80

Pro Val Glu Ala Asn Asp Thr Ala Asn Tyr Tyr Cys Gln Gln Ser Lys
                 85                  90                  95

Glu Tyr Pro Thr Phe Gly Gly Gly Thr Lys Val Glu Ile Lys
                100                 105                 110

<210> SEQ ID NO 59
<211> LENGTH: 16
<212> TYPE: PRT
<213> ORGANISM: Artificial Sequence
<220> FEATURE:
<223> OTHER INFORMATION: 317-1 H-CDR2 or CDR-H2

<400> SEQUENCE: 59

Val Ile Trp Ala Gly Gly Ser Thr Asn Tyr Asn Pro Ser Leu Lys Ser

```
<210> SEQ ID NO 60
<211> LENGTH: 16
<212> TYPE: PRT
<213> ORGANISM: Artificial Sequence
<220> FEATURE:
<223> OTHER INFORMATION: 317-4B2 H-CDR2 or CDR-H2

<400> SEQUENCE: 60

Val Ile Tyr Ala Gly Gly Ser Thr Asn Tyr Asn Pro Ser Leu Lys Ser
1               5                   10                  15

<210> SEQ ID NO 61
<211> LENGTH: 11
<212> TYPE: PRT
<213> ORGANISM: Artificial Sequence
<220> FEATURE:
<223> OTHER INFORMATION: 317-4B2 L-CDR1 or CDR-L1

<400> SEQUENCE: 61

Lys Ser Ser Glu Ser Val Ser Asn Asp Val Ala
1               5                   10

<210> SEQ ID NO 62
<211> LENGTH: 17
<212> TYPE: PRT
<213> ORGANISM: Artificial Sequence
<220> FEATURE:
<223> OTHER INFORMATION: 326-1 H-CDR2 or CDR-H2

<400> SEQUENCE: 62

Trp Ile Asn Asn Asn Asn Gly Glu Pro Thr Tyr Ala Gln Gly Phe Arg
1               5                   10                  15

Gly

<210> SEQ ID NO 63
<211> LENGTH: 17
<212> TYPE: PRT
<213> ORGANISM: Artificial Sequence
<220> FEATURE:
<223> OTHER INFORMATION: 326-3G1 H-CDR2 or CDR-H2

<400> SEQUENCE: 63

Trp Ile Asn Asn Asn Asn Gly Glu Pro Thr Tyr Ala Gln Asp Phe Arg
1               5                   10                  15

Gly

<210> SEQ ID NO 64
<211> LENGTH: 118
<212> TYPE: PRT
<213> ORGANISM: Artificial Sequence
<220> FEATURE:
<223> OTHER INFORMATION: 317-3A1 pro-Vh

<400> SEQUENCE: 64

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Ala Gly Gly Ser Thr Asn Tyr Asn Pro Ser Leu Lys
    50                  55                  60
```

```
Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Tyr Gly Asn Tyr Trp Tyr Ile Asp Val Trp Gly Gln Gly Thr
            100                 105                 110

Thr Val Thr Val Ser Ser
        115
```

<210> SEQ ID NO 65
<211> LENGTH: 118
<212> TYPE: PRT
<213> ORGANISM: Artificial Sequence
<220> FEATURE:
<223> OTHER INFORMATION: 317-3C1 pro-Vh

<400> SEQUENCE: 65

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Phe Ser Leu Thr Ser Tyr
                 20                  25                  30

Gly Val His Trp Ile Arg Gln Pro Pro Gly Lys Gly Leu Glu Trp Leu
             35                  40                  45

Gly Val Ile Trp Ala Gly Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Tyr Gly Asn Tyr Trp Tyr Ile Asp Val Trp Gly Gln Gly Thr
            100                 105                 110

Thr Val Thr Val Ser Ser
        115
```

<210> SEQ ID NO 66
<211> LENGTH: 118
<212> TYPE: PRT
<213> ORGANISM: Artificial Sequence
<220> FEATURE:
<223> OTHER INFORMATION: 317-3E1 pro-Vh

<400> SEQUENCE: 66

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Phe Ser Leu Thr Ser Tyr
                 20                  25                  30

Gly Val His Trp Ile Arg Gln Pro Pro Gly Lys Gly Leu Glu Trp Ile
             35                  40                  45

Gly Val Ile Trp Ala Gly Gly Ser Thr Asn Tyr Asn Pro Ser Leu Lys
     50                  55                  60

Ser Arg Val Thr Ile Ser Val Asp Thr Ser Lys Ser Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Tyr Gly Asn Tyr Trp Tyr Ile Asp Val Trp Gly Gln Gly Thr
            100                 105                 110

Thr Val Thr Val Ser Ser
```

<210> SEQ ID NO 67
<211> LENGTH: 118
<212> TYPE: PRT
<213> ORGANISM: Artificial Sequence
<220> FEATURE:
<223> OTHER INFORMATION: 317-3F1 pro-Vh

<400> SEQUENCE: 67

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Phe Ser Leu Thr Ser Tyr
            20                  25                  30
Gly Val His Trp Ile Arg Gln Pro Pro Gly Lys Gly Leu Glu Trp Ile
        35                  40                  45
Gly Val Ile Trp Ala Gly Gly Ser Thr Asn Tyr Asn Pro Ser Leu Lys
    50                  55                  60
Ser Arg Val Thr Ile Ser Val Asp Thr Ser Lys Asn Gln Val Ser Leu
65                  70                  75                  80
Lys Leu Ser Ser Val Thr Ala Ala Asp Thr Ala Val Tyr Tyr Cys Ala
                85                  90                  95
Arg Ala Tyr Gly Asn Tyr Trp Tyr Ile Asp Val Trp Gly Gln Gly Thr
            100                 105                 110
Thr Val Thr Val Ser Ser
        115
```

<210> SEQ ID NO 68
<211> LENGTH: 118
<212> TYPE: PRT
<213> ORGANISM: Artificial Sequence
<220> FEATURE:
<223> OTHER INFORMATION: 317-3G1 pro-Vh

<400> SEQUENCE: 68

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Phe Ser Leu Thr Ser Tyr
            20                  25                  30
Gly Val His Trp Ile Arg Gln Pro Pro Gly Lys Gly Leu Glu Trp Ile
        35                  40                  45
Gly Val Ile Trp Ala Gly Gly Ser Thr Asn Tyr Asn Pro Ser Leu Lys
    50                  55                  60
Ser Arg Val Thr Ile Ser Val Asp Thr Ser Lys Ser Gln Val Ser Leu
65                  70                  75                  80
Lys Leu Ser Ser Val Thr Ala Ala Asp Thr Ala Val Tyr Tyr Cys Ala
                85                  90                  95
Arg Ala Tyr Gly Asn Tyr Trp Tyr Ile Asp Val Trp Gly Gln Gly Thr
            100                 105                 110
Thr Val Thr Val Ser Ser
        115
```

<210> SEQ ID NO 69
<211> LENGTH: 118
<212> TYPE: PRT
<213> ORGANISM: Artificial Sequence
<220> FEATURE:
<223> OTHER INFORMATION: 317-3H1 pro-Vh

<400> SEQUENCE: 69

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Thr Ser Tyr
                20                  25                  30

Gly Val His Trp Ile Arg Gln Pro Pro Gly Lys Gly Leu Glu Trp Ile
             35                  40                  45

Gly Val Ile Trp Ala Gly Gly Ser Thr Asn Tyr Asn Pro Ser Leu Lys
         50                  55                  60

Ser Arg Val Thr Ile Ser Lys Asp Thr Ser Lys Ser Gln Val Ser Leu
 65                  70                  75                  80

Lys Leu Ser Ser Val Thr Ala Ala Asp Thr Ala Val Tyr Tyr Cys Ala
                 85                  90                  95

Arg Ala Tyr Gly Asn Tyr Trp Tyr Ile Asp Val Trp Gly Gln Gly Thr
                100                 105                 110

Thr Val Thr Val Ser Ser
            115
```

<210> SEQ ID NO 70
<211> LENGTH: 118
<212> TYPE: PRT
<213> ORGANISM: Artificial Sequence
<220> FEATURE:
<223> OTHER INFORMATION: 317-3I1 pro-Vh

<400> SEQUENCE: 70

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Thr Ser Tyr
                20                  25                  30

Gly Val His Trp Ile Arg Gln Pro Pro Gly Lys Gly Leu Glu Trp Ile
             35                  40                  45

Gly Val Ile Trp Ala Gly Gly Ser Thr Asn Tyr Asn Pro Ser Leu Lys
         50                  55                  60

Ser Arg Val Thr Ile Ser Lys Asp Thr Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95

Arg Ala Tyr Gly Asn Tyr Trp Tyr Ile Asp Val Trp Gly Gln Gly Thr
                100                 105                 110

Thr Val Thr Val Ser Ser
            115
```

<210> SEQ ID NO 71
<211> LENGTH: 118
<212> TYPE: PRT
<213> ORGANISM: Artificial Sequence
<220> FEATURE:
<223> OTHER INFORMATION: 317-4B1 pro-Vh

<400> SEQUENCE: 71

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Thr Ser Tyr
                20                  25                  30

Gly Val His Trp Ile Arg Gln Pro Pro Gly Lys Gly Leu Glu Trp Ile
             35                  40                  45

Gly Val Ile Trp Ala Gly Gly Ser Thr Asn Tyr Asn Pro Ser Leu Lys
```

```
                    50                  55                  60
Ser Arg Val Thr Ile Ser Lys Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Tyr Gly Asn Tyr Trp Tyr Ile Asp Val Trp Gly Gln Gly Thr
                100                 105                 110

Thr Val Thr Val Ser Ser
            115

<210> SEQ ID NO 72
<211> LENGTH: 118
<212> TYPE: PRT
<213> ORGANISM: Artificial Sequence
<220> FEATURE:
<223> OTHER INFORMATION: 317-4B3 pro-Vh

<400> SEQUENCE: 72

Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Thr Ser Tyr
                 20                  25                  30

Gly Val His Trp Ile Arg Gln Pro Pro Gly Lys Gly Leu Glu Trp Ile
             35                  40                  45

Gly Val Ile Asn Ala Gly Gly Ser Thr Asn Tyr Asn Pro Ser Leu Lys
         50                  55                  60

Ser Arg Val Thr Ile Ser Lys Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Tyr Gly Asn Tyr Trp Tyr Ile Asp Val Trp Gly Gln Gly Thr
                100                 105                 110

Thr Val Thr Val Ser Ser
            115

<210> SEQ ID NO 73
<211> LENGTH: 118
<212> TYPE: PRT
<213> ORGANISM: Artificial Sequence
<220> FEATURE:
<223> OTHER INFORMATION: 317-4B4 pro-Vh

<400> SEQUENCE: 73

Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Thr Ser Tyr
                 20                  25                  30

Gly Val His Trp Ile Arg Gln Pro Pro Gly Lys Gly Leu Glu Trp Ile
             35                  40                  45

Gly Val Ile Trp Ala Gly Gly Ser Thr Asn Tyr Asn Pro Ser Leu Lys
         50                  55                  60

Ser Arg Val Thr Ile Ser Lys Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Tyr Gly Asn Tyr Pro Tyr Ile Asp Val Trp Gly Gln Gly Thr
                100                 105                 110
```

Thr Val Thr Val Ser Ser
        115

<210> SEQ ID NO 74
<211> LENGTH: 107
<212> TYPE: PRT
<213> ORGANISM: Artificial Sequence
<220> FEATURE:
<223> OTHER INFORMATION: 317-4A2 pro-Vk

<400> SEQUENCE: 74

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Ser Asn Asp
            20                  25                  30

Val Ala Trp Tyr Gln Gln Lys Pro Gly Gln Pro Pro Lys Leu Leu Ile
        35                  40                  45

Asn Tyr Ala Phe His Arg Phe Thr Gly Val Pro Asp Arg Phe Ser Gly
    50                  55                  60

Ser Gly Tyr Gly Thr Asp Phe Thr Leu Thr Ile Ser Ser Leu Gln Ala
65                  70                  75                  80

Glu Asp Val Ala Val Tyr Tyr Cys His Gln Ala Tyr Ser Ser Pro Tyr
                85                  90                  95

Thr Phe Gly Gln Gly Thr Lys Leu Glu Ile Lys
            100                 105

<210> SEQ ID NO 75
<211> LENGTH: 114
<212> TYPE: PRT
<213> ORGANISM: Artificial Sequence
<220> FEATURE:
<223> OTHER INFORMATION: 326-3A1 pro-Vh

<400> SEQUENCE: 75

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Asn Asn Gly Glu Pro Thr Tyr Ala Gln Gly Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Leu Val Thr Val
            100                 105                 110

Ser Ser

<210> SEQ ID NO 76
<211> LENGTH: 114
<212> TYPE: PRT
<213> ORGANISM: Artificial Sequence
<220> FEATURE:
<223> OTHER INFORMATION: 326-3C1 pro-Vh

<400> SEQUENCE: 76

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Asn Asn Gly Glu Pro Thr Tyr Ala Gln Asp Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Thr Val Thr Val
            100                 105                 110

Ser Ser

<210> SEQ ID NO 77
<211> LENGTH: 114
<212> TYPE: PRT
<213> ORGANISM: Artificial Sequence
<220> FEATURE:
<223> OTHER INFORMATION: 326-3D1 pro-Vh

<400> SEQUENCE: 77

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Asn Asn Gly Glu Pro Thr Tyr Ala Gln Gly Phe
    50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Leu Val Thr Val
            100                 105                 110

Ser Ser

<210> SEQ ID NO 78
<211> LENGTH: 114
<212> TYPE: PRT
<213> ORGANISM: Artificial Sequence
<220> FEATURE:
<223> OTHER INFORMATION: 326-3E1 pro-Vh

<400> SEQUENCE: 78

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Asn Asn Gly Glu Pro Thr Tyr Ala Gln Asp Phe
    50                  55                  60

Arg Gly Arg Phe Val Phe Ser Leu Asp Thr Ser Ala Ser Thr Ala Tyr
65                  70                  75                  80

-continued

```
Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Thr Val Thr Val
            100                 105                 110

Ser Ser
```

<210> SEQ ID NO 79
<211> LENGTH: 114
<212> TYPE: PRT
<213> ORGANISM: Artificial Sequence
<220> FEATURE:
<223> OTHER INFORMATION: 326-3F1 pro-Vh

<400> SEQUENCE: 79

```
Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Asn Asn Gly Glu Pro Thr Tyr Ala Gln Gly Phe
        50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Thr Val Thr Val
            100                 105                 110

Ser Ser
```

<210> SEQ ID NO 80
<211> LENGTH: 114
<212> TYPE: PRT
<213> ORGANISM: Artificial Sequence
<220> FEATURE:
<223> OTHER INFORMATION: 326-3B N55D pro-Vh

<400> SEQUENCE: 80

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Lys Trp Met
            35                  40                  45

Gly Trp Ile Asn Asn Asn Asp Gly Glu Pro Thr Tyr Ala Gln Asp Phe
        50                  55                  60

Arg Gly Arg Phe Val Phe Ser Leu Asp Thr Ser Ala Ser Thr Ala Tyr
65                  70                  75                  80

Leu Gln Ile Ser Ser Leu Lys Thr Glu Asp Thr Ala Val Tyr Tyr Cys
                85                  90                  95

Ala Arg Asp Val Met Asp Tyr Trp Gly Gln Gly Thr Leu Val Thr Val
            100                 105                 110

Ser Ser
```

<210> SEQ ID NO 81
<211> LENGTH: 110
<212> TYPE: PRT
<213> ORGANISM: Artificial Sequence
<220> FEATURE:
<223> OTHER INFORMATION: 326-4A1 pro-Vk

<400> SEQUENCE: 81

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Arg Thr Asp Phe Thr Leu Thr Ile Asn
65                  70                  75                  80

Pro Val Glu Ala Glu Asp Thr Ala Asn Tyr Tyr Cys Gln Gln Ser Lys
                85                  90                  95

Glu Tyr Pro Thr Phe Gly Gly Gly Thr Lys Val Glu Ile Lys
            100                 105                 110

<210> SEQ ID NO 82
<211> LENGTH: 110
<212> TYPE: PRT
<213> ORGANISM: Artificial Sequence
<220> FEATURE:
<223> OTHER INFORMATION: 326-4A2 pro-Vk

<400> SEQUENCE: 82

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Asp Asn Tyr
            20                  25                  30

Gly Tyr Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln Gln Ser Lys
                85                  90                  95

Glu Tyr Pro Thr Phe Gly Gly Gly Thr Lys Val Glu Ile Lys
            100                 105                 110

<210> SEQ ID NO 83
<211> LENGTH: 327
<212> TYPE: PRT
<213> ORGANISM: Artificial Sequence
<220> FEATURE:
<223> OTHER INFORMATION: huIgG4mt1 pro

<400> SEQUENCE: 83

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

```
Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 84
<211> LENGTH: 327
<212> TYPE: PRT
<213> ORGANISM: Artificial Sequence
<220> FEATURE:
<223> OTHER INFORMATION: huIgG4mt2 pro

<400> SEQUENCE: 84

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95
```

-continued

```
Arg Val Glu Ser Lys Tyr Gly Pro Pro Cys Pro Cys Pro Ala Pro
            100                 105                 110

Pro Val Ala Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 85
<211> LENGTH: 327
<212> TYPE: PRT
<213> ORGANISM: Artificial Sequence
<220> FEATURE:
<223> OTHER INFORMATION: huIgG4mt6 pro

<400> SEQUENCE: 85

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Gly Pro Ser Val Phe Leu Phe Pro Pro Lys Pro Lys
            115                 120                 125
```

```
Asp Thr Leu Met Ile Ser Arg Thr Pro Glu Val Thr Cys Val Val Val
    130                 135                 140
Ala Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Gln Phe
                165                 170                 175
Asn Ser Thr Tyr Arg Val Val Ser Val Leu Thr Val Leu His Gln Asp
                180                 185                 190
Trp Leu Asn Gly Lys Glu Tyr Lys Cys Lys Val Ser Asn Lys Gly Leu
                195                 200                 205
Pro Ser Ser Ile Glu Lys Thr Ile Ser Lys Ala Lys Gly Gln Pro Arg
210                 215                 220
Glu Pro Gln Val Tyr Thr Leu Pro Pro Ser Gln Glu Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
                260                 265                 270
Thr Thr Pro Pro Val Leu Asp Ser Asp Gly Ser Phe Phe Leu Tyr Ser
                275                 280                 285
Arg Leu Thr Val Asp Lys Ser Arg Trp Gln Glu Gly Asn Val Phe Ser
290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 86
<211> LENGTH: 327
<212> TYPE: PRT
<213> ORGANISM: Artificial Sequence
<220> FEATURE:
<223> OTHER INFORMATION: huIgG4mt8 pro

<400> SEQUENCE: 86

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
                35                  40                  45
Gly Val His Thr Phe Pro Ala Val Leu Gln Ser Ser Gly Leu Tyr Ser
            50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
                100                 105                 110
Pro Val Ala Gly Gly Pro Ser Val Phe Leu Phe Pro Pro Lys Pro Lys
                115                 120                 125
Asp Thr Leu Met Ile Ser Arg Thr Pro Glu Val Thr Cys Val Val Val
                130                 135                 140
Thr Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
        180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 87
<211> LENGTH: 327
<212> TYPE: PRT
<213> ORGANISM: Artificial Sequence
<220> FEATURE:
<223> OTHER INFORMATION: huIgG4mt9 pro

<400> SEQUENCE: 87

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
            85                  90                  95

Arg Val Glu Ser Lys Tyr Gly Pro Pro Cys Pro Pro Cys Pro Ala Pro
        100                 105                 110

Pro Val Ala Gly Gly Pro Ser Val Phe Leu Phe Pro Pro Lys Pro Lys
    115                 120                 125

Asp Thr Leu Met Ile Ser Arg Thr Pro Glu Val Thr Cys Val Val Val
130                 135                 140

Ala Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
        180                 185                 190
```

```
Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Lys Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 88
<211> LENGTH: 327
<212> TYPE: PRT
<213> ORGANISM: Artificial Sequence
<220> FEATURE:
<223> OTHER INFORMATION: huIgG4mt10 pro

<400> SEQUENCE: 88

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Ala Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Val His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220
```

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Lys Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 89
<211> LENGTH: 367
<212> TYPE: PRT
<213> ORGANISM: Artificial Sequence
<220> FEATURE:
<223> OTHER INFORMATION: OS8 pro

<400> SEQUENCE: 89

Met Glu Arg His Trp Ile Phe Leu Leu Leu Ser Val Thr Ala Gly
1               5                   10                  15

Val His Ser Gln Val Gln Leu Gln Gln Ser Gly Ala Glu Leu Ala Arg
            20                  25                  30

Pro Gly Ala Ser Val Lys Met Ser Cys Lys Ala Ser Gly Tyr Thr Phe
        35                  40                  45

Thr Arg Tyr Thr Met His Trp Val Lys Gln Arg Pro Gly Gln Gly Leu
    50                  55                  60

Glu Trp Ile Gly Tyr Ile Asn Pro Ser Arg Gly Tyr Thr Asn Tyr Asn
65                  70                  75                  80

Gln Lys Phe Lys Asp Lys Ala Thr Leu Thr Thr Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Asp Asp His Tyr Cys Leu Asp Tyr Trp
        115                 120                 125

Gly Gln Gly Thr Thr Leu Thr Val Ser Ser Gly Gly Gly Gly Ser Gly
    130                 135                 140

Gly Gly Gly Ser Gly Gly Gly Gly Ser Gln Ile Val Leu Thr Gln Ser
145                 150                 155                 160

Pro Ala Ile Met Ser Ala Ser Pro Gly Glu Lys Val Thr Met Thr Cys
                165                 170                 175

Ser Ala Ser Ser Ser Val Ser Tyr Met Asn Trp Tyr Gln Gln Lys Ser
            180                 185                 190

Gly Thr Ser Pro Lys Arg Trp Ile Tyr Asp Thr Ser Lys Leu Ala Ser
        195                 200                 205

Gly Val Pro Ala His Phe Arg Gly Ser Gly Ser Gly Thr Ser Tyr Ser
    210                 215                 220

Leu Thr Ile Ser Gly Met Glu Ala Glu Asp Ala Ala Thr Tyr Tyr Cys
225                 230                 235                 240

Gln Gln Trp Ser Ser Asn Pro Phe Thr Phe Gly Ser Gly Thr Lys Leu
                245                 250                 255

```
Glu Ile Asn Ser Ser Val Pro Val Leu Gln Lys Val Asn Ser Thr
            260                 265                 270

Thr Thr Lys Pro Val Leu Arg Thr Pro Ser Pro Val His Pro Thr Gly
    275                 280                 285

Thr Ser Gln Pro Gln Arg Pro Glu Asp Cys Arg Pro Arg Gly Ser Val
    290                 295                 300

Lys Gly Thr Gly Leu Asp Phe Ala Cys Asp Ile Tyr Ile Trp Ala Pro
305                 310                 315                 320

Leu Ala Gly Ile Cys Val Ala Leu Leu Ser Leu Ile Ile Thr Leu
                325                 330                 335

Ile Cys Tyr His Arg Ser Arg Lys Arg Val Cys Lys Cys Pro Arg Pro
            340                 345                 350

Leu Val Arg Gln Glu Gly Lys Pro Arg Pro Ser Glu Lys Ile Val
            355                 360                 365
```

<210> SEQ ID NO 90
<211> LENGTH: 304
<212> TYPE: PRT
<213> ORGANISM: Artificial Sequence
<220> FEATURE:
<223> OTHER INFORMATION: P3Z pro

<400> SEQUENCE: 90

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Arg
            180                 185                 190

Val Lys Phe Ser Arg Ser Ala Asp Ala Pro Ala Tyr Gln Gln Gly Gln
        195                 200                 205

Asn Gln Leu Tyr Asn Glu Leu Asn Leu Gly Arg Arg Glu Glu Tyr Asp
    210                 215                 220

Val Leu Asp Lys Arg Arg Gly Arg Asp Pro Glu Met Gly Gly Lys Pro
225                 230                 235                 240

Gln Arg Arg Lys Asn Pro Gln Glu Gly Leu Tyr Asn Glu Leu Gln Lys
                245                 250                 255
```

-continued

```
Asp Lys Met Ala Glu Ala Tyr Ser Glu Ile Gly Met Lys Gly Glu Arg
            260                 265                 270

Arg Arg Gly Lys Gly His Asp Gly Leu Tyr Gln Gly Leu Ser Thr Ala
        275                 280                 285

Thr Lys Asp Thr Tyr Asp Ala Leu His Met Gln Ala Leu Pro Pro Arg
    290                 295                 300
```